United States Patent
Ess et al.

(10) Patent No.: US 9,988,349 B2
(45) Date of Patent: Jun. 5, 2018

(54) DIRECT STEREOSPECIFIC SYNTHESIS OF UNPROTECTED AZIRIDINES FROM OLEFINS

(71) Applicants: Daniel Halsell Ess, Provo, UT (US); John Russell Falck, University Park, TX (US); Jawahar Lal Jat, Rajasthan (IN); Laszlo Kurti, Dallas, TX (US)

(72) Inventors: Daniel Halsell Ess, Provo, UT (US); John Russell Falck, University Park, TX (US); Jawahar Lal Jat, Rajasthan (IN); Laszlo Kurti, Dallas, TX (US)

(*) Notice: Subject to any disclaimer, the term of this patent is extended or adjusted under 35 U.S.C. 154(b) by 0 days. days.

(21) Appl. No.: 15/109,396

(22) PCT Filed: Jan. 3, 2015

(86) PCT No.: PCT/US2015/010076
§ 371 (c)(1),
(2) Date: Jun. 30, 2016

(87) PCT Pub. No.: WO2015/103505
PCT Pub. Date: Jul. 9, 2015

(65) Prior Publication Data
US 2016/0340305 A1  Nov. 24, 2016

Related U.S. Application Data

(60) Provisional application No. 61/964,375, filed on Jan. 3, 2014.

(51) Int. Cl.
C07D 203/02  (2006.01)
C07D 203/08  (2006.01)
B01J 31/22  (2006.01)

(52) U.S. Cl.
CPC ........ C07D 203/02 (2013.01); B01J 31/2208 (2013.01); C07D 203/08 (2013.01); B01J 2231/321 (2013.01); B01J 2531/16 (2013.01); B01J 2531/822 (2013.01)

(58) Field of Classification Search
CPC .................................................. C07D 203/02
See application file for complete search history.

(56) References Cited

U.S. PATENT DOCUMENTS 6,008,376 A  12/1999 Sharpless et al.
7,662,969 B2  2/2010 Doyle
8,558,010 B2  10/2013 Karbal et al.
2006/0030718 A1  2/2006 Zhang et al.
2007/0185343 A1  8/2007 Verpoort et al.
2010/0191000 A1  7/2010 Melder et al.
2012/0077990 A1  3/2012 Zhang
2013/0345431 A1  12/2013 Jenkins et al.

FOREIGN PATENT DOCUMENTS

WO  WO 2013/033245  3/2013

OTHER PUBLICATIONS

Lebel, 2011, Organic Letters, vol. 13, No. 20, p. 5460-5463.*
Yamagiwa, 2005, J. Am. Che. Soc., vol. 127, p. 13419-13427.*
Bergmeier et al. "Three-Membered Ring Systems", Ch. 3, pp. 47-73.
Catino et al. "Efficient Aziridination of Olefins Catalyzed by Mixed-Valent Dirhodium(II,III) Caprolactamate", *Organic Letters*, 2005, vol. 7, No. 13, pp. 2787-2790.
Doyle, Michael P. "Perspective on Dirhodium Carboxamidates as Catalysts", *J. Org. Chemical*, 2006, vol. 71, No. 25, pp. 9253-9260.
Gaucher et al. "Fluorous Tagged N-Hydroxy Phthalimide for the Parallel Synthesis of O-Aryloxyamines", *J. Comb Chem.*, 2010, vol. 12(5), pp. 655-658.
Lebel et al. "Copper-Catalyzed Alkene Aziridination with N-Tosyloxycarbamates" *Organic Letters*, 2007, vol. 9, No. 23, pp. 4797-4800.
Search Report for PCT/US2015/010076.
Shen et al. "Unexpected Multiple Electrophilic Addition Reaction of (Z)-Alk-2-en-4-ynoates with N,N-Dibromo-$p$-toluenesulfonamide (TsNBr$_2$): A Highly Diastereoselective Synthesis of Densely Functionalized Aziridines" *American Chemical Society*, 2009, vol. 11, No. 24, pp. 5698-5701.
Yudin, Andrei K. "Aziridines and Epoxides in Organic Synthesis", 2006.
Zalatan et al. "Understanding the Differential Performance of Rh$_2$(esp)$_2$ as a Catalyst for C—H Amination", *J. American Chemical Society*, 2009, vol. 131, pp. 7558-7559.

* cited by examiner

Primary Examiner — Rebecca L Anderson
Assistant Examiner — Karen Cheng
(74) Attorney, Agent, or Firm — Brinks Gilson & Lione; Ryan L. Marshall

(57) ABSTRACT

A method for the direct stereospecific conversion of structurally diverse mono-, di-, tri- and tetra-substituted olefins to N—H, N-alkyl, N-cycloalkyl, or N-aralkyl aziridines using a hydroxylamine amination agent with transition metal catalyst. The method is operationally simple (i.e., one-pot), scalable and fast at ambient temperature.

14 Claims, No Drawings

DIRECT STEREOSPECIFIC SYNTHESIS OF UNPROTECTED AZIRIDINES FROM OLEFINS

RELATED APPLICATION

This application is a 371 national phase of PCT/US2015/010076, filed Jan. 3, 2015, and claims the benefit of the filing date under 35 U.S.C. § 119(e) of U.S. Provisional Patent Application No. 61/964,375 filed on Jan. 3, 2014, the disclosures of which are incorporated by reference herein in their entirety.

TECHNICAL FIELD

The present invention relates to processes of making N—H, N-alkyl, N-cycloalkyl, and N-aralkyl aziridines from olefins using transition metal catalysts and hydroxylamines.

BACKGROUND

Aziridines, the triangular, comparably highly-strained nitrogen analogues of epoxides, are important synthetic intermediates (i.e., building blocks) en route to structurally complex molecules because of their versatility in myriad regio- and stereo-selective transformations (ring openings and expansions as well as rearrangements). The aziridine structural motif, predominantly N—H and to a lesser extent N-alkyl, and N-aralkyl, also appears in biologically active natural products (e.g., azinomycins and mitomycins). As a result, the synthesis and chemistry of aziridines has been the subject of intense research during the past 25 years, resulting in multiple aziridination methods. Most of these methods rely either on the transfer of substituted nitrenes, which are generated using strong external oxidants, to the C═C bond of olefins or the transfer of substituted carbenes to the C═N bond of imines (see Scheme A). Normally, the result is an aziridine bearing a strongly electron-withdrawing N-protecting group (e.g., Ts: para-toluenesulfonyl, Ns: para-nitrophenylsulfonyl); removal of these N-sulfonyl protecting groups is problematic as it often results in the undesired opening of the aziridine ring. In addition, the high reactivity of N-protected nitrenes might give rise to non-productive allylic C—H amination products, as well as the loss of stereospecificity. Clearly, the direct synthesis of N—H (i.e., N-unprotected), N-alkyl, and N-aralkyl aziridines would alleviate the above problems. However, a practical, functional group-tolerant and environmentally benign direct preparation of N—H), N-alkyl, and N-aralkyl aziridines from structurally diverse olefins has so far eluded synthetic chemists.

Vicinal oxidative difunctionalizations (i.e., the creation of two bonds during the same overall transformation such as epoxidation, dihydroxylation, aziridination, amino-hydroxylation and diamination, see Scheme A) of olefins are amongst the most powerful and atom economical maneuvers available for the direct introduction of heteroatoms into simple, unfunctionalized molecules. The resulting difunctional products are obtained in a single step while the molecular complexity is significantly increased (e.g., introducing one or more heteroatoms and stereogenic centers). The resultant products are prized as synthetic building blocks for even larger and structurally more complex molecules such as natural products or active pharmaceutical ingredients. Despite significant advances in this field, many challenges remain that limit the scope and applicability of these difunctionalization reactions, especially in an industrial setting. This is cogently exemplified by the many issues with the direct aminohydroxylation of olefins, a widely used difunctionalization developed by researchers during the 1990s: (1) poor regioselectivity; (2) limited chemoselectivity and substrate scope; (3) use of highly toxic osmium complexes that are difficult to contain due to the comparatively high vapor pressure of osmium derivatives; (4) need for stoichiometric oxidizing agents that pose a fire and explosion hazard, especially when heated; and (5) difficulty in removing the strong electron-withdrawing groups from the N-atom.

In particular, the introduction of unprotected nitrogen in a single step and under mild conditions could result in processes that are faster, more economical, and less wasteful (i.e. greener) than currently used multi-step routes. There exists, therefore, a need in the art for processes to prepare aziridines, including N—H aziridines among others.

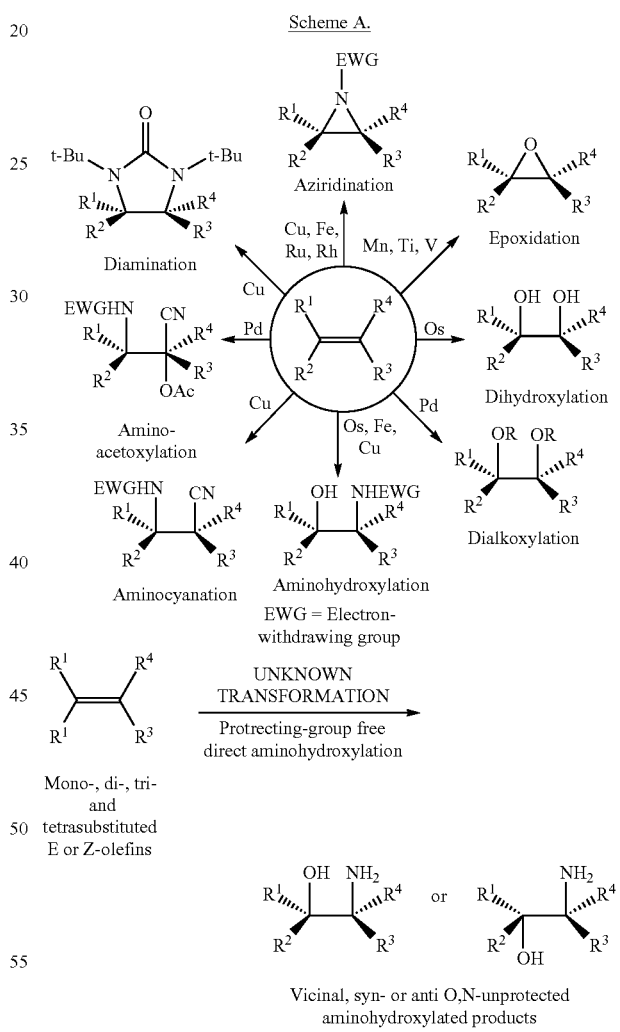

SUMMARY OF THE INVENTION

In one aspect, a process for making an aziridine is disclosed which includes reacting an olefin with a hydroxylamine amination agent in the presence of a transition metal catalyst, wherein the aziridine product is an N—H, N-alkyl, N-cycloalkyl, or N-aralkyl aziridine.

In some embodiments, the hydroxylamine amination agent is selected from compounds of formulas:

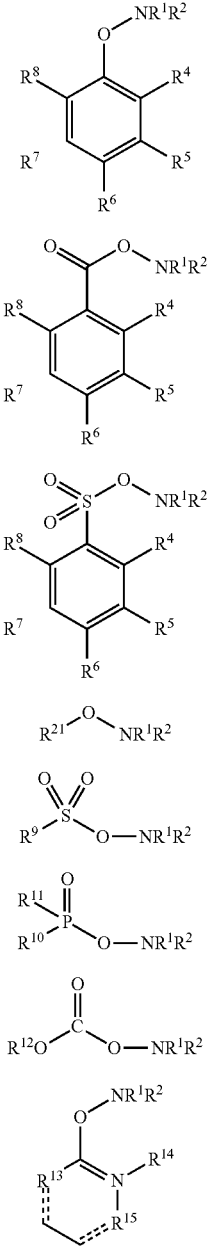

wherein each $R^1$ and $R^2$ are independently selected from hydrogen, $C_1$-$C_{18}$ alkyl, $C_3$-$C_8$ cycloalkyl, —Si($R^3$)$_3$, allyl, aralkyl, substituted and unsubstituted aryl, and substituted and unsubstituted heteroaryl; wherein $R^1$ and $R^2$ can be connected to form a cyclic amine having from 4 to 7 carbocyclic ring members; each $R^3$ is independently selected from $C_1$-$C_{18}$ alkyl and substituted or unsubstituted aryl; each $R^4$, $R^5$, $R^6$, $R^7$, and $R^8$ are independently selected from hydrogen, nitro, fluoro, chloro, bromo, $C_1$-$C_{18}$ alkyl, $C_3$-$C_8$ cycloalkyl, arylsulfonyl, alkylsulfonyl, mono-/di-/tri-fluoroalkylsulfonyl, trifluoromethyl, $R^{16}R^{17}NC(O)$—, $R^{18}O_2C$—, $(R^{19})_4N^+$—, and $(R^{20})_2P(O)$—; $R^9$ is selected from substituted and unsubstituted $C_1$-$C_{18}$ alkyl, $C_3$-$C_8$ cycloalkyl and substituted and unsubstituted aryl; $R^{10}$ and $R^{11}$ are independently selected from substituted and unsubstituted aryl; wherein the number of substituents for substituted aryl may be from 1 to 5 and independently selected from nitro, fluoro, chloro, methyl, ethyl, isopropyl, tert-butyl, arylsulfonyl, alkylsulfonyl, mono-/di-/tri-fluoroalkylsulfonyl, trifluoromethyl, $R^{16}R^{17}NC(O)$—, $R^{18}O_2C$—, $(R^{19})_4N^+$—, $(R^{20})_2P(O)$—, $PEG_m$-, and o-furanyl; $R^{12}$ is selected from $C_1$-$C_{18}$ alkyl, $C_3$-$C_8$ cycloalkyl, $C_1$-$C_8$ alkenyl, $C_3$-$C_8$ cycloalkenyl, substituted and unsubstituted aryl; wherein the number of substituents for substituted aryl may be from 1 to 5 and independently selected from nitro, fluoro, chloro, methyl, ethyl, isopropyl, tert-butyl, arylsulfonyl, alkylsulfonyl, mono-/di-/tri-fluoroalkylsulfonyl, trifluoromethyl, $R^{16}R^{17}NC(O)$—, $R^{18}O_2C$—, $(R^{19})_4N^+$—, $(R^{20})_2P(O)$—, $PEG_m$-, and o-furanyl; $R^{13}$ is selected from substituted and unsubstituted aryl, substituted and unsubstituted heteroaryl, $C_1$-$C_{18}$ alkyl, $C_3$-$C_8$ cycloalkyl, $CCl_3$, and $CF_3$, or when $R^{13}$ forms an aromatic or other ring system with $R^{15}$, then $R^{13}$ is selected from O, N, and C—$R^{20}$; wherein the number of substituents for substituted aryl may be from 1 to 5 and wherein the number of substituents for substituted heteroaryl may be from 1 to 4 and each substituent is independently selected from nitro, fluoro, chloro, methyl, ethyl, isopropyl, tert-butyl, arylsulfonyl, alkylsulfonyl, mono-/di-/tri-fluoroalkylsulfonyl, trifluoromethyl, $R^{16}R^{17}NC(O)$—, $R^{18}O_2C$—, $(R^{19})_4N^+$—, and $(R^{20})_2P(O)$—, $PEG_m$-, and o-furanyl; $R^{14}$ is absent or selected from H, substituted and unsubstituted aryl, $C_3$-$C_8$ cycloalkyl, and $C_1$-$C_{18}$ alkyl, wherein the number of substituents for substituted aryl may be from 1 to 5 and wherein the number of substituents for substituted heteroaryl may be from 1 to 4 and each substituent is independently selected from nitro, fluoro, chloro, methyl, ethyl, isopropyl, tert-butyl, arylsulfonyl, alkylsulfonyl, mono-/di-/tri-fluoroalkylsulfonyl, trifluoromethyl, $R^{16}R^{17}NC(O)$—, $R^{18}O_2C$—, $(R^{19})_4N^+$—, and $(R^{20})_2P(O)$—, $PEG_m$-, $R^{15}$ is selected from selected from substituted and unsubstituted aryl, $C_1$-$C_8$ alkyl, and $C_3$-$C_8$ cycloalkyl, or when $R^{15}$ forms an aromatic or other ring system with $R^{13}$, then $R^{15}$ is CH or $CH_2$; wherein the number of substituents for substituted aryl may be from 1 to 5 and each substituent is independently selected from nitro, fluoro, chloro, methyl, ethyl, isopropyl, tert-butyl, arylsulfonyl, alkylsulfonyl, mono-/di-/tri-fluoroalkylsulfonyl, trifluoromethyl, $R^{16}R^{17}NC(O)$—, $R^{18}O_2C$—, $(R^{19})_4N^+$—, and $(R^{20})_2P(O)$—, $PEG_m$-.

where each m is independently from 1 to 6; each $R^{16}$, $R^{17}$, $R^{18}$, $R^{19}$, $R^{20}$ is independently selected from H, $C_3$-$C_8$ cycloalkyl, substituted and unsubstituted aryl, substituted and unsubstituted heteroaryl, and $C_1$-$C_8$ alkyl; wherein the number of substituents for each substituted aryl may be from 1 to 5 and the number of substituents for each substituted heteroaryl may be from 1 to 4 and each substituent is independently selected from nitro, fluoro, chloro, methyl, ethyl, isopropyl, tert-butyl, arylsulfonyl, alkylsulfonyl, mono-/di-/tri-fluoroalkylsulfonyl, trifluoromethyl, $PEG_m$-; $R^{21}$ is $C_1$-$C_{18}$ alkyl substituted with an electron withdrawing group.

In some embodiments, the hydroxylamine amination agent is of formula AA-1. In some embodiments, the hydroxylamine amination agent is of formula AA-2. In some embodiments, the hydroxylamine amination agent is of formula AA-3. In some embodiments, the hydroxylamine amination agent is of formula AA-4. In some embodiments, the hydroxylamine amination agent is of formula AA-5. In some embodiments, the hydroxylamine amination agent is of formula AA-6. In some embodiments, the hydroxylamine amination agent is of formula AA-7. In some embodiments, the hydroxylamine amination agent is of formula AA-8.

In some embodiments, the transition metal catalyst is copper. In some embodiments, the transition metal catalyst is rhodium. In some embodiments, the transition metal catalyst is selected from: $Rh_2(OAc)_4$, $Rh_2(octanoate)_4$, and $Rh_2(esp)_2$. In some embodiments, the transition metal catalyst includes one or more chiral ligands.

In some embodiments, the olefin is selected from formulas:

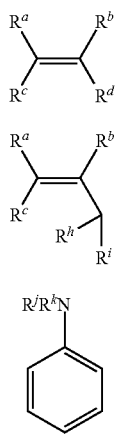

O-1

O-2

O-3 wherein each of $R_a$, $R_b$, $R_c$, $R_d$, $R_h$, and $R_i$ is independently selected from H, substituted and unsubstituted aryl, $C_1$-$C_{18}$ alkyl, $C_3$-$C_8$ cycloalkyl, $C_2$-$C_{18}$ alkenyl, $C_3$-$C_8$ cycloalkenyl, $C_2$-$C_{18}$ alkynyl; and Rj and Rk are independently H, $C_1$-$C_{18}$ alkyl, and $C_3$-$C_8$ cycloalkyl. In some embodiments, the olefin is of formula O-1. In some embodiments, the olefin is of formula O-2. In some embodiments, the olefin is of formula O-3.

In some embodiments, the olefin is of Formula IM-1

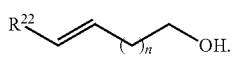

IM-1 where $R^{22}$ is selected from H, substituted and unsubstituted aryl, $C_1$-$C_{18}$ alkyl, $C_3$-$C_8$ cycloalkyl, $C_2$-$C_{18}$ alkenyl, $C_3$-$C_8$ cycloalkenyl, $C_2$-$C_{18}$ alkynyl; and n is an integer of from 1 to 16.

In some embodiments, the aziridine product is of one of the following formulas:

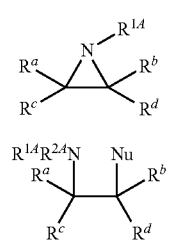

AP-1

AP-2

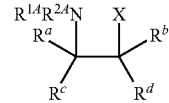

AP-3

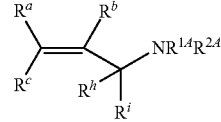

AP-4

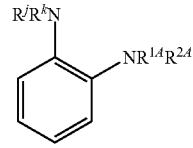

AP-5 where $R^{1A}$ and $R^{2A}$ are each independently selected from H, $C_1$-$C_{18}$ alkyl, $C_3$-$C_8$ cycloalkyl, and aralkyl; and Nu is selected from —$N_3$, —OH, —OR, halogen, and —OC(O)R, and heterocyclyl; R is $C_1$-$C_{18}$ alkyl, and substituted or unsubstituted aryl; X is allyl or aryl.

In some embodiments, the aziridine product is of formula AP-1. In some embodiments, the aziridine product is of formula AP-2. In some embodiments, the aziridine product is of formula AP-3. In some embodiments, the aziridine product is of formula AP-4. In some embodiments, the aziridine product is of formula AP-5.

In some embodiments, the aziridine product is of formula IM-5

IM-5

In some embodiments, the transition metal catalyst is incrementally added. In some embodiments, the reaction takes place in a polar, hydroxylic, and non-nucleophilic solvent. In some embodiments, the solvent is selected from 2,2,2-trifluoroethanol, acetonitrile, water, methanol, ethanol, dichloromethane, tetrahydrofuran, and mixtures of the same. In some embodiments, the process is a one-pot process.

In some embodiments, the aziridine product is an N—H aziridine. In some embodiments, the aziridine product is an N-alkyl aziridine. In some embodiments, the aziridine product is an N-cycloalkyl aziridine. In some embodiments, the aziridine product is an N-aralkyl aziridine.

DETAILED DESCRIPTION

Definitions

As used herein, the term "alkyl" refers to a straight or branched hydrocarbon radical or group having at least one carbon atom including but not limited to saturated $C_1$-$C_6$ such as: methyl, ethyl, 1-propyl and 2-propyl, 1-butyl, 2-butyl, 2-methyl-1-propyl, 1,1-dimethylethyl, 1-pentyl, 2-pentyl, 3-pentyl, 2-methyl-1-butyl, 3-methyl-1-butyl, 2,2-dimethylpropyl, 1-hexyl, 2-hexyl, 3-hexyl, 2-methyl-1-pentyl, 3-methyl-1-pentyl, 4-methyl-1-pentyl, 3,3-dimethyl-1-butyl, 3,3-dimethyl-2-butyl, 2-ethyl-1-butyl and the like; $C_7$-$C_{12}$ such as: 1-heptyl, 2-heptyl, 3-heptyl, 4-heptyl, 2-methyl-1-hexyl, 4-methyl-1-hexyl, 5-methyl-1-hexyl, 1-octyl, 2-octyl, 3-octyl, 4-octyl, 6-methyl-1-heptyl, 5,5-dimethyl-1-hexyl, 2-ethyl-1-hexyl, 2-methyl-1-heptyl, 2-propyl-1-pentyl, 1-nonyl, 2-nonyl, 2-ethyl-2-methyl-1-hexyl, 4-methyl-1-octyl, 3,5,5-trimethyl-1-hexyl, 1-decyl, 2-decyl, 4-ethyl-1-octanyl, 2-methyl-1-nonyl, 4-methyl-1-nonyl, 8-methyl-1-nonyl, 1-undecyl (1-hendecyl), 2-undecyl, 7-methyl-1-decyl, 1-dodecyl, 5-dodecyl, 2-butyl-1-octyl, 10-methyl-1-undecyl and the like; $C_{13}$-$C_{18}$ such as: 1-tridecyl, 4-methyl-1-dodecyl, 11-methyl-1-dodecyl, 1-butyldecyl, 11-methyl-1-tridecyl, 1-pentadecyl, 1-hexadecyl, 2-hexyl-1-decyl, 1-heptadecyl, 14-methyl-1-hexadecyl, 15-methyl-1-hexadecyl, 1-octadecyl, 16-methyl 1-heptadecyl and the like. Alkyl groups may be unsubstituted or substituted. When the alkyl group is substituted, it may be substituted with one or more fluoro substituents, for example 1, 2, or 3 fluoro substituents. In some embodiments, alkyl includes cycloalkyl.

The term "cycloalkyl" as used herein means a monocyclic hydrocarbyl group having from 3 to 8 carbon atoms (i.e. $C_3$-$C_8$). Illustrative examples of a cycloalkyl group or radical include cyclopropyl, cyclobutyl, cyclopenyl, cyclohexyl, cycloheptyl, cyclooctyl, Cycloalkyl groups may be unsubstituted or substituted. Suitable substituents for cycloalkyl include fused heteroaryl such as fused indole, and unsubstituted aryl, e.g. —$OCH_3$, and —$CO_2CH_3$.

The term "heterocyclyl" refers to cycloalkyl in which at least one carbon atom is substituted with a heteroatom selected from O and N. For purposes of this disclosure, heterocyclyl does not include heterocycles having sulfur atom in the ring system. Examples of heterocyclyl include oxiranyl, pyrrolidinyl, piperidyl, tetrahydropyran, and morpholine. Suitable substituents for heterocyclyl include fused cycloalkyl such fused cyclohexyl and cyclopenytl The term "alkenyl" refers to an unsaturated aliphatic group having at least one double bond (two adjacent $sp^2$ carbon atoms). Depending on the placement of a double bond and substituents, if any, the geometry of the double bond may be trans (E) or cis (Z). Unsaturated alkenyl may have one or more double bonds (units of unsaturation). Like alkyl groups, unsaturated groups may be straight chain or branched. Examples of alkenyls include vinyl, allyl, 2-methyl-2-propenyl, cis-2-butenyl, trans-2-butenyl, and acetyl, propene, 1-butene, 2-butene, 2-methylpropene, 1-pentene, 2-pentene, 2-methyl-1-butene, 2-methyl-2-butene, 3-methyl-1-butene, 1-hexene, 2-hexene, 3-hexene, 2,3-dimethyl-1-butene, 2,3-dimethyl-2-butene, 3,3-dimethyl-1-butene, 2-dimethyl-2-butene, 2-ethyl-1-butene, 2-methyl-1-pentene, 2-methyl-2-pentene, 3-methyl-1-pentene, 3-methyl-2-pentene, 4-methyl-1-pentene, 4-methyl-2-pentene, 1-heptene, 2-heptene, 3-heptene, 3,4-dimethyl-2-pentene, 4,4-dimethyl-2-pentene, 3-methyl-2-hexene, 3-methyl-3-hexene, 4-methyl-2-hexene, 2,3-dimethyl-1-pentene, 2,3-dimethyl-2-pentene, 2,4-dimethyl-1-pentene, 2,4-dimethyl-2-pentene, 3,3-dimethyl-1-pentene, 3,4-dimethyl-1-pentene, 4,4-dimethyl-1-pentene, 4,4-dimethyl-2-pentene, 3-ethyl-1-pentene, 3-ethyl-2-pentene, 2-methyl-1-hexene, 2-methyl-2-hexene, 3-methyl-1-hexene, 4-methyl-1-hexene, 5-methyl-1-hexene, 2,3,3-trimethyl-1-butene, 1-octene, 2-octene, 3-octene, 4-octene, 2,2-demethyl-3-hexene, 2,3-dimethyl-2-hexene, 2,3-dimethyl-3-hexene, 3-ethyl-2-methyl-1-pentene, 3-ethyl-2-methyl-pent-2-ene, 2-isopropyl-1-pentene, 2-methyl-1-heptene, 2-methyl-2-heptene, 4-methyl-2-heptene, 2,3,4-trimethyl-2-pentene, 2,4,4-trimethyl-1-pentene, 2,4,4-trimethyl-2-pentene, 3,4,4-trimethyl-2-pentene, 1-nonene, 2-nonene, 3-nonene, 4-nonene, 2,2-dimethyl-3-heptene, 3,5,5-trimethyl-1-hexene, 1-decene, 4-decene, 5-decene, 3,7-dimethyl-1-octene, 2-methyl-1-nonene, 1-undecene,trisisobutylene, 2,2,4,6,6-pentamethyl-3-heptene, 1-dodecene, 2-methyl-1-undecene, 1-tridecene, 1, 1-dineopentylethylene, 1-tetradecene, 7-tetradecene, 1-pentadecene, 1-hexadecene, 1-heptadecene, 8-heptadecene, 1-octadecene, 1-nonadecene, 1-eicosene, 9-heneicosene, 1-docosene and the like.

Examples of dialkenes include but are not limited to propandiene (allene), 1,3-butadiene, 1,3-pentadiene, 1,4-pentadiene, 2-methyl-1,3-butadiene (isoprene), 3-methyl-1, 2-butadiene, 1,3-hexadiene, 1,4-hexadiene, 1,5-hexadiene, 2,4-hexadiene, 2,3-dimethyl-1,3-butadiene, 2-methyl-1,3-pentadiene, 2-methyl-1,4-pentadiene, 3-methyl-1,4-pentadiene, 4-methyl-1,3-pentadiene, 3-methyl-1,3-pentadiene 1-heptyne, 2-heptyne, 3-heptyne, 2,4-dimethyl-1,3-pentadiene, 2,4-dimethyl-2,3-pentadiene, 1,6-heptadiene, 1,7-octadiene, 1,4-octadiene, 3-methyl-1,5-heptadiene, 2,5-dimethyl-1,5-hexadiene, 2,5-dimethyl-1,4-hexadiene, 1,8-nonadiene, 7-methyl-1,6-octadiene 1,9-decadiene, 7-dimethyl-1,6-octadiene, 5,7-dimethyl-1,6-octadiene 1,7-hexadecadiene and the like.

Examples of trialkenes include but are not limited to 5-methyl-1,3,6-heptatriene, 2,6-dimethyl-2,4,6-octatriene (neo-alloocimene), 1,5,9-decatriene, 2,6-dimethyl-2,4,6-octatriene, 3,7-dimethyl-1,3,6-octatriene, 7-methyl-3-methylene-1,6-octadiene, 3,7-dimethyl-1,3,6-octatriene, 1,4,9-decatriene, 1,3,5-undecatriene and the like. Examples of alkynyls include, but are not limited to 1-butyne, 2-butyne, 1-pentyne, 2-pentyne, 4-methyl-pent-1-yne, 1-hexyne, 2-hexyne, 3-hexyne, 3,3-dimethyl-1-butyne, 1-heptyne, 2-heptyne, 3-heptyne, 5-methyl-1-hexyne, 1-octyne, 2-octyne, 3-octyne, 4-octyne, 1-nonyne, 1-decyne, 5-decyne and 1-dodecyne, 1-pentadecyne and the like.

The term "alkynyl" refers to a at least partially unsaturated, straight-chain or branched hydrocarbon group that contains from 2 to 18 carbon atoms. Examples of alkynyls include ethynyl, propynyl, butynyl, acetylenyl, propargyl and the like.

Alkenyl and alkynyl groups may be unsubstituted or substituted.

The term "aryl" as used herein means an aromatic carbocyclic ring having from 6 to 14 carbon atoms. Illustrative examples of an aryl group or radical include phenyl, 1-naphthyl, 2-naphthyl, 1-anthryl, 2-antrhyl, 9-anthryl, 1-phenanthryl, 2-phenanthryl, 3-phenanthryl, 4-phenanthryl, 5-phenanthryl, and the like; including fused ring systems with rings that have less than 6 carbons such as 1-acenaphthyl, 3-acenaphthyl, 4-acenaphthyl, 5-acenaphthyl, 1-azulyl, 2-azulyl, 4-azulyl, 5-azulyl, 6-azulyl and the like. Suitable substituents for aryl include sulfoxide, sulfone, and phosphorous(V) substituents. In some embodiments, sulfur (i.e. thiol), and phosphorous(III) substituents are not suitable aryl substituents.

The term "heteroaryl" means an unsaturated monocyclic group or radical of 5 or 6 atoms, an unsaturated fused bicyclic group or radical of from 8 to 10 atoms, or an unsaturated fused tricyclic group or radical of from 11 to 14 atoms, the cyclic groups having one or more heteroatoms independently selected from O, N, or S. Illustrative examples of monocyclic heteroaryl include 2- or 3-thienyl, 2- or 3-furanyl, 1-, 2-, or 3-pyrrolyl, 1-, 2-, or 4-imidazolyl, 1-, 3-, or 4-pyrazolyl, 2-, 4-, or 5-oxazolyl, 2-, 4-, or 5-thiazolyl, 3-, 4-, or 5-isoxazolyl, 3-, 4-, or 5-isothiazolyl, 2-, 3-, or 4-pyridinyl, 3- or 4-pyridazinyl, 2- or 3-pyrazinyl, and 2-, 4-, or 5-pyrimidinyl. Illustrative examples of bicyclic heteroaryl include 2-, 3-, 4-, 5-, 6-, 7-, or 8-quinolinyl, 1-, 3-, 4-, 5-, 6-, 7-, or 8-isoquinolinyl, 1-, 2-, 3-, 4-, 5-, 6-, or 7-indolyl, 2-, 3-, 4-, 5-, 6-, or 7-benzo[b]thienyl, 2-, 4-, 5-, 6-, or 7-benzofuran, 2-, 4-, 5-, 6-, or 7-benzoxazolyl, 2-, 4-, 5-, 6-, or 7-benzothiazolyl, and 1-, 2-, 3-, 4-, 5-, 6-, or 7-benzimidazolyl. Illustrative examples of tricyclic heteroaryl include 1-, 2-, 3-, or 4-dibenzofuranyl, 1-, 2-, 3-, or 4-dibenzothienyl, and 1-, 2-, 3-, 4-, 5-, 6-, 7-, 8-, or 9-(1,2,3,4-tetrahydroacridinyl). Heteroaryl groups may be unsubstituted or substituted. Suitable substituents for heteroaryl include fused cycloalkyl such as fused cyclopentyl or cyclohexyl, and —O—$C_1$-$C_{18}$ alkyl and fluoro.

As used above, a fused bicyclic group or radical is a group wherein two ring systems share two and only two atoms. As used above, a fused tricyclic group or radical is a group wherein three ring systems share four and only four atoms.

The term "aralkyl" as used herein means an alkyl having at least one alkyl hydrogen atom replaced with an aryl, such as benzyl or picolyl, and the like, all of which may be optionally substituted. Illustrative examples of an aralkyl group or radical include benzyl, Ph-(CH(CH$_3$))—, 2-phenylethyl, 3-phenylpropyl, 4-phenylbutyl, 3-methyl-3-phenylpropyl, and 4-phenylheptyl.

The term "aralkyl" refers to an alkyl group substituted with an aryl group. Suitable aralkyl groups include benzyl, picolyl, and the like, all of which may be optionally substituted.

The terms "halo" and "halogen" mean a halogen such as fluoro, chloro, bromo, and iodo. In some embodiments, the halogen may be selected from fluoro, chloro, and bromo. In some embodiments, the halogen may be selected from fluoro and chloro. In some embodiments, the halogen may be fluoro. In some embodiments, the halogen may be chloro. In some embodiments, the halogen may be bromo.

The processes disclosed herein describe an operationally simple, inherently safe, chemoselective and stereospecific conversion of a wide range of olefins to the corresponding N—H, N-alkyl (for example N-Me), and N-aralkyl aziridines via a transition metal—such as rhodium-catalyzed pathway free of external oxidants.

Recently, we developed a metal-free protocol for primary amination of arylboronic acids using only O-(2,4-dinitrophenyl)hydroxylamine (DPH, 1a, Scheme 1A) as the stoichiometric aminating agent. The transformation proceeds under neutral or basic conditions and can be conducted on a multigram scale to provide structurally diverse primary arylamines. The versatility and robustness of 1a prompted us to explore other uses of this aminating agent, specifically for the direct functionalization of readily available and inexpensive olefins. Our investigations began by subjecting 1:1.5 mixtures of cis-methyl oleate 7/1a (see Scheme 1B) as well as styrenes (3a & 3b)/1a (see Scheme 1A) to a vigorous screening with a variety of transition metal complexes (tables S1 and S2). This initial screen identified $Rh_2(OAc)_4$ as a promising catalyst for vicincal-amino-oxyarylation of olefins. Further evaluation of dimeric rhodium dicarboxylate complexes (table S3), revealed that just 1 mol % loading of Du Bois' catalyst (2, Scheme 1A) in acetonitrile (MeCN) leads to amino-oxyarylated styrenes 4a and 4b at room temperature in 56% and 75% isolated yields, respectively. These promising results prompted us to conduct a thorough solvent screen.

Scheme 1A.

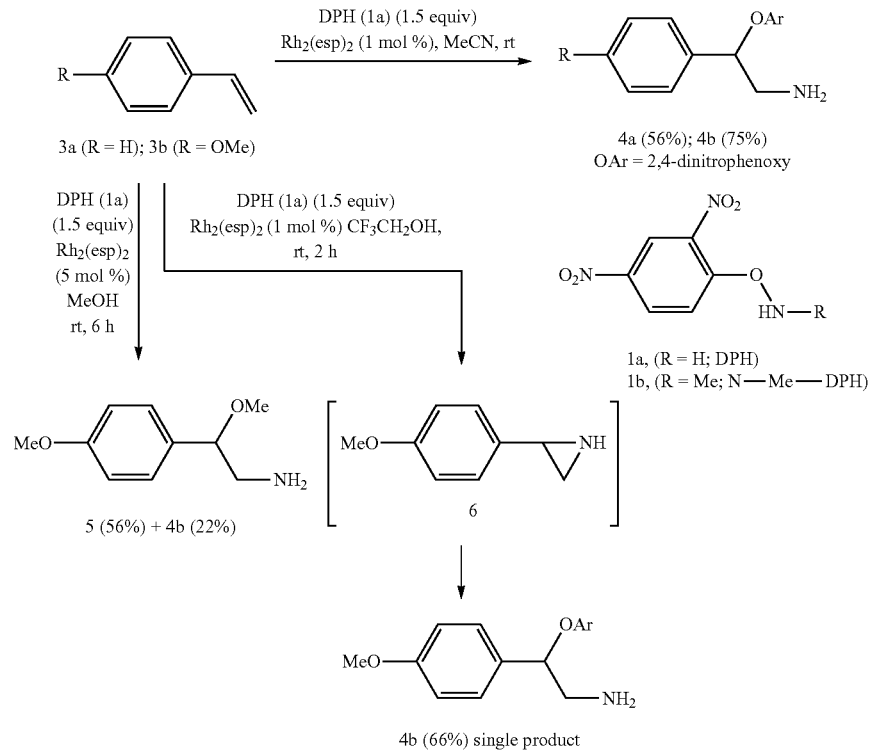

In methanol, we observed the incorporation of the MeO group at the benzylic position (5) in addition to the amino-oxyarylated product 4b; these compounds were isolated in a combined yield of 78%. We examined whether a highly polar, hydroxylic and nonnucleophilic solvent such as 2,2,2-trifluoroethanol (CF$_3$CH$_2$OH, TFE) would completely avoid the incorporation of solvent into the products. Indeed, 3b was cleanly amino-oxyarylated in TFE and 4b was isolated in 66% yield (see Scheme 1A). It was unclear if the transformation 3b-*4b involved the opening of a highly reactive aziridine (6) or an alternative process.

Surprisingly, when 7 was reacted in trifluoroethanol as solvent, cis-N—H aziridine 8 was isolated in excellent yield (83%) instead of the expected amino-oxyarylated product (see Scheme 1B). The transformation proceeded with complete stereospecificity as no traces of the trans-N—H aziridine were detected by $^1$H- and $^{13}$C-nuclear magnetic resonance ($^{13}$C-NMR) analysis (≤2% sensitivity).

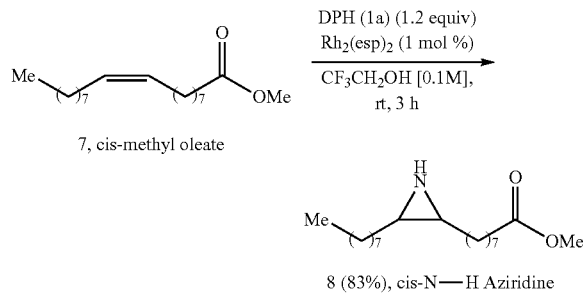

Because of this unexpected result, we initiated a systematic study using representative aliphatic olefins with a wide range of substitution patterns and functionalities (see Scheme 2). Terminal aliphatic olefin substrates (entries 1-3, Scheme 2) either did not react or reacted sluggishly (i.e., days) when 1 mol % of catalyst 2 was used; however, increasing the catalyst loading to 5 mol % led to rapid conversion at room temperature to the corresponding N—H aziridines (10a-c). We empirically found that in some of the reactions (i.e., entries 4, 5, 7, 9, 11, 14, and 20), addition of the catalyst in several 1 mol % portions minimized decomposition of both the catalyst and aminating agent and invariably led to higher isolated yield of product. The N—H aziridination took place efficiently in the presence of a labile terminal epoxide (10c) as well as an unprotected primary alcohol (10a); these functionalities typically interfere with currently used aziridination protocols. In case of the transformation 9c→10c, only the product was detected in the crude reaction mixture by NMR analysis. In the presence of 1 mol % of catalyst 2, both cis- and trans-1,2-disubstituted aliphatic olefins (entries 4-10, Scheme 2) underwent smooth and stereospecific N—H aziridination at room temperature as established by $^{13}$C-NMR analysis (≤2% sensitivity). The presence of an unprotected secondary alcohol in substrate 9i (entry 9) did not influence the stereochemical outcome of the N—H aziridination and 10i was isolated as a 1:1 mixture of diastereomers.

Benzoyloxy and acetyloxy cis-olefins 9k and 9m (entries 11 & 14), when exposed to 1 mol % of the Du Bois catalyst 2 and 1.2 equivalents of aminating agent 1a at 50° C., were smoothly aziridinated followed by an in situ aziridine ring-opening (via transacylation) to yield the corresponding trans-2,3-disubstituted furans 10kk and 10 mm in 84% and 61% yields, respectively. By contrast, when olefin 9k was exposed to 5 mol % loading of catalyst 2 and 1.2 equivalents of 1a at 25° C., the expected N—H aziridine 10k (entry 12) was formed in just 2 hours and isolated in 69% yield. As anticipated, when the rate of N—H aziridination is slow and elevated

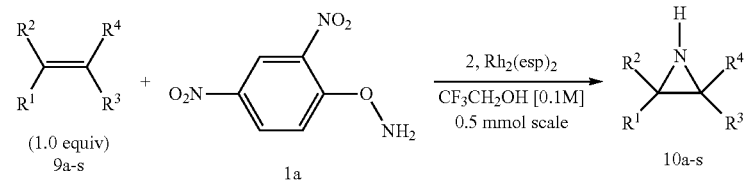

Structure of N—H Aziridines
(Entry): Compound #; T (° C.), t (h), Isolated Yield (%), Regio- and diastereoselectivity [ratios]

N—H Aziridination of aliphatic mono-, di-, and tri-substituted olefins:

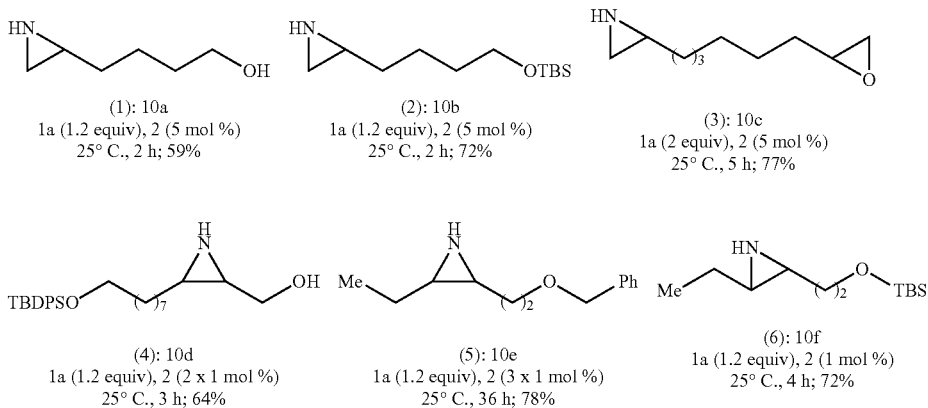

-continued
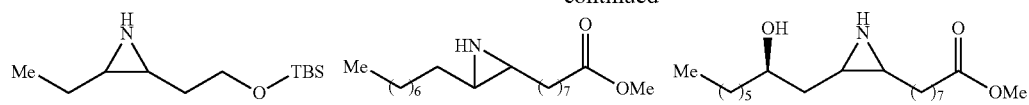
(7): 10g
1a (1.2 equiv), 2 (2 × 1 mol %)
25° C., 29 h; 55%
(8): 10h
1a (1.2 equiv), 2 (1 mol %)
25° C., 2 h; 91%
(9): 10i
1a (1.2 equiv), 2 (3 × 1 mol %)
25° C., 6 h; 82% [1:1 dr]
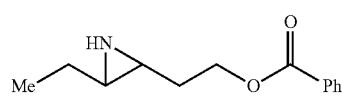
(10): 10j
1a (1.2 equiv), 2 (1 mol %)
25° C., 1 h; 86% + 4% of 10jj
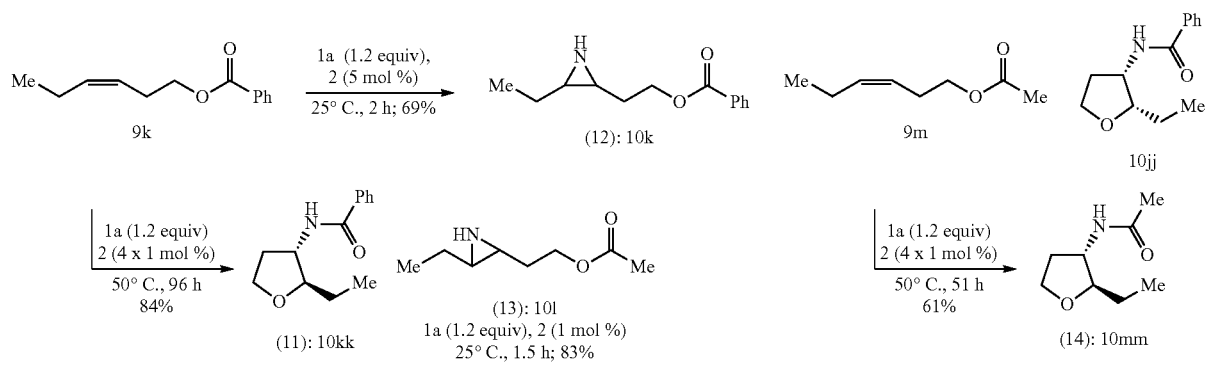
(11): 10kk
50° C., 96 h
84%
(13): 10l
1a (1.2 equiv), 2 (1 mol %)
25° C., 1.5 h; 83%
(14): 10mm
1a (1.2 equiv)
2 (4 × 1 mol %)
50° C., 51 h
61%
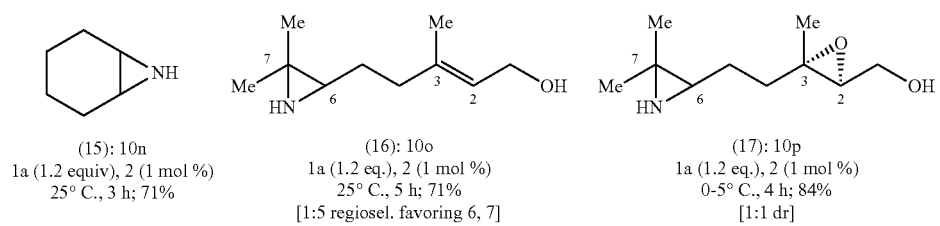
(15): 10n
1a (1.2 equiv), 2 (1 mol %)
25° C., 3 h; 71%
(16): 10o
1a (1.2 eq.), 2 (1 mol %)
25° C., 5 h; 71%
[1:5 regiosel. favoring 6, 7]
(17): 10p
1a (1.2 eq.), 2 (1 mol %)
0-5° C., 4 h; 84%
[1:1 dr]
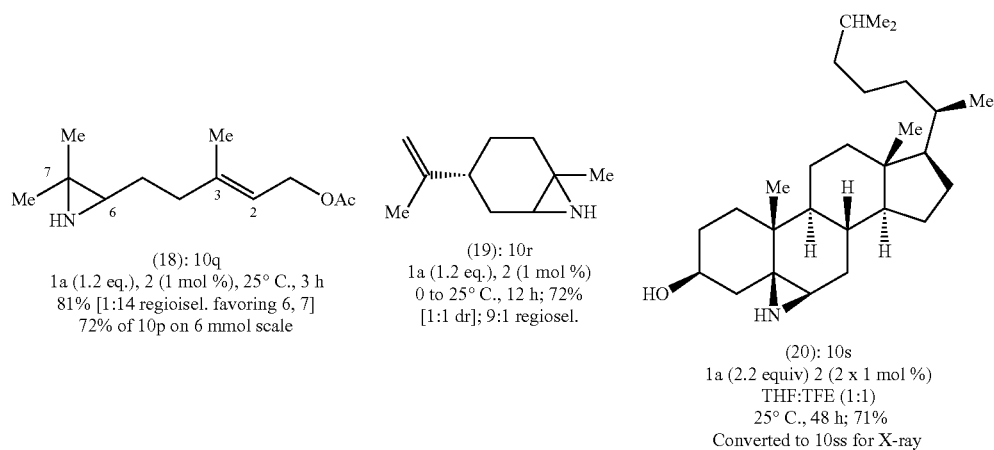
(18): 10q
1a (1.2 eq.), 2 (1 mol %), 25° C., 3 h
81% [1:14 regioisel. favoring 6, 7]
72% of 10p on 6 mmol scale
(19): 10r
1a (1.2 eq.), 2 (1 mol %)
0 to 25° C., 12 h; 72%
[1:1 dr]; 9:1 regiosel.
(20): 10s
1a (2.2 equiv) 2 (2 × 1 mol %)
THF:TFE (1:1)
25° C., 48 h; 71%
Converted to 10ss for X-ray

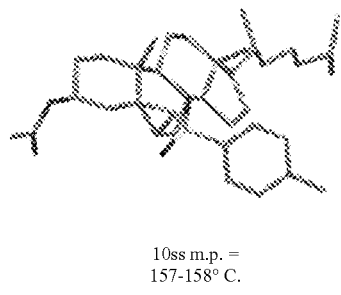

10ss m.p. = 157-158° C.

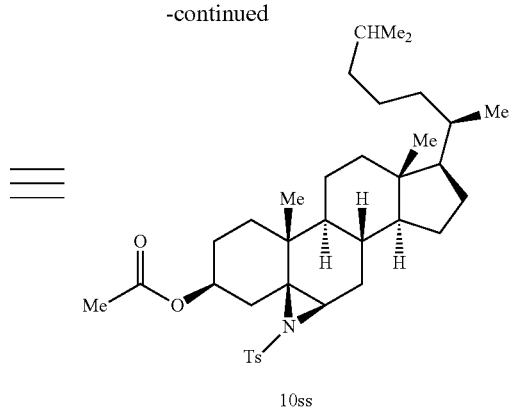

10ss temperatures are used, secondary processes (i.e., intramolecular annulation) that consume the initially formed N—H aziridines can dominate. Apparently, a fivefold increase in catalyst loading increased the rate of N—H aziridination sufficiently that it could take place rapidly at ambient temperature.

Cyclohexene 9n (entry 15) was aziridinated at room temperature to afford cyclic N—H aziridine 10n; no traces of allylic C—H amination (i.e., 1-amino-2-cyclohexene) could be detected by $^1$H-NMR analysis (≤2% sensitivity), in sharp contrast with other metal nitrene-based aziridination methods. Geraniol (9o, entry 16) and geranyl acetate (9q, entry 18), which incorporate two trisubstituted C=C double bonds, were N—H aziridinated regioselectivity, favoring the double bond at the $\Delta^{6,7}$-position over the $\Delta^{2,3}$-position in both cases.

Without wishing to be bound by any theory, the shift of the regioisomeric ratio from 1:5 in 10o to 1:14 in 10q suggests a subtle directing effect of the free allylic alcohol and/or an inductive deactivation by the acetate; perhaps the extent of H-bonding in the solvent also plays a role. Entry 17 stands as a testament to the extraordinarily mild reaction conditions as trisubstituted olefin 9p, which possesses a highly sensitive epoxy alcohol, was aziridinated rapidly and efficiently to epoxy N—H aziridine 10p in excellent yield. The transformation 9q→10q (entry 18) could be readily scaled up (6 mmol) with minimal erosion of the isolated yield to provide gram quantities of 10q. N—H aziridination of limonene 9r (entry 19) favored the trisubstituted ring double bond with 9:1 regioselectivity; however, the chiral center had no evident influence on the diastereoselectivity (1:1 dr, diastereomeric ratio). In contrast with the lack of stereoselectivity in 9i, cholesterol 9s (entry 20) exclusively yielded the β-N—H aziridine 10s in 71% yield; this unexpected stereochemical outcome, confirmed by single crystal x-ray analysis of 10ss (a crystalline derivative of 10s), suggests a directing effect by the adjacent C(3)-β-alcohol not observed in conformationally more mobile acyclic molecules such as 9i. The success with cholesterol and other natural products (7, 9h, 9i, 9o and 9r, Schemes 1B and 2) highlights the prospective utility of this method in the straightforward elaboration of molecules of biomedical interest (e.g., for $^{15}$N-labeling studies).

Next, we turned our attention to the direct N—H aziridination of di-, tri- and tetra-substituted styrenes and stilbene (entries 21-28, Scheme 3A). In general, styrenes were more reactive than aliphatic olefins, and often lower temperatures (−10 to 25° C.) were adequate. Conspicuously, cis-β-methyl styrene 1 id furnished the corresponding cis-2-Ph-3-Me N—H aziridine (12d, entry 24) without isomerization. Similarly, trans-β-methyl styrene 11c readily furnished trans-2-Ph-3-Me N—H aziridine (12c, entry 23) even on a 1- to 8-mmol scale. The N—H aziridine derived from 2-Me indene (12h, entry 28) was not isolated owing to its high reactivity, but instead reduced in situ to amine 12hh. Evaluation of the effect of catalyst loading on the reaction 11f→12f (entry 26) revealed the lowest practical loading of catalyst 2, without decreasing the isolated yield or drastically increasing the reaction time, was 0.5 mol %. This low catalyst loading renders the process economical and environmentally friendly. A further fivefold reduction in catalyst loading (from 0.5 mol to 0.1 mol %) resulted in a 25-fold increase in reaction time and a 30% drop in the isolated yield of 12f. Tetrasubstituted olefin 11g (entry 27) was easily N—H aziridinated at room temperature; 12g was isolated in 70% yield. The attempted direct N—H aziridination of 1-Ph-1-cyclopropylethene (11b) yielded only amino-oxyarylated product 12b. Without wishing to be bound to any particular theory, the complete lack of cyclopropane ring-opening products corroborate an aziridination pathway that does not involve long-lived radical or carbocation intermediates (see Scheme 4).

Scheme 3.

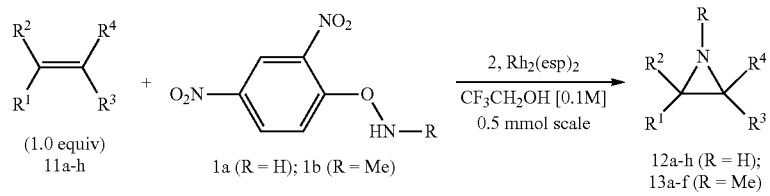

(1.0 equiv)
11a-h 1a (R = H); 1b (R = Me)

2, Rh$_2$(esp)$_2$
CF$_3$CH$_2$OH [0.1M]
0.5 mmol scale 12a-h (R = H);
13a-f (R = Me)

-continued

Structure of N—H and N—Me Aziridines
(Entry): Compound #; T (° C.), t (h), Isolated Yield (%), Regio- and diastereoselectivity [ratios]

A N—H Aziridination of di-, tri- and tetra-substituted styrenes:

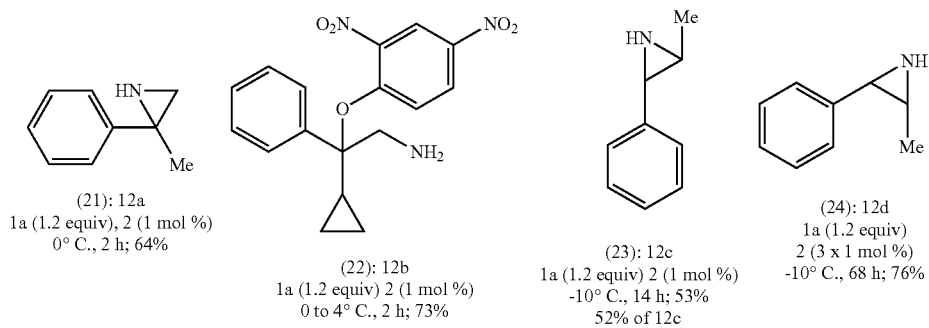

(21): 12a
1a (1.2 equiv), 2 (1 mol %)
0° C., 2 h; 64%

(22): 12b
1a (1.2 equiv) 2 (1 mol %)
0 to 4° C., 2 h; 73%

(23): 12c
1a (1.2 equiv) 2 (1 mol %)
-10° C., 14 h; 53%
52% of 12c (24): 12d
1a (1.2 equiv)
2 (3 x 1 mol %)
-10° C., 68 h; 76%

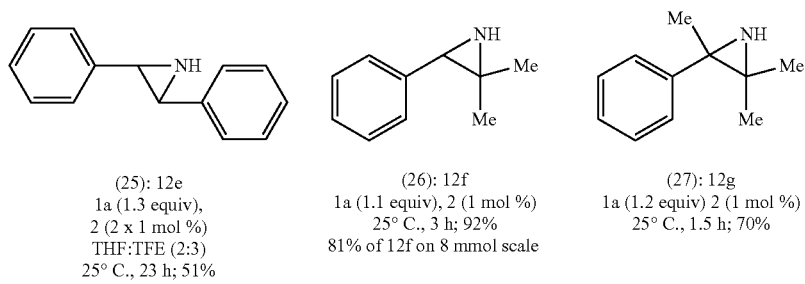

(25): 12e
1a (1.3 equiv),
2 (2 x 1 mol %)
THF:TFE (2:3)
25° C., 23 h; 51%

(26): 12f
1a (1.1 equiv), 2 (1 mol %)
25° C., 3 h; 92%
81% of 12f on 8 mmol scale (27): 12g
1a (1.2 equiv) 2 (1 mol %)
25° C., 1.5 h; 70%

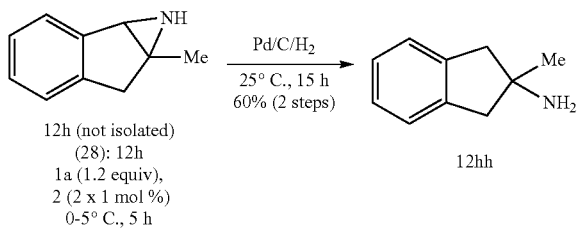

12h (not isolated)
(28): 12h
1a (1.2 equiv),
2 (2 x 1 mol %)
0-5° C., 5 h

Pd/C/H₂
25° C., 15 h
60% (2 steps)

12hh

B N—Me Aziridination of di- and tri-substituted aliphatic olefins and styrenes:

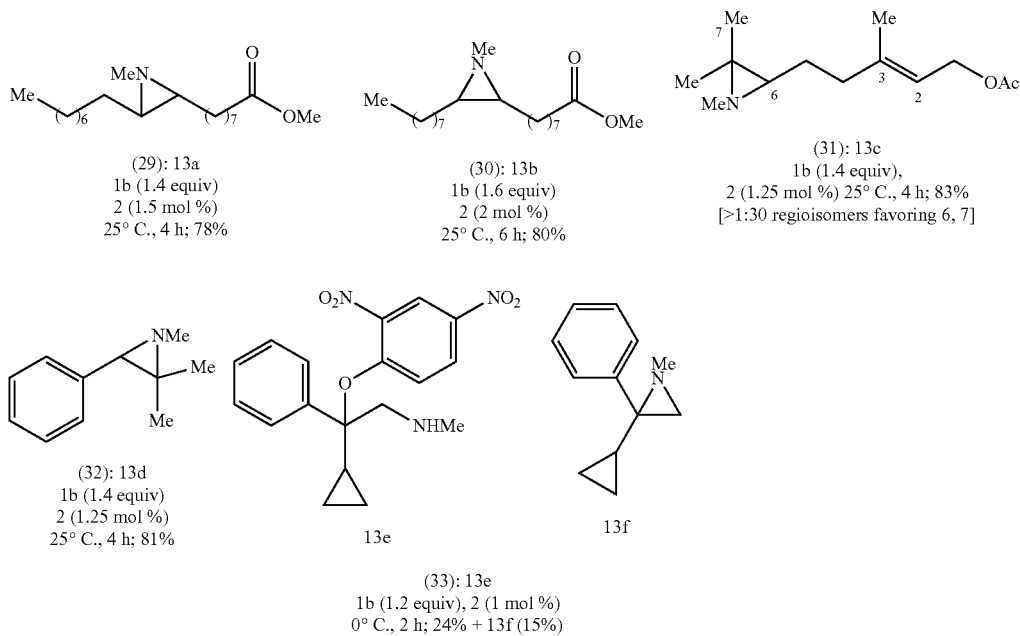

(29): 13a
1b (1.4 equiv)
2 (1.5 mol %)
25° C., 4 h; 78%

(30): 13b
1b (1.6 equiv)
2 (2 mol %)
25° C., 6 h; 80%

(31): 13c
1b (1.4 equiv),
2 (1.25 mol %) 25° C., 4 h; 83%
[>1:30 regioisomers favoring 6, 7]

(32): 13d
1b (1.4 equiv)
2 (1.25 mol %)
25° C., 4 h; 81%

13e

13f (33): 13e
1b (1.2 equiv), 2 (1 mol %)
0° C., 2 h; 24% + 13f (15%)

C Ring-opening transformations of N—H aziridines:

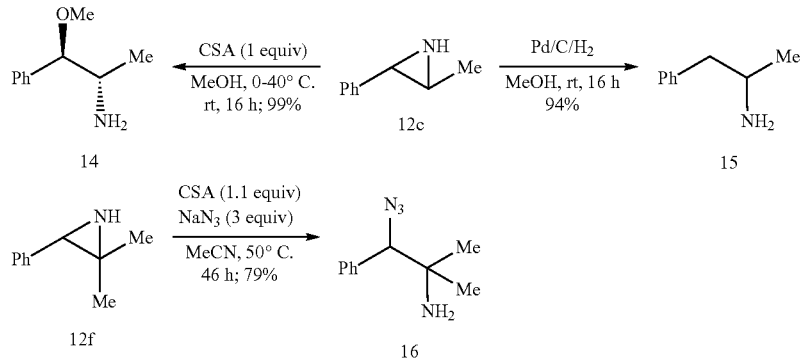

Scheme 4.

Pathway A: Rh-Nitrene

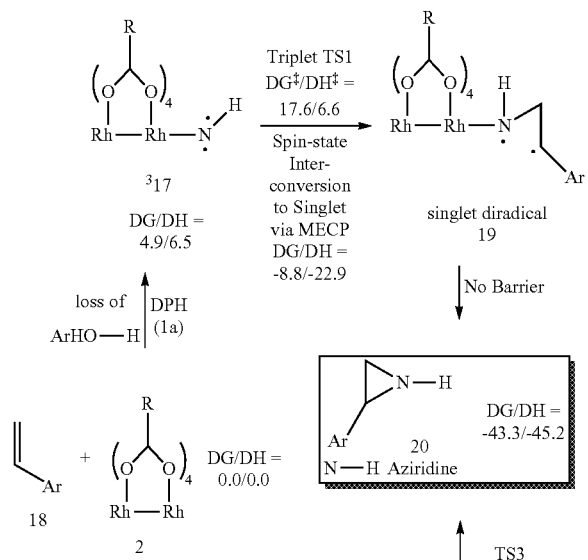

Pathway B: Rh-Amine

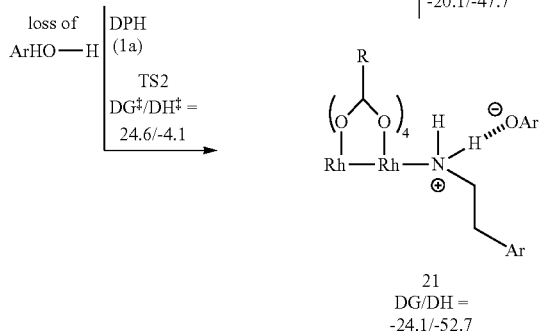

The practicality and broad scope of the preceding direct and stereospecific N—H aziridination of olefins (Schemes 2 and 3A) prompted an investigation of direct N-Me aziridination. Several di- and tri-substituted aliphatic olefin and styrene substrates (entries 29-33, Scheme 3B) were examined in the presence of 1b as the stoichiometric aminating agent and 1 to 2 mol % of catalyst 2. The N-Me aziridination of olefins also proceeded stereospecifically (entries 29 and 30) and, in the case of geraniol acetate 9q, the regioselectivity increased from 1:14 (in 10q) to >1:30 (in 13c), favoring the $\Delta^{6,7}$-olefin in both cases.

Two of the N—H aziridine products (12c and 12f) were subjected to ring-opening transformations (Scheme 3C). Upon catalytic hydrogenation, aziridine 12c afforded a 94% yield of amphetamine 15, the active pharmaceutical ingredient in Adderall™, an approved medication for attention deficit hyperactivity disorder as well as narcolepsy that is marketed as a mixture of enantiomers. Under acidic conditions, at slightly elevated temperature (40° C.) in MeOH, 12c was converted to O-Me-norephedrine 14 with complete regioselectivity and in nearly quantitative yield. Likewise, the ring-opening of trisubstituted N—H aziridine 12f with sodium azide furnished azidoamine 16 in 79% yield. These transformations by example illustrate how readily a nitrogen atom can be introduced into molecules.

We also examined prospective reaction mechanisms using quantum mechanical density-functional theory calculations (Scheme 4). Our (U)M06 calculations were carried out in Gaussian 09 using a polarizable conductor continuum solvent model for trifluoroethanol. Details of calculated transition states and intermediates are given in the supplementary materials.

We first examined plausible rhodium nitrene pathways. Generation of a rhodium nitrene intermediate is possible if the amino group of 1a coordinates to $Rh_2(esp)_2$ followed by loss of dinitrophenol (pathway A, Scheme 4). Calculations suggest that the triplet-spin state of the nitrene ($^3$17) is more than 8 kcal/mol lower in energy than the open-shell singlet, and reaction pathways identified on the triplet-spin energy surface were found to be lower in energy than reaction pathways on the singlet-spin energy surface. Because the $Rh_2(esp)_2$ catalyst and aziridine product have singlet-spin ground states, the reaction pathway must involve spin interconversion. The potential mechanism outlined in Scheme 4 provides a route for stereospecific aziridination if 17 reacts with alkenes by forming the first C—N bond via triplet transition state TS 1 followed by spin interconversion along the pathway to diradical intermediate 19 or fast spin interconversion at the diradical intermediate. After spin interconversion, the second C—N bond is formed by the coupling of singlet-paired electrons without a barrier and leads directly to aziridine 20.

As alternatives to nitrene pathways we also explored polar mechanisms involving Rh-amine and Rh-alkene coordination modes (see examples). One of several possible polar mechanisms is outlined as pathway B in Scheme 4. This pathway is akin to the mechanism proposed for amination of aryl boronic acids with 1a. Although this mechanism may account for amino-oxyarylated products (e.g., 4a and 4b) observed under some experimental conditions, the calculated barrier for this mechanism, as well as alternative polar mechanisms, is higher in energy than the nitrene mechanism presented in pathway A.

Solvents

Suitable solvents that may be used in the processes for making azirdines include polar, hydroxylic, and non-nucleophilic solvents. Examples of such solvents include from 2,2,2-trifluoroethanol, acetonitrile, water, methanol, ethanol, dichloromethane, tetrahydrofuran, and mixtures of the same. In some embodiments, the solvent is a mixture of up to 10% 2,2,2-trifluoroethanol and the balance of 90% or less made up of one of or more of acetonitrile, water, methanol, ethanol, dichloromethane, tetrahydrofuran.

Amination Agents

Suitable amination agents that may be used in the processes for making aziridines include hydroxylamines. More specifically, the hydroxylamine may be a compound of any one of formulas AA-1, AA-2, AA-3, AA-4, AA-5, AA-6, AA-7, and AA-8.

Compounds of Formulas AA-1, AA-2, and AA-3 include those where

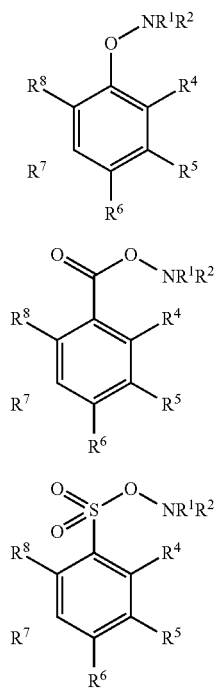

each $R^1$ and $R^2$ are independently selected from hydrogen, $C_1$-$C_{18}$ alkyl, $C_3$-$C_8$ cycloalkyl, —Si($R^3$)$_3$, allyl, aralkyl, substituted or unsubstituted aryl, and substituted or unsubstituted heteroaryl; wherein $R^1$ and $R^2$ can be connected to form a cyclic amine having from 4 to 7 carbocyclic ring members; and each $R^3$, when present, is independently selected from $C_1$-$C_{18}$ alkyl and substituted or unsubstituted aryl. each $R^4$, $R^5$, $R^6$, $R^7$, and $R^8$ are independently selected from hydrogen, nitro, fluoro, chloro, bromo, $C_1$-$C_{18}$ alkyl, $C_3$-$C_8$ cycloalkyl, arylsulfonyl, alkylsulfonyl, mono-/di-/tri-fluoroalkylsulfonyl, trifluoromethyl, $R^{16}R^{17}NC(O)$—, $R^{18}O_2C$—, $(R^{19})_4N^+$—, and $(R^{20})_2P(O)$—;

each $R^{16}$, $R^{17}$, $R^{18}$, $R^{19}$, $R^{20}$ is independently selected from H, $C_3$-$C_8$ cycloalkyl, substituted and unsubstituted aryl, substituted and unsubstituted heteroaryl, and $C_1$-$C_{18}$ alkyl; wherein the number of substituents for each substituted aryl may be from 1 to 5 and the number of substituents for each substituted heteroaryl may be from 1 to 4 and each substituent is independently selected from nitro, fluoro, chloro, methyl, ethyl, isopropyl, tert-butyl, arylsulfonyl, alkylsulfonyl, mono-/di-/tri-fluoroalkylsulfonyl, trifluoromethyl, $PEG_m$-.

Compounds of Formula AA-4 include those where

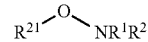

each $R^1$ and $R^2$ are independently selected from hydrogen, $C_1$-$C_{18}$ alkyl, $C_3$-$C_8$ cycloalkyl, —Si($R^3$)$_3$, allyl, aralkyl, aryl, and heteroaryl; wherein $R^1$ and $R^2$ can be connected to form a cyclic amine having from 4 to 7 carbocyclic ring members; and each $R^3$, when present, is independently selected from $C_1$-$C_{18}$ alkyl and aryl; and $R^{21}$ is $C_1$-$C_{18}$ alkyl substituted with an electron withdrawing group.

Compounds of Formula AA-5 include those where

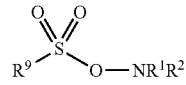

each $R^1$ and $R^2$ are independently selected from hydrogen, $C_1$-$C_{18}$ alkyl, $C_3$-$C_8$ cycloalkyl, —Si($R^3$)$_3$, allyl, aralkyl, aryl, and heteroaryl; wherein $R^1$ and $R^2$ can be connected to form a cyclic amine having from 4 to 7 carbocyclic ring members; and each $R^3$, when present, is independently selected from $C_1$-$C_8$ alkyl and aryl; each $R^4$, $R^5$, $R^6$, $R^7$, and $R^8$ are independently selected from hydrogen, nitro, fluoro, chloro, bromo, $C_1$-$C_{18}$ alkyl, $C_3$-$C_8$ cycloalkyl, arylsulfonyl, alkylsulfonyl, mono-/di-/tri-fluoroalkylsulfonyl, trifluoromethyl, $R^{16}R^{17}NC(O)$—, $R^{18}O_2C$—, $(R^{19})_4N^+$—, and $(R^{20})_2P(O)$—;

$R^9$ is selected from substituted and unsubstituted $C_1$-$C_{18}$ alkyl, $C_3$-$C_8$ cycloalkyl, and substituted and unsubstituted aryl.

Compounds of Formula AA-6 include those where

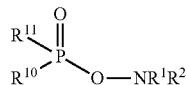

each $R^1$ and $R^2$ are independently selected from hydrogen, $C_1$-$C_{18}$ alkyl, $C_3$-$C_8$ cycloalkyl, —Si($R^3$)$_3$, allyl, aralkyl, substituted or unsubstituted aryl, and substituted or unsubstituted heteroaryl; wherein $R^1$ and $R^2$ can be connected to form a cyclic amine having from 4 to 7 carbocyclic ring members; and each $R^3$, when present, is independently selected from $C_1$-$C_{18}$ alkyl and aryl;

$R^{10}$ and $R^{11}$ are independently selected from substituted and unsubstituted aryl; wherein the number of substituents for substituted aryl may be from 1 to 5 and independently selected from nitro, fluoro, chloro, methyl, ethyl, isopropyl, tert-butyl, arylsulfonyl, alkylsulfonyl, mono-/di-/tri-fluoroalkylsulfonyl, trifluoromethyl, $R^{16}R^{17}NC(O)$—, $R^{18}O_2C$—, $(R^{19})_4N^+$—, $(R^{20})_2P(O)$—, $PEG_m$-, and o-furanyl.

Compounds of Formula AA-7 include those where

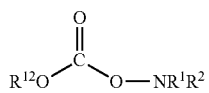

AA-7 each $R^1$ and $R^2$ are independently selected from hydrogen, $C_1$-$C_{18}$ alkyl, $C_3$-$C_8$ cycloalkyl, —$Si(R^3)_3$, allyl, aralkyl, substituted or unsubstituted aryl, and substituted or unsubstituted heteroaryl; wherein $R^1$ and $R^2$ can be connected to form a cyclic amine having from 4 to 7 carbocyclic ring members; and each $R^3$, when present, is independently selected from $C_1$-$C_{18}$ alkyl and aryl;

$R^{12}$ is selected from alkyl, cycloalkyl, alkenyl, cycloalkenyl, substituted and unsubstituted aryl; wherein the number of substituents for substituted aryl may be from 1 to 5 and independently selected from nitro, fluoro, chloro, methyl, ethyl, isopropyl, tert-butyl, arylsulfonyl, alkylsulfonyl, mono-/di-/tri-fluoroalkylsulfonyl, trifluoromethyl, $R^{16}R^{17}NC(O)$—, $R^{18}O_2C$—, $(R^{19})_4N^+$—, $(R^{20})_2P(O)$—, $PEG_m$-, and o-furanyl.

Compounds of Formula AA-8 include those where

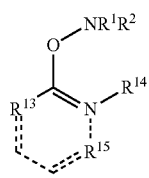

AA-8 each $R^1$ and $R^2$ are independently selected from hydrogen, $C_1$-$C_{18}$ alkyl, $C_3$-$C_8$ cycloalkyl, —$Si(R^3)_3$, allyl, aralkyl, substituted or unsubstituted aryl, and substituted or unsubstituted heteroaryl; wherein $R^1$ and $R^2$ can be connected to form a cyclic amine having from 4 to 7 carbocyclic ring members; and each $R^3$, when present, is independently selected from $C_1$-$C_8$ alkyl and aryl;

$R^{13}$ is selected from substituted and unsubstituted aryl, substituted and unsubstituted heteroaryl, alkyl/cycloalkyl, $CCl_3$, and $CF_3$, wherein the number of substituents for substituted aryl may be from 1 to 5 and wherein the number of substituents for substituted heteroaryl may be from 1 to 4 and each substituent is independently selected from nitro, fluoro, chloro, methyl, ethyl, isopropyl, tert-butyl, arylsulfonyl, alkylsulfonyl, mono-/di-/tri-fluoroalkylsulfonyl, trifluoromethyl, $R^{16}R^{17}NC(O)$—, $R^{18}O_2C$—, $(R^{19})_4N^+$—, and $(R^{20})_2P(O)$—, $PEG_m$-, and o-furanyl, or when $R^{13}$ forms an aromatic or other ring system with $R^{15}$, then $R^{13}$ is selected from O, N, and C—$R^{20}$;

$R^{14}$ is selected from H, substituted and unsubstituted aryl, $C_3$-$C_8$ cycloalkyl, and $C_1$-$C_{18}$ alkyl, wherein the number of substituents for substituted aryl may be from 1 to 5 and wherein the number of substituents for substituted heteroaryl may be from 1 to 4 and each substituent is independently selected from nitro, fluoro, chloro, methyl, ethyl, isopropyl, tert-butyl, arylsulfonyl, alkylsulfonyl, mono-/di-/tri-fluoroalkylsulfonyl, trifluoromethyl, $R^{16}R^{17}NC(O)$—, $R^{18}O_2C$—, $(R^{19})_4N^+$—, and $(R^{20})_2P(O)$—, $PEG_m$-, or when the nitrogen to which $R^{14}$ is substituted is part of an aromatic or other ring system, then $R^{14}$ may be absent or forms a salt with nitrogen to which it is substituted, and wherein when $R^{14}$ is substituted or unsubstituted aryl or $C_1$-$C_{18}$ alkyl, then the nitrogen is part of an iminium ion; and $R^{13}$ and $R^{15}$ do not form an aromatic or other ring system;

$R^{15}$ is selected from selected from substituted and unsubstituted aryl, $C_1$-$C_{18}$ alkyl, and $C_3$-$C_8$ cycloalkyl, wherein the number of substituents for substituted aryl may be from 1 to 5 and each substituent is independently selected from nitro, fluoro, chloro, methyl, ethyl, isopropyl, tert-butyl, arylsulfonyl, alkylsulfonyl, mono-/di-/tri-fluoroalkylsulfonyl, trifluoromethyl, $R^{16}R^{17}NC(O)$—, $R^{18}O_2C$—, $(R^{19})_4N^+$—, and $(R^{20})_2P(O)$—, $PEG_m$- or when $R^{15}$ forms an aromatic ring system with $R^{13}$, then $R^{15}$ is selected from N, CH, and C-alkyl.

In some embodiments, $R^1$ is hydrogen. In some embodiments, $R^1$ is $C_1$-$C_{18}$ alkyl. In some embodiments, $R^1$ is $C_3$-$C_8$ cycloalkyl. In some embodiments, $R^1$ is —$Si(R^3)_3$. In some embodiments, $R^1$ is allyl. In some embodiments, $R^1$ is aralkyl. In some embodiments, $R^1$ is aryl. In some embodiments, $R^1$ is heteroaryl. In some embodiments, $R^2$ is hydrogen. In some embodiments, $R^2$ is $C_1$-$C_{18}$ alkyl. In some embodiments, $R^2$ is $C_3$-$C_8$ cycloalkyl. In some embodiments, $R^2$ is —$Si(R^3)_3$. In some embodiments, $R^2$ is allyl. In some embodiments, $R^2$ is aralkyl. In some embodiments, $R^2$ is aryl. In some embodiments, $R^2$ is heteroaryl. In some embodiments, $R^1$ and $R^2$ can be connected to form a cyclic amine having from 4 to 7 carbocyclic ring members.

In some embodiments, $R^3$, when present, is $C_1$-$C_{18}$ alkyl. In some embodiments, $R^3$, when present, is aryl.

In some embodiments, $R^4$ is hydrogen. In some embodiments, $R^4$ is nitro. In some embodiments, $R^4$ is fluoro. In some embodiments, $R^4$ is chloro. In some embodiments, $R^4$ is bromo. In some embodiments, $R^4$ is $C_1$-$C_{18}$ alkyl. In some embodiments, $R^4$ is $C_3$-$C_8$ cycloalkyl. In some embodiments, $R^4$ is arylsulfonyl. In some embodiments, $R^4$ is alkylsulfonyl, In some embodiments, $R^4$ is mono-/di-/tri-fluoroalkylsulfonyl. In some embodiments, $R^4$ is trifluoromethyl. In some embodiments, $R^4$ is $R^{16}R^{17}NC(O)$—. In some embodiments, $R^4$ is $R^{18}O_2C$—. In some embodiments, $R^4$ is $(R^{19})_4N^+$—. In some embodiments, $R^4$ is and $(R^{20})_2P(O)$—.

In some embodiments, $R^5$ is hydrogen. In some embodiments, $R^5$ is nitro. In some embodiments, $R^5$ is fluoro. In some embodiments, $R^5$ is chloro. In some embodiments, $R^5$ is bromo. In some embodiments, $R^5$ is $C_1$-$C_{18}$ alkyl. In some embodiments, $R^5$ is $C_3$-$C_8$ cycloalkyl. In some embodiments, $R^5$ is arylsulfonyl. In some embodiments, $R^5$ is alkylsulfonyl. In some embodiments, $R^5$ is mono-/di-/tri-fluoroalkylsulfonyl. In some embodiments, $R^5$ is trifluoromethyl. In some embodiments, $R^5$ is $R^{16}R^{17}NC(O)$—. In some embodiments, $R^5$ is $R^{18}O_2C$—. In some embodiments, $R^5$ is $(R^{19})_4N^+$—. In some embodiments, $R^5$ is and $(R^{20})_2P(O)$—.

In some embodiments, $R^6$ is hydrogen. In some embodiments, $R^6$ is nitro. In some embodiments, $R^6$ is fluoro. In some embodiments, $R^6$ is chloro. In some embodiments, $R^6$ is bromo. In some embodiments, $R^6$ is $C_1$-$C_{18}$ alkyl. In some embodiments, $R^6$ is $C_3$-$C_8$ cycloalkyl. In some embodiments, $R^6$ is arylsulfonyl. In some embodiments, $R^6$ is alkylsulfonyl. In some embodiments, $R^6$ is mono-/di-/tri-fluoroalkylsulfonyl. In some embodiments, $R^6$ is trifluoromethyl. In some embodiments, $R^6$ is $R^{16}R^{17}NC(O)$—. In some embodiments, $R^6$ is $R^{18}O_2C$—. In some embodiments, $R^6$ is $(R^{19})_4N^+$—. In some embodiments, $R^6$ is and $(R^{20})_2P(O)$—.

In some embodiments, $R^7$ is hydrogen. In some embodiments, $R^7$ is nitro. In some embodiments, $R^7$ is fluoro. In some embodiments, $R^7$ is chloro. In some embodiments, $R^7$ is bromo. In some embodiments, $R^7$ is $C_1$-$C_{18}$ alkyl. In some embodiments, $R^7$ is $C_3$-$C_8$ cycloalkyl. In some embodiments, $R^7$ is arylsulfonyl. In some embodiments, $R^7$ is alkylsulfonyl. In some embodiments, $R^7$ is mono-/di-/tri-fluoroalkylsulfonyl. In some embodiments, $R^7$ is trifluoromethyl. In some embodiments, $R^7$ is $R^{16}R^{17}NC(O)$—. In some embodiments, $R^7$ is $R^{18}O_2C$—. In some embodiments, $R^7$ is $(R^{19})_4N^+$—. In some embodiments, $R^7$ is and $(R^{20})_2P(O)$—.

In some embodiments, $R^8$ is hydrogen. In some embodiments, $R^8$ is nitro. In some embodiments, $R^8$ is fluoro. In some embodiments, $R^8$ is chloro. In some embodiments, $R^8$ is bromo. In some embodiments, $R^8$ is $C_1$-$C_{18}$ alkyl. In some embodiments, $R^8$ is $C_3$-$C_8$ cycloalkyl. In some embodiments, $R^8$ is arylsulfonyl. In some embodiments, $R^8$ is alkylsulfonyl. In some embodiments, $R^8$ is mono-/di-/tri-fluoroalkylsulfonyl. In some embodiments, $R^8$ is trifluoromethyl. In some embodiments, $R^8$ is $R^{16}R^{17}NC(O)$—. In some embodiments, $R^8$ is $R^{18}O_2C$—. In some embodiments, $R^8$ is $(R^{19})_4N^+$—. In some embodiments, $R^8$ is and $(R^{20})_2P(O)$—.

In some embodiments, $R^{16}$ is H. In some embodiments, $R^{16}$ is $C_3$-$C_8$ cycloalkyl. In some embodiments, $R^{16}$ is substituted or unsubstituted aryl. In some embodiments, $R^{16}$ is substituted aryl. In some embodiments, $R^{16}$ is unsubstituted aryl. In some embodiments, $R^{16}$ is phenyl. In some embodiments, $R^{16}$ is substituted or unsubstituted heteroaryl. In some embodiments, $R^{16}$ is substituted heteroaryl. In some embodiments, $R^{16}$ is substituted heteroaryl. In some embodiments, $R^{16}$ is $C_1$-$C_{18}$ alkyl.

In some embodiments, $R^{17}$ is H. In some embodiments, $R^{17}$ is $C_3$-$C_8$ cycloalkyl. In some embodiments, $R^{17}$ is substituted or unsubstituted aryl. In some embodiments, $R^{17}$ is substituted aryl. In some embodiments, $R^{17}$ is unsubstituted aryl. In some embodiments, $R^{17}$ is phenyl. In some embodiments, $R^{17}$ is substituted or unsubstituted heteroaryl. In some embodiments, $R^{17}$ is substituted heteroaryl. In some embodiments, $R^{17}$ is substituted heteroaryl. In some embodiments, $R^{17}$ is $C_1$-$C_{18}$ alkyl.

In some embodiments, $R^{18}$ is H. In some embodiments, $R^{18}$ is $C_3$-$C_8$ cycloalkyl. In some embodiments, $R^{18}$ is substituted or unsubstituted aryl. In some embodiments, $R^{18}$ is substituted aryl. In some embodiments, $R^{18}$ is unsubstituted aryl. In some embodiments, $R^{18}$ is phenyl. In some embodiments, $R^{18}$ is substituted or unsubstituted heteroaryl. In some embodiments, $R^{18}$ is substituted heteroaryl. In some embodiments, $R^{18}$ is substituted heteroaryl. In some embodiments, $R^{18}$ is $C_1$-$C_{18}$ alkyl.

In some embodiments, $R^{19}$ is H. In some embodiments, $R^{19}$ is $C_3$-$C_8$ cycloalkyl. In some embodiments, $R^{19}$ is substituted or unsubstituted aryl. In some embodiments, $R^{19}$ is substituted aryl. In some embodiments, $R^{19}$ is unsubstituted aryl. In some embodiments, $R^{19}$ is phenyl. In some embodiments, $R^{19}$ is substituted or unsubstituted heteroaryl. In some embodiments, $R^{19}$ is substituted heteroaryl. In some embodiments, $R^{19}$ is substituted heteroaryl. In some embodiments, $R^{19}$ is $C_1$-$C_{18}$ alkyl.

In some embodiments, $R^{20}$ is H. In some embodiments, $R^{20}$ is $C_3$-$C_8$ cycloalkyl. In some embodiments, $R^{20}$ is substituted or unsubstituted aryl. In some embodiments, $R^{20}$ is substituted aryl. In some embodiments, $R^{20}$ is unsubstituted aryl. In some embodiments, $R^{20}$ is phenyl. In some embodiments, $R^{20}$ is substituted or unsubstituted heteroaryl. In some embodiments, $R^{20}$ is substituted heteroaryl. In some embodiments, $R^{20}$ is substituted heteroaryl. In some embodiments, $R^{20}$ is $C_1$-$C_{18}$ alkyl.

In some embodiments, $R^9$ is substituted or unsubstituted $C_1$-$C_{18}$ alkyl. In some embodiments, $R^9$ is unsubstituted $C_1$-$C_{18}$ alkyl. In some embodiments, $R^9$ is substituted $C_1$-$C_{18}$ alkyl. In some embodiments, $R^9$ is $C_3$-$C_8$ cycloalkyl. In some embodiments, $R^9$ is substituted or unsubstituted aryl. In some embodiments, $R^9$ is substituted aryl. In some embodiments, $R^9$ is unsubstituted aryl.

In some embodiments, $R^9$ is phenyl. In some embodiments, $R^9$ is mesityl. In some embodiments, $R^9$ is tolyl. In some embodiments, $R^9$ is brosyl. In some embodiments, $R^9$ is nosyl. In some embodiments, $R^9$ is p-fluorophenyl. In some embodiments, $R^9$ is 2,4,6-triisopropylphenyl.

In some embodiments, $R^{10}$ is substituted or unsubstituted aryl. In some embodiments, $R^{10}$ is substituted aryl. In some embodiments, $R^{10}$ is unsubstituted aryl. In some embodiments, $R^{11}$ is substituted or unsubstituted aryl. In some embodiments, $R^{11}$ is substituted aryl. In some embodiments, $R^{11}$ is unsubstituted aryl.

In some embodiments, $R^{12}$ is $C_1$-$C_{18}$ alkyl. In some embodiments, $R^{12}$ is $C_3$-$C_8$ cycloalkyl. In some embodiments, $R^{12}$ is $C_2$-$C_{18}$ alkenyl. In some embodiments, $R^{12}$ is $C_2$-$C_{18}$ cycloalkenyl. In some embodiments, $R^{12}$ is substituted or unsubstituted aryl. In some embodiments, $R^{12}$ is substituted aryl. In some embodiments, $R^{12}$ is unsubstituted aryl.

In some embodiments, $R^{13}$ is substituted and unsubstituted aryl. In some embodiments, $R^{13}$ is substituted aryl. In some embodiments, $R^{13}$ is unsubstituted aryl. In some embodiments, $R^{13}$ is substituted or unsubstituted heteroaryl. In some embodiments, $R^{13}$ is substituted heteroaryl. In some embodiments, $R^{13}$ is unsubstituted heteroaryl. In some embodiments, $R^{13}$ is $C_1$-$C_{18}$ alkyl. In some embodiments, $R^{13}$ is $C_3$-$C_8$ cycloalkyl. In some embodiments, $R^{13}$ is $CCl_3$. In some embodiments, $R^{13}$ is and $CF_3$.

In some embodiments, $R^{15}$ is substituted or unsubstituted aryl. In some embodiments, $R^{15}$ is substituted aryl. In some embodiments, $R^{15}$ is unsubstituted aryl. In some embodiments, $R^{15}$ is $C_1$-$C_8$ alkyl. In some embodiments, $R^{15}$ is $C_3$-$C_8$ cycloalkyl.

In some embodiments, $R^{13}$ and $R^{15}$ together with the carbon they substitute form an aromatic ring system and $R^{13}$ is selected from CH and N, and $R^{15}$ is selected from CH and N. In some embodiments, $R^{13}$ and $R^{15}$ together with the carbon they substitute form a partially unsaturated ring system having a total of six members and $R^{13}$ is selected from O, $CR^{20}$, and N, and $R^{15}$ is CH or $CH_2$.

In some embodiments, $R^{14}$ is H. In some embodiments, $R^{14}$ is substituted or unsubstituted aryl. In some embodiments, $R^{14}$ is substituted aryl. In some embodiments, $R^{14}$ is unsubstituted aryl. In some embodiments, $R^{14}$ is $C_3$-$C_8$ cycloalkyl. In some embodiments, $R^{14}$ is $C_1$-$C_{18}$ alkyl. In some embodiments when the nitrogen to which $R^{14}$ is substituted is part of an aromatic or other ring system, $R^{14}$ may be absent or forms a salt with the nitrogen to which it is substituted. In those situations, $R^{14}$ is selected from substituted or unsubstituted aryl and $C_1$-$C_{18}$ alkyl.

In embodiments having a substituted aryl, the number of substituents may from 1 to 5. In embodiments having substituted heteroaryl, the number of substituents may be from 1 to 4. Each substituent for substituted aryl and substituted heteroaryl is independently selected from nitro, fluoro, chloro, methyl, ethyl, isopropyl, tert-butyl, arylsulfonyl, alkylsulfonyl, mono-/di-/tri-fluoroalkylsulfonyl, trifluoromethyl, $PEG_m$-.

In some embodiments, compounds of Formula AA-8 are further characterized as a compound of any one of Formulas AA-8-1, AA-8-2, AA-8-3, AA-8-4, AA-8-5, and AA-8-6, where $R^1$, $R^2$, and $R^{14}$ are defined above and $X^-$ is a anionic counterion, for example fluoride, chloride, bromide, iodide, mesylate, triflate, tetrafuoroborate ($BF_4^-$), hexafluoro-antimonate ($SbF_6^-$), and tetra-pentafluorophenyl borate anion (BARF) and the like.

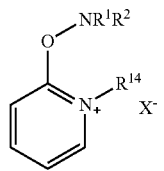

AA-8-1

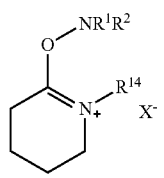

AA-8-2

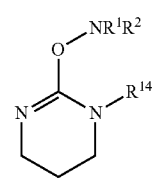

AA-8-3

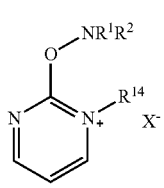

AA-8-4

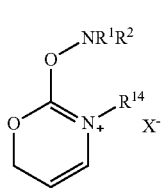

AA-8-5

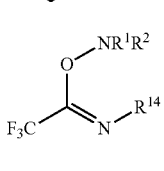

AA-8-2

In each of Formulas AA-1 through AA-8, each m, when present, is independently from 1 to 6; each $R^{16}, R^{17}, R^8, R^{19}, R^{20}$, when present, is independently selected from H, $C_3$-$C_8$ cycloalkyl, substituted and unsubstituted aryl, substituted and unsubstituted heteroaryl, and $C_1$-$C_{18}$ alkyl; wherein the number of substituents for each substituted aryl may be from 1 to 5 and the number of substituents for each substituted heteroaryl may be from 1 to 4 and each substituent is independently selected from nitro, fluoro, chloro, methyl, ethyl, isopropyl, tert-butyl, arylsulfonyl, alkylsulfonyl, mono-/di-/tri-fluoroalkylsulfonyl, trifluoromethyl, $PEG_m$-.

Catalyst

Suitable catalysts that may be used in the processes for making aziridines include transition metals. The transition metal may be selected from the first row of transition metals on the periodic table, for example copper. The transition metal may be selected from the second row of transition metals on the periodic table, for example rhodium. The transition metal may be selected from the third row of transition metals on the periodic table. The transition metal may be selected from the fourth row of transition metals on the periodic table.

In some embodiments, the transition metal is selected from cooper and rhodium. In some embodiments, the transition metal catalyst is copper. In some embodiments, the transition metal catalyst is copper I. In some embodiments, the transition metal catalyst is copper II. In some embodiments, the transition metal catalyst is rhodium. In some embodiments, the transition metal catalyst is dimeric rhodium.

In some embodiments, the transition metal catalyst may include one to ten ligands. In some embodiments, the number of ligands is one. In some embodiments, the number of ligands is two. In some embodiments, the number of ligands is three. In some embodiments, the number of ligands is four. In some embodiments, the number of ligands is five. In some embodiments, the number of ligands is six. In some embodiments, the number of ligands is seven. In some embodiments, the number of ligands is eight. In some embodiments, the number of ligands is nine. In some embodiments, the number of ligands is ten. The ligands may any aliphatic or arylalaphatic carboxylic acid that does not have an electron withdrawing group at the C-2 position (i.e. alpha position). Exemplary ligands include acetic acid, octanoic acid, and α,α,α',α'-tetramethyl-1,3-benzenedipropionic acid (esp). In some embodiments, the ligands are polypeptides of from 2-30 amino acids members made up from either natural or unnatural amino acids.

In some embodiments, the catalyst is selected from $Rh_2(OAc)_4$, $Rh_2(octanoate)_4$, and $Rh_2(esp)_2$. In some embodiments, the catalyst is $Rh_2(OAc)_4$.

In some embodiments, the ligands are chiral, for example when the polypeptide backbone is made up from chiral amino acid residues and the entire ligand, therefore, is homochiral. Other suitable chiral ligands include PTAD and DOSP. Chirality may also be imparted from one or more chiral axes and planar chirality, for example such as exists with ferrocene.

Olefins

Suitable olefins that may be used in the process of making azirdines include those of Formula O-1

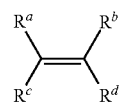

O-1 wherein each of $R_a$, $R_b$, $R_c$, $R_d$, is independently selected from H, substituted and unsubstituted aryl, $C_1$-$C_{18}$ alkyl, $C_3$-$C_8$ cycloalkyl, $C_2$-$C_{18}$ alkenyl, $C_3$-$C_8$ cycloalkenyl, and $C_2$-$C_{18}$ alkynyl.

Suitable olefins that may be used in the process of making azirdines include those of Formula O-2

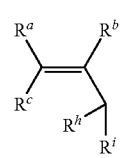

O-2 wherein each of $R_a$, $R_b$, $R_c$, $R_h$, and $R_i$ is independently selected from H, substituted and unsubstituted aryl, $C_1$-$C_{18}$ alkyl, $C_3$-$C_8$ cycloalkyl, $C_2$-$C_{18}$ alkenyl, $C_3$-$C_8$ cycloalkenyl, and $C_2$-$C_{18}$ alkynyl.

Suitable olefins may also be part of an aromatic system. In some embodiments, the olefin that may be used in the process of making azirdines include those of Formula O-3

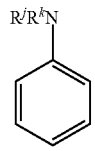

O-3 wherein Rj and Rk are independently selected from H, $C_1$-$C_{18}$ alkyl, and $C_3$-$C_8$ cycloalkyl.

In some embodiments, $R_a$ is H. In some embodiments, $R_a$ is substituted or unsubstituted aryl. In some embodiments, $R_a$ is substituted aryl. In some embodiments, $R_a$ is aryl. In some embodiments, $R_a$ is $C_1$-$C_{18}$ alkyl. In some embodiments, $R_a$ is $C_3$-$C_8$ cycloalkyl. In some embodiments, $R_a$ is $C_2$-$C_{18}$ alkenyl. In some embodiments, $R_a$ is $C_3$-$C_8$ cycloalkenyl. In some embodiments, $R_a$ is and $C_2$-$C_{18}$ alkynyl.

In some embodiments, $R_b$ is H. In some embodiments, $R_b$ is substituted or unsubstituted aryl. In some embodiments, $R_b$ is substituted aryl. In some embodiments, $R_b$ is aryl. In some embodiments, $R_b$ is $C_1$-$C_{18}$ alkyl. In some embodiments, $R_b$ is $C_3$-$C_8$ cycloalkyl. In some embodiments, $R_b$ is $C_2$-$C_{18}$ alkenyl. In some embodiments, $R_b$ is $C_3$-$C_8$ cycloalkenyl. In some embodiments, $R_b$ is and $C_2$-$C_{18}$ alkynyl.

In some embodiments, $R_c$ is H. In some embodiments, $R_c$ is substituted or unsubstituted aryl. In some embodiments, $R_c$ is substituted aryl. In some embodiments, $R_c$ is aryl. In some embodiments, $R_c$ is $C_1$-$C_{18}$ alkyl. In some embodiments, $R_c$ is $C_3$-$C_8$ cycloalkyl. In some embodiments, $R_c$ is $C_2$-$C_{18}$ alkenyl. In some embodiments, $R_c$ is $C_3$-$C_8$ cycloalkenyl. In some embodiments, $R_c$ is and $C_2$-$C_{18}$ alkynyl.

In some embodiments, $R_d$ is H. In some embodiments, $R_d$ is substituted or unsubstituted aryl. In some embodiments, $R_d$ is substituted aryl. In some embodiments, $R_d$ is aryl. In some embodiments, $R_d$ is $C_1$-$C_{18}$ alkyl. In some embodiments, $R_d$ is $C_3$-$C_8$ cycloalkyl. In some embodiments, $R_d$ is $C_2$-$C_{18}$ alkenyl. In some embodiments, $R_d$ is $C_3$-$C_8$ cycloalkenyl. In some embodiments, $R_d$ is and $C_2$-$C_{18}$ alkynyl.

In some embodiments, $R_h$ is H. In some embodiments, $R_h$ is substituted or unsubstituted aryl. In some embodiments, $R_h$ is substituted aryl. In some embodiments, $R_h$ is aryl. In some embodiments, $R_h$ is $C_1$-$C_{18}$ alkyl. In some embodiments, $R_h$ is $C_3$-$C_8$ cycloalkyl. In some embodiments, $R_h$ is $C_2$-$C_{18}$ alkenyl. In some embodiments, $R_h$ is $C_3$-$C_8$ cycloalkenyl. In some embodiments, $R_h$ is and $C_2$-$C_{18}$ alkynyl.

In some embodiments, $R_i$ is H. In some embodiments, $R_i$ is substituted or unsubstituted aryl. In some embodiments, $R_i$ is substituted aryl. In some embodiments, $R_i$ is aryl. In some embodiments, $R_i$ is $C_1$-$C_8$ alkyl. In some embodiments, $R_i$ is $C_3$-$C_8$ cycloalkyl. In some embodiments, $R_i$ is $C_2$-$C_{18}$ alkenyl. In some embodiments, $R_i$ is $C_3$-$C_8$ cycloalkenyl. In some embodiments, $R_i$ is and $C_2$-$C_{18}$ alkynyl.

In some embodiments, Rj is H. In some embodiments, Rj is $C_1$-$C_{18}$ alkyl. In some embodiments, Rj is $C_3$-$C_8$ cycloalkyl. In some embodiments, $R_k$ is H. In some embodiments, $R_k$ is $C_1$-$C_{18}$ alkyl. In some embodiments, $R_k$ is $C_3$-$C_8$ cycloalkyl.

Aziridine Products

Aziridines produced from practicing the aforementioned methods include those of Formula AP-1

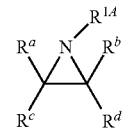

AP-1 where $R^{1A}$ and $R^{2A}$ are each independently selected from H, $C_1$-$C_{18}$ alkyl, $C_3$-$C_8$ cycloalkyl, and aralkyl;
wherein each of $R_a$, $R_b$, $R_c$, and $R_d$ is independently selected from H, substituted and unsubstituted aryl, $C_1$-$C_{18}$ alkyl, $C_3$-$C_8$ cycloalkyl, $C_2$-$C_{18}$ alkenyl, $C_3$-$C_8$ cycloalkenyl, and $C_2$-$C_{18}$ alkynyl.

Aziridines produced from practicing the aforementioned methods include those of Formula AP-2

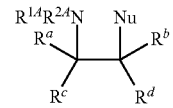

AP-2 where $R^{1A}$ and $R^{2A}$ are each independently selected from H, $C_1$-$C_{18}$ alkyl, $C_3$-$C_8$ cycloalkyl, and $C_1$-$C_{18}$ alkyl-aryl;
each of $R_a$, $R_b$, $R_c$, and $R_d$, is independently selected from H, substituted and unsubstituted aryl, $C_1$-$C_{18}$ alkyl, $C_3$-$C_8$ cycloalkyl, $C_2$-$C_{18}$ alkenyl, $C_3$-$C_8$ cycloalkenyl, and $C_2$-$C_{18}$ alkynyl;
Nu is selected from —$N_3$, —OH, —OR, halogen, and —OC(O)R, and heterocyclyl; R is selected from $C_1$-$C_{18}$ alkyl, and substituted or unsubstituted aryl.

Aziridines produced from practicing the aforementioned methods include those of Formula AP-3

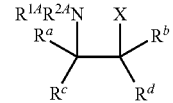

AP-3 where $R^{1A}$ and $R^{2A}$ are each independently selected from H, $C_1$-$C_{18}$ alkyl, $C_3$-$C_8$ cycloalkyl, and $C_1$-$C_{18}$ alkyl-aryl;
each of $R_a$, $R_b$, $R_c$, and $R_d$, is independently selected from H, substituted and unsubstituted aryl, $C_1$-$C_{18}$ alkyl, $C_3$-$C_8$ cycloalkyl, $C_2$-$C_{18}$ alkenyl, $C_3$-$C_8$ cycloalkenyl, and $C_2$-$C_{18}$ alkynyl; and
X is allyl or substituted or unsubstituted aryl.

Aziridines produced from practicing the aforementioned methods include those of Formula AP-4

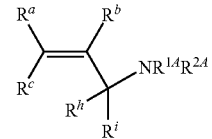

AP-4 where $R^{1A}$ and $R^{2A}$ are each independently selected from H, $C_1$-$C_{18}$ alkyl, $C_3$-$C_8$ cycloalkyl, and $C_1$-$C_{18}$ alkyl-aryl;
each of $R_a$, $R_b$, $R_c$ $R_h$, and $R_i$ is independently selected from H, substituted and unsubstituted aryl, $C_1$-$C_{18}$ alkyl, $C_3$-$C_8$ cycloalkyl, $C_2$-$C_{18}$ alkenyl, $C_3$-$C_8$ cycloalkenyl, and $C_2$-$C_{18}$ alkynyl.

Aziridines produced from practicing the aforementioned methods include those of Formula AP-5

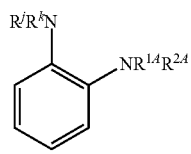

AP-5 where $R^{1A}$ and $R^{2A}$ are each independently selected from H, $C_1$-$C_{18}$ alkyl, $C_3$-$C_8$ cycloalkyl, and aralkyl;

each of Rj and Rk are independently selected from H, $C_1$-$C_8$ alkyl, and $C_3$-$C_8$ cycloalkyl.

In some embodiments, $R^{1A}$ is H. In some embodiments, $R^{1A}$ is $C_1$-$C_{18}$ alkyl. In some embodiments, $R^{1A}$ is $C_3$-$C_8$ cycloalkyl. In some embodiments, $R^{1A}$ is aralkyl. In some embodiments, $R^{2A}$ is H. In some embodiments, $R^{2A}$ is $C_1$-$C_{18}$ alkyl. In some embodiments, $R^{2A}$ is $C_3$-$C_8$ cycloalkyl. In some embodiments, $R^{2A}$ is aralkyl.

In some embodiments, $R_a$ is H. In some embodiments, $R_a$ is substituted or unsubstituted aryl. In some embodiments, $R_a$ is substituted aryl. In some embodiments, $R_a$ is aryl. In some embodiments, $R_a$ is $C_1$-$C_8$ alkyl. In some embodiments, $R_a$ is $C_3$-$C_8$ cycloalkyl. In some embodiments, $R_a$ is $C_2$-$C_{18}$ alkenyl. In some embodiments, $R_a$ is $C_3$-$C_8$ cycloalkenyl. In some embodiments, $R_a$ is and $C_2$-$C_{18}$ alkynyl.

In some embodiments, $R_b$ is H. In some embodiments, $R_b$ is substituted or unsubstituted aryl. In some embodiments, $R_b$ is substituted aryl. In some embodiments, $R_b$ is aryl. In some embodiments, $R_b$ is $C_1$-$C_{18}$ alkyl. In some embodiments, $R_b$ is $C_3$-$C_8$ cycloalkyl. In some embodiments, $R_b$ is $C_2$-$C_{18}$ alkenyl. In some embodiments, $R_b$ is $C_3$-$C_8$ cycloalkenyl. In some embodiments, $R_b$ is and $C_2$-$C_{18}$ alkynyl.

In some embodiments, $R_c$ is H. In some embodiments, $R_c$ is substituted or unsubstituted aryl. In some embodiments, $R_c$ is substituted aryl. In some embodiments, $R_c$ is aryl. In some embodiments, $R_c$ is $C_1$-$C_{18}$ alkyl. In some embodiments, $R_c$ is $C_3$-$C_8$ cycloalkyl. In some embodiments, $R_c$ is $C_2$-$C_{18}$ alkenyl. In some embodiments, $R_c$ is $C_3$-$C_8$ cycloalkenyl. In some embodiments, $R_c$ is and $C_2$-$C_{18}$ alkynyl.

In some embodiments, $R_d$ is H. In some embodiments, $R_d$ is substituted or unsubstituted aryl. In some embodiments, $R_d$ is substituted aryl. In some embodiments, $R_d$ is aryl. In some embodiments, $R_d$ is $C_1$-$C_{18}$ alkyl. In some embodiments, $R_d$ is $C_3$-$C_8$ cycloalkyl. In some embodiments, $R_d$ is $C_2$-$C_{18}$ alkenyl. In some embodiments, $R_d$ is $C_3$-$C_8$ cycloalkenyl. In some embodiments, $R_d$ is and $C_2$-$C_{18}$ alkynyl.

In some embodiments, $R_h$ is H. In some embodiments, $R_h$ is substituted or unsubstituted aryl. In some embodiments, $R_h$ is substituted aryl. In some embodiments, $R_h$ is aryl. In some embodiments, $R_h$ is $C_1$-$C_{18}$ alkyl. In some embodiments, $R_h$ is $C_3$-$C_8$ cycloalkyl. In some embodiments, $R_h$ is $C_2$-$C_{18}$ alkenyl. In some embodiments, $R_h$ is $C_3$-$C_8$ cycloalkenyl. In some embodiments, $R_h$ is and $C_2$-$C_{18}$ alkynyl.

In some embodiments, $R_i$ is H. In some embodiments, $R_i$ is substituted or unsubstituted aryl. In some embodiments, $R_i$ is substituted aryl. In some embodiments, $R_i$ is aryl. In some embodiments, $R_i$ is $C_1$-$C_{18}$ alkyl. In some embodiments, $R_i$ is $C_3$-$C_8$ cycloalkyl. In some embodiments, $R_i$ is $C_2$-$C_{18}$ alkenyl. In some embodiments, $R_i$ is $C_3$-$C_8$ cycloalkenyl. In some embodiments, $R_i$ is and $C_2$-$C_{18}$ alkynyl.

In some embodiments, Rj is H. In some embodiments, Rj is $C_1$-$C_{18}$ alkyl. In some embodiments, Rj is $C_3$-$C_8$ cycloalkyl. In some embodiments, $R_k$ is H. In some embodiments, $R_k$ is $C_1$-$C_{18}$ alkyl. In some embodiments, $R_k$ is $C_3$-$C_8$ cycloalkyl.

In some embodiments, Nu is —$N_3$. In some embodiments, Nu is —OH. In some embodiments, Nu is —OR. In some embodiments, Nu is halogen. In some embodiments, Nu is —OC(O)R. In some embodiments, Nu is heterocyclyl.

In some embodiments, R is $C_1$-$C_{18}$ alkyl. In some embodiments, R is substituted or unsubstituted aryl. In some embodiments, R is substituted aryl. In some embodiments, R is unsubstituted aryl.

In some embodiments, X is allyl. In some embodiments, X is substituted or unsubstituted aryl. In some embodiments, X is substituted aryl. In some embodiments, X is unsubstituted aryl.

The general reaction equations using olefins of formulas 0-1 to 0-3 to form aziridine products of formulas AP-1 to AP-5 are generally depicted in Scheme 5.

Scheme 5.

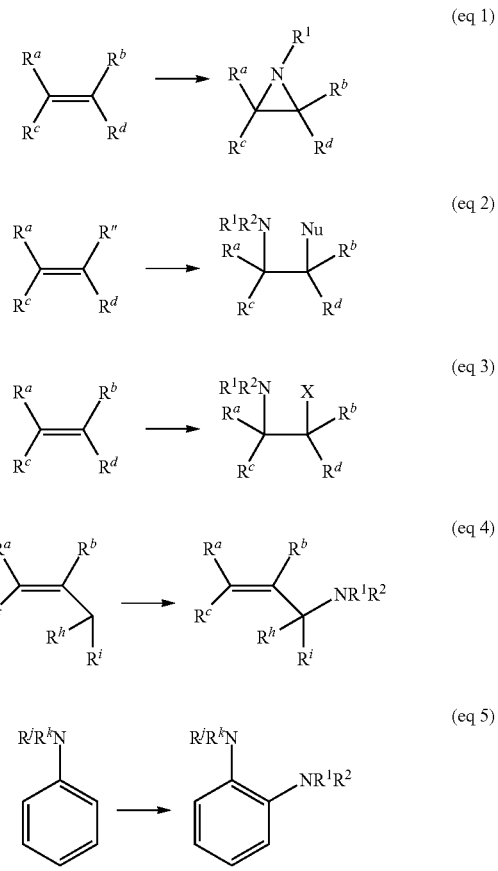

In another aspect, the amination agent and the olefin may be reacted in an intramolecular manner. That is, a chemical compound may possess an olefin and a group that may be activated into a hydroxylamine capable of aminating the olefin to form an aziridine. Such a compound, for example, may contain an amination functionality or a group capable of conversion into an amination functionality and an olefin functionality. As depicted in Scheme 6, compounds of Formula IM-1 include a substituted olefin where $R^{22}$ is selected from H, substituted and unsubstituted aryl, $C_1$-$C_{18}$ alkyl, $C_3$-$C_8$ cycloalkyl, $C_2$-$C_{18}$ alkenyl, $C_3$-$C_8$ cycloalkenyl, and $C_2$-$C_{18}$ alkynyl and n is an integer of from 1 to 16. The hydroxyl group in IM-1 is activated with a reagent such as phosgene to form the chloroformate of Formula IM-2. The chloroformate is reacted with hydroxylamine to form a hydroxylamine that is intrinsic to the olefin functionality. A transition metal catalyst is then added to form the aziridine intermediate of Formula IM-3 which subsequently undergoes decarboxylation resulting in the aziridine of Formula IM-4.

As may be apparent to the reader, the hydroxylamine added to the chloroformate IM-2 may be substituted with a variety of substituents such as one or two of substituted and unsubstituted aryl, $C_1$-$C_{18}$ alkyl, $C_3$-$C_8$ cycloalkyl, $C_2$-$C_{18}$ alkenyl, $C_3$-$C_8$ cycloalkenyl, and $C_2$-$C_{18}$ alkynyl. The resulting products would then have one or two substitutions on the aziridine nitrogen, respectively. In addition, the olefin may be substituted with a group selected from substituted and unsubstituted aryl, $C_1$-$C_{18}$ alkyl, $C_3$-$C_8$ cycloalkyl, $C_2$-$C_{18}$ alkenyl, $C_3$-$C_8$ cycloalkenyl, and $C_2$-$C_{18}$ alkynyl that is geminal to $R^{22}$ group and optionally further substituted with a group vicinal to $R^{22}$ selected from substituted and unsubstituted aryl, $C_1$-$C_{18}$ alkyl, $C_3$-$C_8$ cycloalkyl, $C_2$-$C_{18}$ alkenyl, $C_3$-$C_8$ cycloalkenyl, and $C_2$-$C_{18}$ alkynyl.

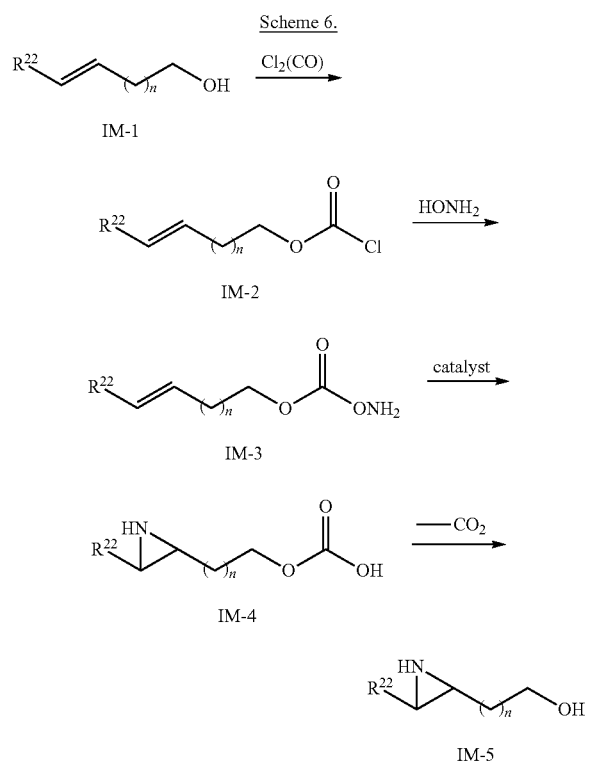

EXAMPLES

General Methods and Materials

Proton and carbon nuclear magnetic resonance spectra ($^1$H and $^{13}$C NMR) were recorded on a Varian 500 at 500 MHz and 126 MHz, respectively, or a Varian 400 at 400 MHz and 101 MHz, respectively, in $CDCl_3$ with TMS as internal standard, unless otherwise stated. $^1$H NMR data are reported as follows: chemical shift (ppm), multiplicity (s=singlet, br s=broad singlet, d=doublet, t=triplet, q=quartet, app q=apparent quartet, qn=quintet, app qn=apparent quintet, m=multiplet) and coupling constant (Hz). High resolution mass spectra (HRMS) were obtained using a Shimadzu IT-TOF mass spectrometer at UT Arlington. Infrared (IR) spectra were obtained using a Perkin Elmer Spectrum 1000 Fourier transform infrared spectrometer. Melting points were measured using an OptiMelt from Stanford Research Systems and are uncorrected. Analytical thin layer chromatography (TLC) used EMD Chemicals TLC silica gel 60 $F_{254}$ plates (0.040-0.063 mm) with visualization by UV light and/or $KMNO_4$ or phosphomolybdic acid (PMA) solution followed by heating. Chromatographic purifications utilized $Et_3N$ basified preparative TLC or flash chromatography using pre-packed $SiO_2$ columns on a CombiFlash Rf200 chromatograph (Teledyne Isco). Unless otherwise noted, yields refer to isolated, purified material with spectral data consistent with assigned structures or, if known, were in agreement with published data. All reactions were conducted under an argon atmosphere in oven-dried glassware with magnetic stirring. Reagents were purchased at the highest commercial quality and used without further purification, unless otherwise noted. Anhydrous acetonitrile and 2,2,2-trifluoroethanol (Aldrich Chem. Co.) were used directly. Tetrahydrofuran (THF) was dried on a Glass Contours Solvent System by passage through a column of activated, neutral alumina under argon before use. Amination reagents were obtained from Corvinus Chemicals and Rh catalysts from Sigma-Aldrich Chem. Co. and Strem Chemicals.

TABLE S1

Catalyst Screening

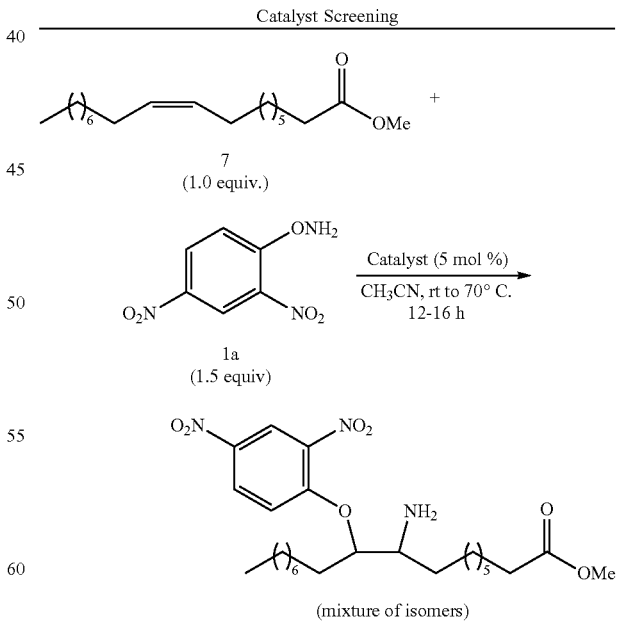

| Entry | Catalyst | Result[a] |
|---|---|---|
| 1 | Cu(CH$_3$CN)$_4$PF$_6$ | No reaction, 1a decomposed |
| 2 | FeCl$_3$ | No reaction, 1a decomposed |

TABLE S1-continued

| | | |
|---|---|---|
| 3 | Fe(II)OTf | No reaction, 1a decomposed |
| 4 | Mn(II)OTf | No reaction, 1a decomposed |
| 5 | $(C_5H_5)(CO)_2(THF)Fe(II)BF_4$ | No reaction, 1a decomposed |
| 6 | $Pd(OAc)_2$ | No reaction, 1a decomposed |
| 7 | $Rh_2(OAc)_4$ | 15% isolated product |

[a] Determined by NMR analysis of the crude reaction mixture.

TABLE S2

Catalyst Screening

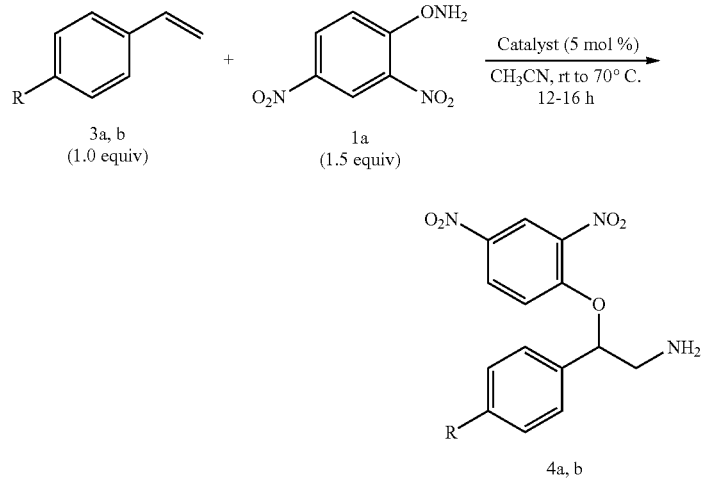

| Entry | Substrate | Catalyst | Result[a] |
|---|---|---|---|
| 1 | 3a | CuI | No reaction, 1a decomposed |
| 2 | 3a | CuBr | No reaction, 1a decomposed |
| 3 | 3a | $Cu(BF_4)2 \cdot H2O$ | No reaction, 1a decomposed |
| 4 | 3a | $Cu(acac)_2$ | No reaction, 1a decomposed |
| 5 | 3a | CuOTf | <10% of 4a |
| 6 | 3a | $Rh_2(OAc)_4$ | 25% product isolated |
| 7 | 3a | $Rh_2(TFA)_4$ | No reaction, 1a decomposed |
| 8 | 3a | $Rh_2(Hfb)_4$ | No reaction, 1a decomposed |
| 9 | 3a | $Rh_2(TPA)_4$ | No reaction, 1a decomposed |
| 10 | 3a | Hydroxy(COD)Rh(I)dimer | No reaction, 1a decomposed |
| 11 | 3a | Chloro(COD)Rh(I)dimer | No reaction, 1a decomposed |
| 12 | 3a | $Cl(CO)(Ph_3P)_2Rh(I)$ | No reaction, 1a decomposed |
| 13 | 3a | $Cl(Ph_3P)_3Rh(I)$ | No reaction, 1a decomposed |
| 14 | 3a | $(CO)_2(acac)_2Rh(I)$ | No reaction, 1a decomposed |
| 15 | 3a | $(Ph_3P)_3Rh(I)(CO)(H)$ | No reaction, 1a decomposed |
| 16 | 3a | $Rh(III)(acac)_3$ | No reaction, 1a decomposed |
| 17 | 3a | $Co_2(CO)_8$ | No reaction, 1a decomposed |
| 18 | 3b | $[(Cy_3P)_3(COD)(pyridine)Ir(I)]PF_6$ | No reaction, 1a decomposed |
| 19 | 3b | {Chloro(4,4-dicarboxy-2,2-bipyridine)(p-cymene) RuCl} | No reaction, 1a decomposed |
| 20 | 3b | $(COD)_2Ni(0)$ | No reaction, 1a decomposed |
| 21 | 3b | $[(MeO)(COD)Ir(I)]_2$ | No reaction, 1a decomposed |
| 22 | 3b | $Ir(III)Cl_3$ | No reaction, 1a decomposed |
| 23 | 3b | $Cl(Ph_3P)_3Au(I)$ | No reaction, 1a decomposed |
| 24 | 3b | $Au(III)Cl_3$ | No reaction, 1a decomposed |
| 25 | 3b | $(COD)(Ph_3P)_2Rh(I)PF_6 \cdot CH_2Cl_2$ | No reaction, 1a decomposed |
| 26 | 3b | 1,2-Bis[(2S,5S)-2,5-diethylphospholano]benzene(COD)Rh(I)OTf | No reaction, 1a decomposed |

[a] Determined by NMR analysis of the crude reaction mixture.

TABLE S3

Screening of Dirhodium Catalysts

| Entry | Substrate | Catalyst | Results[a]/Isolated Yield |
|---|---|---|---|
| 1 | 3a | $Rh_2(TFA)_4$ (5 mol %) | No reaction, 1a decomposed |
| 2 | 3a | $Rh_2(Hfb)_4$ (5 mol %) | No reaction, 1a decomposed |
| 3 | 3a | $Rh_2(TPA)_4$ (5 mol %) | No reaction, 1a decomposed |
| 4 | 3a | $Rh_2(OAc)_4$ (5 mol %) | 25% 4a |
| 5 | 3a | $Rh_2(octanoate)_4$ (5 mol %) | 36% 4a |
| 6 | 3a | $Rh_2(esp)_2$ (1 mol %) | 56% 4a |
| 7 | 3b | $Rh_2(OAc)_4$ (5 mol %) | 42% 4b |
| 8 | 3b | $Rh_2(esp)_2$ (1 mol %) | 75% 4b |

[a]Determined by NMR analysis of the crude reaction mixture.

General Amino-Oxyarylation Procedure $Rh_2(OAc)_4$ or $Rh_2(esp)_2$ (Du Bois' catalyst, 1-5 mol %) and aminating agent (1.5 equiv) were added to a stirring, rt solution of alkene (1.0 equiv) in dry $CH_3CN$ (0.1-0.5 M), unless otherwise specified. The reaction was stirred at the specified temperature and monitored by TLC. More catalyst and aminating agent were added, if required. After completion, the reaction mixture was diluted with EtOAc and washed once with 15% aqueous $NaHCO_3$ solution. The aqueous layer was extracted twice with EtOAc and the combined organic extracts were washed with brine, dried over $Na_2SO_4$, and concentrated in vacuo. The residue was purified on pre-packed $SiO_2$ columns using a CombiFlash chromatograph.

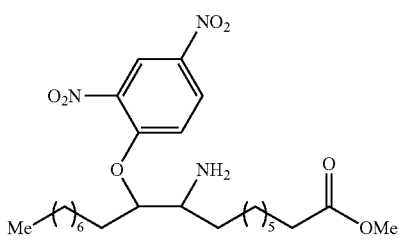

Methyl 9-amino-10-(2,4-dinitrophenoxy)octadecanoate/10-amino-9-(2,4-dinitrophenoxy)octadecanoate Following the general aminoaryloxylation procedure, methyl oleate 7 (10 mg, 34 μmol), aminating agent 1a (10 mg, 51 μmol), and $Rh_2(OAc)_4$ (0.8 mg, 1.7 μmol) were stirred in dry $CH_3CN$ (0.5 mL) at rt for 2 h, then at 60° C. for 10 h. Chromatographic purification of the crude product by preparative TLC using 40% EtOAc/hexanes as eluent afforded the title aminoaryloxylated regioisomers (1:1) as a viscous oil (2.5 mg, 15%). TLC: $R_f$ 0.5 (30% EtOAc/hexanes); $^1$H NMR (500 MHz, $CDCl_3$) δ 9.16 (d, J=2.7 Hz, 1H), 8.93 (dd, J=9.0, 2.4 Hz, 1H), 8.24 (dd, J=9.6, 2.7 Hz, 1H), 6.94 (dd, J=9.7, 3.5 Hz, 1H), 3.87-3.83 (m, 1H), 3.67 (s, 1.5H), 3.66 (s, 1.5H), 3.65-3.61 (m, 1H), 2.30 (t, J=7.4 Hz, 1H), 2.29 (t, J=7.4 Hz, 1H), 1.96 (br s, 1H), 1.80-1.77 (m, 1H), 1.76-1.14 (m, 30H), 0.87 (t, J=6.9 Hz, 1.5H), 0.86 (t, J=6.9 Hz, 1.5H); $^{13}$C NMR (101 MHz, $CDCl_3$) δ 174.25, 174.24, 148.68, 148.66, 135.58, 130.31, 130.25, 124.77, 114.06, 114.03, 72.17, 57.40, 57.31, 51.51, 51.49, 34.50, 34.44, 33.96, 33.93, 32.13, 32.06, 31.77, 29.54, 29.43, 29.42, 29.40, 29.25, 29.17, 29.15, 29.12, 29.03, 28.96, 28.86, 26.19, 26.04, 25.79, 25.65, 24.74, 22.62, 22.61, 14.07; HRMS (ESI$^+$) Calcd. for $[C_{25}H_{41}N_3O_7+Na]^+$ 518.2837. Found 518.2827.

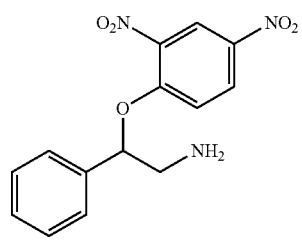

4a

2-(2,4-Dinitrophenoxy)-2-phenylethanamine

Following the general aminoaryloxylation procedure, styrene 3a (10 mg, 0.09 mmol), aminating agent 1a (27 mg, 0.135 mmol), and Rh$_2$(OAc)$_4$ (2.0 mg, 4.5 µmol) were stirred in dry CH$_3$CN (0.5 mL) at rt for 1 h, then at 60° C. for 2 h. Chromatographic purification of the crude product by PTLC using EtOAc/hexanes (1:1) as eluent afforded the title aminoaryloxylated product as a foamy solid (7 mg, 25%), mp 123.6-123.9° C. TLC; R$_f$ 0.5 (50% EtOAc/hexanes); $^1$H NMR (400 MHz, CDCl$_3$) δ 9.11-9.08 (m, 1H), 8.89 (br s, 1H), 8.20 (dd, J=9.4, 2.6 Hz, 1H), 7.52-7.31 (m, 5H), 6.89 (d, J=9.5 Hz, 1H), 5.07 (dd, J=7.7, 4.3 Hz, 1H), 3.72-3.56 (m, 2H); $^{13}$C NMR (101 MHz, CDCl$_3$) δ 148.33, 140.62, 136.08, 130.50, 130.19, 129.01, 128.82, 125.76, 124.27, 114.07, 72.42, 50.37; HRMS (ESI$^+$) Calcd. for [C$_{14}$H$_{13}$N$_3$O$_5$+Na]$^+$ 326.0747. Found 326.0741.

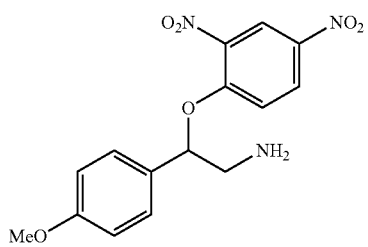

2-(2,4-Dinitrophenoxy)-2-(4-methoxyphenyl)ethanamine

Following the general aminoaryloxylation procedure, 4-methoxystyrene 3b (30 mg, 0.22 mmol), aminating agent 1a (66 mg, 0.33 mmol), and Rh$_2$(esp)$_2$ (1.7 mg, 2.2 µmol) were stirred in dry CH$_3$CN (1 mL) at rt for 3 h. Chromatographic purification of the crude product by PTLC using EtOAc/hexanes (40%) as eluent afforded the title aminoaryloxylated product as a solid (57 mg, 75%), mp 114.6° C. TLC: R$_f$=0.3 (40% EtOAc/hexanes); $^1$H NMR (500 MHz, CDCl$_3$) δ 9.16 (d, J=2.7 Hz, 1H), 8.90 (t, J=5.4 Hz, 1H), 8.25 (dd, J=9.5, 2.7 Hz, 1H), 7.38 (d, J=8.6 Hz, 2H), 6.97-6.91 (m, 3H), 5.08-5.02 (m, 1H), 3.84 (s, 3H), 3.73-3.55 (m, 2H), 2.20 (br s, 1H); $^{13}$C NMR (101 MHz, CD$_3$CN) δ 159.37, 148.66, 135.67, 133.92, 129.83, 127.29, 123.73, 117.38, 115.22, 113.75, 70.83, 54.93, 50.23; HRMS (ESI$^+$) Calcd. for [C$_{15}$H$_{15}$N$_3$O$_6$+Na]$^+$ 356.0853. Found 356.0846.

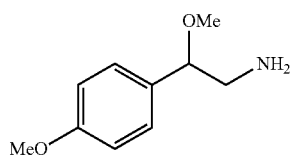

2-Methoxy-2-(4-methoxyphenyl)ethanamine

Following the general aminoaryloxylation procedure, 4-methoxystyrene 3b (68 mg, 0.5 mmol), aminating agent 1a (0.150 g, 0.75 mmol), and Rh$_2$(esp)$_2$ (19 mg, 25 µmol) were stirred in dry MeOH (1 mL) at rt for 4 h. Chromatographic purification of the crude product by CombiFlash using 5-10% MeOH/CH$_2$Cl$_2$ as eluent afforded the title aminomethoxylated product as a viscous liquid (52 mg, 56%) along with 4b (36 mg, 22%). TLC: R$_f$=0.3 (80% EtOAc/hexanes); $^1$H NMR (400 MHz, CDCl$_3$) δ 7.19 (d, J=8.6 Hz, 2H), 6.87 (d, J=8.7 Hz, 2H), 4.07 (dd, J=7.7, 4.3 Hz, 1H), 3.79 (s, 3H), 3.22 (s, 3H), 2.88 (dd, J=13.2, 7.7 Hz, 1H), 2.78 (dd, J=13.2, 4.4 Hz, 1H), 1.48 (br s, 2H); $^{13}$C NMR (101 MHz, CDCl$_3$) 159.21, 132.06, 127.91, 113.83, 85.30, 56.62, 55.23, 48.91; HRMS (ESI$^+$) Calcd. for [C$_{10}$H$_{15}$NO$_2$+Na]$^+$ 204.0995. Found 204.0991.

General N—H/N-Me Aziridination Procedure

A round bottom flask equipped with a magnetic stirrer was charged with alkene (0.5 mmol, 1.0 equiv) and CF$_3$CH$_2$OH (5 mL), unless otherwise specified. To this solution at the specified temperature were added Rh$_2$(esp)$_2$ (Du Bois' catalyst, 3.8 mg, 5 µmol, 1 mol %) and aminating agent 1a (or 1b) (0.119 g, 0.6 mmol, 1.2 equiv). The reaction was stirred at the specified temperature and monitored by TLC. More catalyst and aminating agent were added, if required. After completion, the reaction mixture was diluted with CH$_2$Cl$_2$ (10 mL) and washed once with 15% aqueous NaHCO$_3$ solution (5 mL). The aqueous layer was extracted twice with CH$_2$Cl$_2$ (10 mL) and the combined organic portions were washed once with brine (5 mL), dried over Na$_2$SO$_4$, and concentrated in vacuo. The residue was purified on pre-packed SiO$_2$ columns using a CombiFlash chromatograph.

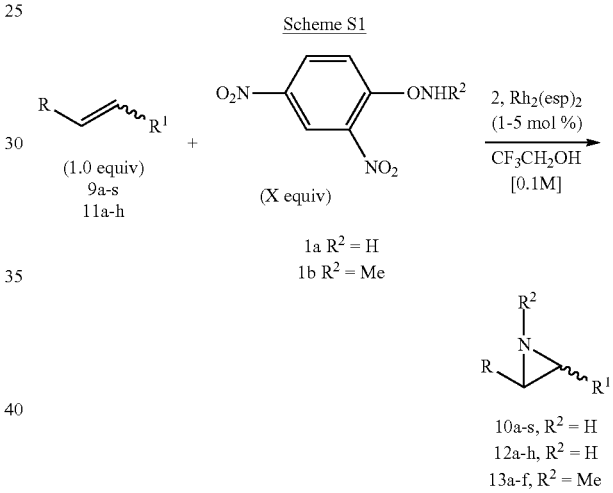

Scheme S1

Experimental

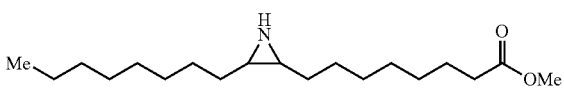

Methyl (Z)-8-(3-octylaziridine-2-yl)octanoate (42, 43) Following the general aziridination procedure, methyl oleate 7 (0.148 g, 0.5 mmol), aminating agent 1a (0.119 g, 0.6 mmol), and Rh$_2$(esp)$_2$ (3.8 mg, 5 µmol) were stirred in CF$_3$CH$_2$OH (5 mL) at rt for 3 h. Chromatographic purification of the crude product using 50-70% EtOAc/hexanes as eluent afforded the title aziridine as a viscous oil which solidified upon standing (0.130 g, 83%), mp 51.4-51.7° C. TLC: R$_f$=0.3 (60% EtOAc/hexanes); $^1$H NMR (400 MHz, CDCl$_3$) δ 3.63 (s, 3H), 2.27 (t, J=7.5 Hz, 2H), 1.93-1.90 (m, 2H), 1.66-1.53 (m, 2H), 1.49-1.19 (m, 25H), 0.85 (t, J=7.0 Hz, 3H); $^{13}$C NMR (101 MHz, CDCl$_3$) δ 174.24, 51.39, 34.94, 34.90, 34.05, 31.84, 29.60, 29.58, 29.37, 29.24, 29.21, 29.05, 28.87, 28.82, 28.04, 27.97, 24.89, 22.63, 14.07; HRMS (ESI$^+$) Calcd. for [C$_{19}$H$_{37}$NO$_2$+H]$^+$ 312.2897. Found 312.2887.

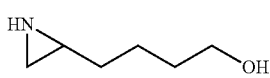

10a 4-(Aziridin-2-yl)butan-1-ol

Following the general aziridination procedure, hex-5-en-1-ol 9a (0.1 g, 1.0 mmol), aminating agent 1a (0.239 g, 1.2 mmol), and Rh$_2$(esp)$_2$ (38 mg, 50 μmol, 5 mol %) were stirred in CF$_3$CH$_2$OH (10 mL) at rt for 2 h. Chromatographic purification on a CombiFlash system using 10-15% MeOH/CH$_2$Cl$_2$ as eluent afforded the title aziridine as a viscous oil (68 mg, 59%). TLC: R$_f$~0.4 (20% MeOH/CH$_2$Cl$_2$); $^1$H NMR (500 MHz, CDCl$_3$) δ 3.59 (td, J=6.2, 1.7 Hz, 2H), 2.17 (br s, 2H), 1.97-1.94 (m, 1H), 1.77 (d, J=5.9 Hz, 1H), 1.68-1.39 (m, 5H), 1.42-1.27 (m, 2H); $^{13}$C NMR (126 MHz, CDCl$_3$) δ 62.01, 33.53, 32.27, 30.29, 25.02, 23.82; HRMS (ESI$^+$) Calcd. for [C$_6$H$_{13}$NO+H]$^+$ 116.1070. Found 116.1074.

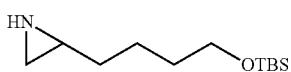

10b 2-(4-(tert-Butyldimethylsilyloxy)butyl)aziridine

Following the general aziridination procedure, tert-butyl (hex-5-en-1-yloxy)dimethylsilane(44) 9b (0.107 g, 0.5 mmol), aminating agent 1a (0.119 g, 0.6 mmol), and Rh$_2$(esp)$_2$ (19 mg, 25 μmol, 5 mol %) were stirred in CF$_3$CH$_2$OH (5 mL) at rt for 2 h. Chromatographic purification on a CombiFlash system using 2-3% MeOH/CH$_2$Cl$_2$ as eluent afforded the title aziridine as a viscous oil (83 mg, 72%). TLC: R$_f$~0.5 (10% MeOH/CH$_2$Cl$_2$); $^1$H NMR (500 MHz, CDCl$_3$) δ 3.61 (t, J=6.3 Hz, 2H), 1.95-1.91 (m, 1H), 1.75 (d, J=5.8 Hz, 1H), 1.62-1.34 (m, 6H), 1.32 (d, J=3.6 Hz, 1H), 0.88 (s, 9H), 0.04 (s, 6H); $^{13}$C NMR (101 MHz, CDCl$_3$) δ 63.07, 34.21, 32.58, 30.25, 25.93, 25.05, 23.85, 18.32, −5.32; HRMS (ESI) Calcd. for [C$_{12}$H$_{27}$NOSi+H]$^+$ 230.1935. Found 230.1934.

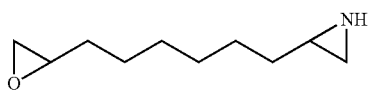

10c 2-(6-(Oxiran-2-yl)hexyl)aziridine

Following the general aziridination procedure, 2-(oct-7-en-1-yl)oxirane 9c (77 mg, 0.5 mmol), aminating agent 1a (0.199 g, 1.0 mmol), and Rh$_2$(esp)$_2$ (19 mg, 25 μmol) were stirred in CF$_3$CH$_2$OH (5 mL) at rt for 5 h. Chromatographic purification on a CombiFlash system gave the title aziridine as a viscous oil (65 mg, 77%). TLC: R$_f$ 0.5 (10% MeOH/CH$_2$Cl$_2$); $^1$H NMR (400 MHz, CDCl$_3$) δ 2.90-2.84 (m, 1H), 2.71 (dd, J=4.9, 4.2 Hz, 1H), 2.43 (dd, J=5.0, 2.7 Hz, 1H), 1.93-1.87 (m, 1H), 1.72 (d, J=5.8 Hz, 1H), 1.55-1.20 (m, 13H), 1.04 (br s, 1H); $^{13}$C NMR (101 MHz, CDCl$_3$) δ 52.33, 47.08, 34.33, 32.41, 30.32, 29.36, 29.33, 27.44, 25.88, 25.07; HRMS (ESI$^+$) Calcd. for [C$_{10}$H$_{19}$NO+H]$^+$ 170.1539. Found 170.1544.

10d (Z)-(3-(8-(tert-Butyldimethylsilyloxy)octyl)aziridin-2-yl)methanol

Following the general aziridination procedure, (Z)-11-(tert-butyldiphenylsilyloxy)undec-2-en-1-ol 9d (21 mg, 50 μmol), aminating agent 1a (12 mg, 60 μmol), and Rh$_2$(esp)$_2$ (0.4 mg, 0.5 μmol) were stirred in CF$_3$CH$_2$OH (0.5 mL) at rt. After 2 h, another portion of catalyst (0.4 mg, 0.5 μmol, 1 mol %) and aminating agent (12 mg, 60 μmol, 2 equiv) were added and the stirring was continued for an additional 1 h. Chromatographic purification via preparative TLC using 15% MeOH/CH$_2$Cl$_2$ as eluent afforded the title aziridine as a viscous oil (14 mg, 64%). TLC: R$_f$~0.4 (15% MeOH/CH$_2$Cl$_2$); $^1$H NMR (500 MHz, CDCl$_3$) δ 7.69-7.66 (m, 4H), 7.49-7.33 (m, 6H), 3.77 (dd, J=11.5, 4.9 Hz, 1H), 3.66 (t, J=6.5 Hz, 2H), 3.52 (dd, J=11.6, 7.1 Hz, 1H), 2.35 (br s, 1H), 2.15 (br s, 1H), 1.81 (br s, 2H), 1.55 (app qn, J=7.0 Hz, 2H), 1.51-1.17 (m, 12H), 1.05 (s, 9H); $^{13}$C NMR (101 MHz, CDCl$_3$) δ 135.55, 134.16, 129.45, 127.54, 63.98, 61.11, 35.42, 35.31, 32.56, 29.69, 29.55, 29.41, 29.30, 28.80, 27.98, 26.86, 25.74, 19.21; HRMS (ESI$^+$) Calcd. for [C$_{27}$H$_{41}$NO$_2$Si+H]$^+$ 440.2979. Found 440.2980.

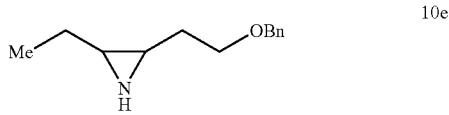 [SMILES: CCC1NC1CCOCc1ccccc1]

10e (Z)-2-(2-(Benzyloxy)ethyl)-3-ethylaziridine

Following the general aziridination procedure, (Z)-((hex-3-en-1-yloxy)methyl)benzene(45) 9e (38 mg, 0.2 mmol), aminating agent 1a (48 mg, 0.24 mmol), and Rh$_2$(esp)$_2$ (4.5 mg, 6 μmol, 3 mol %) were stirred in CF$_3$CH$_2$OH (2 mL) at rt for 36 h. The catalyst was added in three equal portions; the remaining two at intervals of 12 h after the initial addition. The crude aziridine was purified by Et$_3$N basified preparative TLC using EtOAc as eluent to afford the title aziridine as an oil (32 mg, 78%). TLC: R$_f$~0.2 (EtOAc); $^1$H NMR (500 MHz, CDCl$_3$) δ 7.36-7.33 (m, 3H), 7.32-7.22 (m, 2H), 4.54 (s, 2H), 3.64 (dd, J=7.0, 6.0 Hz, 2H), 2.26-2.13 (m, 1H), 2.20-1.90 (m, 1H), 1.85-1.78 (m, 1H), 1.64-1.57 (m, 1H), 1.44-1.38 (m, 2H), 1.26 (br s, 1H), 1.01 (t, J=7.4 Hz, 3H); $^{13}$C NMR (126 MHz, CDCl$_3$) δ 138.46, 128.37, 127.64, 127.55, 73.02, 68.93, 36.30, 32.20, 29.00, 22.07, 12.09; HRMS (ESI⁺) Calcd. for [$C_{13}H_{19}NO$+H]⁺ 206.1539. Found 206.1536.

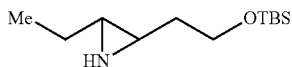

10f

(E)-2-(2-(tert-Butyldimethylsilyloxy)ethyl)-3-ethyl-aziridine

Following the general aziridination procedure, (E)-tert-butyl(hex-3-en-1-yloxy)dimethylsilane 9f (54 mg, 0.25 mmol), aminating agent 1a (60 mg, 0.3 mmol), and Rh₂(esp)₂ (1.9 mg, 2.5 μmol) were stirred in CF₃CH₂OH (2.5 mL) at rt for 4 h. Chromatographic purification of the crude product by Et₃N basified preparative TLC using 80% EtOAc/hexanes as eluent afforded the title aziridine as an oil (41 mg, 72%). TLC: $R_f$≈0.3 (80% EtOAc/hexanes); ¹H NMR (500 MHz, CDCl₃) δ 3.74 (t, J=6.2 Hz, 2H), 1.77 (br s, 1H), 1.69-1.63 (m, 2H), 1.62-1.53 (m, 1H), 1.51-1.37 (m, 2H), 1.00 (t, J=7.4 Hz, 3H), 0.90 (s, 9H), 0.07 (s, 6H); ¹³C NMR (126 MHz, CDCl₃) δ 61.49, 38.95, 37.21, 34.93, 27.21, 25.93, 18.30, 11.64, −5.34, −5.35; HRMS (ESI⁺) Calcd. for [$C_{12}H_{27}NOSi$+H]⁺ 230.1935. Found 230.1943.

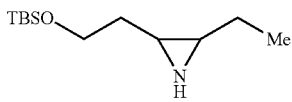

10g

(Z)-2-(2-(tert-Butyldimethylsilyloxy)ethyl)-3-ethyl-aziridine

Following the general aziridination procedure, (Z)-tert-butyl(hex-3-en-1-yloxy)dimethylsilane(46) 9g (43 mg, 0.2 mmol), aminating agent 1a (48 mg, 0.24 mmol), and Rh₂(esp)₂ (1.5 mg, 2 μmol) were stirred in CF₃CH₂OH (2 mL) at rt. After 24 h, more Rh-catalyst (1.5 mg, 2 μmol, 1 mol %) was added and the stirring was continued for another 5 h. Chromatographic purification of the crude product by Et₃N basified preparative TLC using 80% EtOAc/hexanes as eluent afforded the title aziridine as an oil (25 mg, 55%). TLC: $R_f$≈0.3 (80% EtOAc/hexanes); ¹H NMR (500 MHz, CDCl₃) δ 3.80-3.70 (m, 2H), 2.17 (br s, 1H), 2.00 (br s, 1H), 1.75-1.65 (m, 1H), 1.57-1.45 (m, 1H), 1.42 (app qn, J=7.2 Hz, 2H), 1.02 (t, J=7.4 Hz, 3H), 0.90 (s, 9H), 0.06 (s, 6H); ¹³C NMR (126 MHz, CDCl₃) δ 61.81, 36.34, 32.06, 31.85, 25.97, 22.15, 18.37, 12.13, −5.29; HRMS (ESI⁺) Calcd. for [$C_{12}H_{27}NOSi$+H]⁺ 230.1935. Found 230.1927.

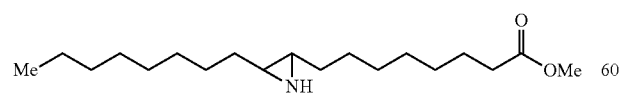

10h

Methyl E-8-(3-octylaziridine-2-yl)octanoate

Following the general aziridination procedure, methyl elaidate 9h (0.148 g, 0.5 mmol), aminating agent 1a (0.119 g, 0.6 mmol), and Rh₂(esp)₂ (3.8 mg, 5 μmol) were stirred in CF₃CH₂OH (5 mL) at rt for 2 h. Chromatographic purification of the crude product using 50-70% EtOAc/hexanes as eluent afforded the title aziridine as a viscous, reddish brown oil which solidified upon standing (0.142 g, 91%), mp 41.1-41.4° C. TLC: $R_f$≈0.3 (60% EtOAc/hexanes); ¹H NMR (500 MHz, CDCl₃) δ 3.62 (s, 3H), 2.26 (t, J=7.6 Hz, 2H), 1.60-1.54 (m, 4H), 1.43-1.15 (m, 25H), 0.84 (t, J=7.0 Hz, 3H); ¹³C NMR (101 MHz, CDCl₃) δ 174.20, 51.38, 37.74, 37.68, 34.34, 34.29, 34.02, 31.82, 29.53, 29.42, 29.22, 29.20, 29.16, 29.02, 27.63, 27.55, 24.86, 22.61, 14.05; HRMS (ESI⁺) Calcd. for [$C_{19}H_{37}NO_2$+H]⁺ 312.2897. Found 312.2886.

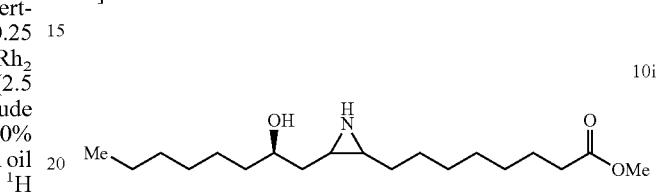

10i

Methyl (Z)-8-[3-(2R-hydroxyoctyl)aziridine-2-yl] octanoate

(43) Following the general aziridination procedure, methyl ricinoleate 9i (0.156 g, 0.5 mmol), aminating agent 1a (0.119 g, 0.6 mmol), and Rh₂(esp)₂ (11.4 mg, 15 μmol, 3 mol %) were stirred in CF₃CH₂OH (5 mL) at rt for 6 h. The catalyst was added in three equal portions at intervals of 2 h. Purification of the crude product using 5-10% MeOH/CH₂Cl₂ as eluent afforded the title aziridine as a viscous oil (0.135 g, 82%) obtained as a 1:1 mixture of diastereomers. TLC: $R_f$≈0.5 (10% MeOH/CH₂Cl₂); ¹H NMR (400 MHz, CDCl₃) δ 3.95-3.82 (m, 0.8H), 3.82-3.73 (m, 0.8H), 3.66 (s, 3H), 2.29 (t, J=7.5 Hz, 2H), 2.25-2.20 (m, 1H), 2.00-1.96 (m, 1H), 1.77-1.55 (m, 3H), 1.54-1.12 (m, 22H), 0.87 (t, J=7.1 Hz, 3H); ¹³C NMR (126 MHz, CDCl₃) δ 174.334, 174.326, 72.03, 71.10, 51.49, 37.74, 37.48, 34.54, 34.32, 34.07, 33.71, 33.49, 33.09, 31.87, 31.85, 31.34, 29.41, 29.38, 29.34, 29.30, 29.26, 29.24, 29.06, 28.79, 28.61, 27.79, 27.61, 25.86, 25.49, 24.91, 22.65, 22.64, 14.13, 14.12; HRMS (ESI⁺) Calcd. for [$C_{19}H_{37}NO_3$+Na]⁺ 350.2666. Found 350.2660.

The diastereomers were resolved via preparative TLC using MeOH/EtOAc (1:5):

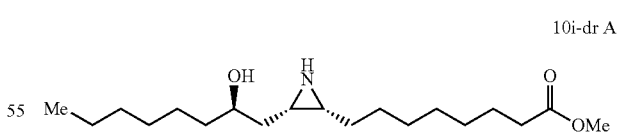

10i-dr A

Methyl 8-[3(S)-(2R-hydroxyoctyl)aziridine-2R-yl] octanoate

TLC: $R_f$≈0.5 (17% MeOH/EtOAc); ¹H NMR (500 MHz, CDCl₃) δ 3.84-3.80 (m, 1H), 3.67 (s, 3H), 2.31 (t, J=7.5 Hz, 2H), 2.27 (br s, 1H), 2.02 (br s, 1H), 1.71 (br s, 1H), 1.65-1.57 (m, 2H), 1.57-1.50 (m, 2H), 1.49-1.23 (m, 21H), 0.88 (t, J=7.1 Hz, 3H).

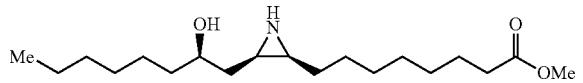

Methyl 8-[3R-(2R-hydroxyoctyl)aziridine-2(S)-yl]octanoate

TLC: $R_f$≈0.4 (17% MeOH/EtOAc); $^1$H NMR (500 MHz, CDCl$_3$) δ 3.92-3.84 (m, 1H), 3.68 (s, 3H), 2.31 (t, J=7.5 Hz, 2H), 2.26 (br s, 1H), 2.00 (br s, 1H), 1.80-1.72 (m, 1H), 1.67-1.60 (m, 2H), 1.54-1.17 (m, 23H), 0.89 (t, J=7.1H, 3H).

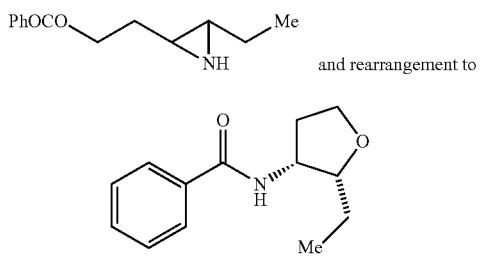

and rearrangement to (E)-2-(3-Ethylaziridine-2-yl)ethyl benzoate and Rearrangement Product (Z)—N-(2-ethyltetrahydrofuran-3-yl)benzamide Following the general aziridination procedure, (E)-hex-3-en-1-yl benzoate(47) 9j (0.102 g, 0.5 mmol), aminating agent 1a (0.119 g, 0.6 mmol), and Rh$_2$(esp)$_2$ (3.8 mg, 5 μmol) were stirred in CF$_3$CH$_2$OH (5 mL) at rt for 1 h. Chromatographic purification of the crude product using a CombiFlash with 50-70% EtOAc/hexanes as eluent afforded the title aziridine as a reddish brown oil (95 mg, 86%) along with 10jj, obtained as a yellow oil (5 mg, 4%), arising from O→N benzoate migration followed by S$_N$2 addition of the oxygen to the now activated aziridine.

(E)-2-(3-ethylaziridine-2-yl)ethyl benzoate

TLC: $R_f$≈0.3 (EtOAc); $^1$H NMR (500 MHz, CDCl$_3$) δ 8.09-7.98 (m, 2H), 7.62-7.51 (m, 1H), 7.51-7.36 (m, 2H), 4.53-4.35 (m, 2H), 1.95-1.76 (m, 3H), 1.70 (td, J=6.1, 2.5 Hz, 1H), 1.56-1.29 (m, 2H), 0.98 (t, J=7.4 Hz, 3H); $^{13}$C NMR (126 MHz, CDCl$_3$) δ 166.51, 132.91, 130.21, 129.52, 128.34, 63.40, 39.07, 34.44, 33.47, 27.29, 11.61; HRMS (ESI$^+$) Calcd. for [C$_{13}$H$_{17}$NO$_2$+H]$^+$ 220.1332. Found 220.1334; IR (neat) 3297, 3220, 2963, 1718 cm$^1$.

(Z)—N-(2-ethyltetrahydrofuran-3-yl)benzamide

TLC: $R_f$≈0.5 (EtOAc); $^1$H NMR (500 MHz, CDCl$_3$) δ 7.89-7.80 (m, 2H), 7.45-7.26 (m, 3H), 4.80 (ddd, J=10.7, 9.2, 3.1 Hz, 1H), 4.07 (td, J=9.1, 5.5 Hz, 1H), 3.88-3.80 (m, 2H), 1.95-1.68 (m, 2H), 1.68-1.40 (m, 3H), 1.05 (t, J=7.3 Hz, 3H); $^{13}$C NMR (126 MHz, CDCl$_3$) δ 162.43, 131.26, 128.29, 128.11, 127.96, 80.29, 69.97, 60.63, 32.05, 23.74, 11.85; HRMS (ESI$^-$) Calcd. for [C$_{13}$H$_{17}$NO$_2$—H]$^-$ 218.1187. Found 218.1180; IR (neat) 3280, 2959, 2937, 1646 cm$^1$.

Structure Confirmed by nOe:

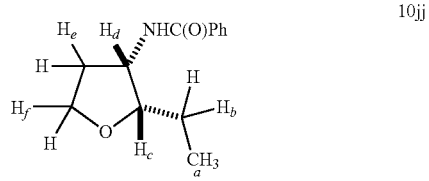

Irradiation (saturation) of proton d (H$_d$) leads to the enhancement of the protons e (H$_e$) and c (H$_e$). Protons a and b (H$_a$ and H$_b$) of ethyl group are completely suppressed.

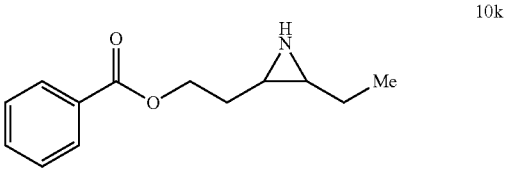 [SMILES: CCC1NC1CCOC(=O)c1ccccc1]

(Z)-2-(3-Ethylaziridine-2-yl)ethyl benzoate

Following the general aziridination procedure, (Z)-hex-3-en-1-yl benzoate(47) 9k (0.102 g, 0.5 mmol), aminating agent 1a (0.119 g, 0.6 mmol), and Rh$_2$(esp)$_2$ (19 mg, 25 μmol, 5 mol %) were stirred in CF$_3$CH$_2$OH (5 mL) at rt for 2 h. Chromatographic purification on a CombiFlash system using 70-90% EtOAc/hexanes as eluent afforded the title aziridine as a viscous oil (76 mg, 69%). TLC: $R_f$≈0.3 (EtOAc); $^1$H NMR (400 MHz, CDCl$_3$) δ 8.06-8.03 (m, 2H), 7.57-7.53 (m, 1H), 7.45-7.41 (m, 2H), 4.47 (t, J=6.4 Hz, 2H), 2.22 (app q, J=6.4 Hz, 1H), 2.05 (app q, J=6.7 Hz, 1H), 2.01-1.92 (m, 2H), 1.82-1.73 (m, 1H), 1.45 (app qn, J=7.3 Hz, 2H), 1.03 (t, J=7.4 Hz, 3H); 13C NMR (101 MHz, CDCl$_3$) δ 166.59, 132.91, 130.25, 129.54, 128.34, 63.67, 36.38, 32.05, 28.10, 21.93, 12.04. HRMS (ESI$^+$) Calcd. for [C$_{13}$H$_{17}$NO$_2$+H]$^+$ 220.1332. Found 220.1336.

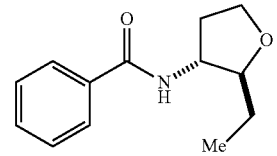

(E)-N-(2-Ethyltetrahydrofuran-3-yl)benzamide

Aminating agent 1a (0.119 g, 0.6 mmol) was added to a stirring, rt solution of (Z)-hex-3-en-1-yl benzoate 9k (0.102 g, 0.5 mmol) and Rh$_2$(esp)$_2$ (3.8 mg, 5 μmol) in CF$_3$CH$_2$OH (5 mL). After 16 h, the temperature was raised to 50° C. Following another 9 h at this higher temperature, more Rh-catalyst (3.8 mg, 5 μmol, 1 mol %) was added. Thereafter, two more portions of catalyst (3.8 mg) were added every 24 h. The substrate was completely consumed after a total of 96 h. The reaction mixture was then cooled to rt, diluted with CH$_2$Cl$_2$ (10 mL), and washed with 15% aqueous NaHCO$_3$ solution (5 mL). The layers were separated and the aqueous layer was extracted with fresh CH$_2$Cl$_2$ (10 mL×2). The combined organic extracts were washed with brine (5 mL), dried over Na$_2$SO$_4$, and concentrated. Chromatographic purification of the residue on a CombiFlash system to afforded the title tetrahydrofuran as a viscous liquid (92 mg, 84%). TLC: R$_f$=0.3 (60% EtOAc/hexanes); $^1$H NMR (500 MHz, CDCl$_3$) δ 7.99-7.88 (m, 2H), 7.52-7.44 (m, 1H), 7.44-7.35 (m, 2H), 4.49 (ddd, J=8.8, 6.4, 4.1 Hz, 1H), 3.92-3.74 (m, 3H), 2.86 (br s, 1H), 2.00-1.81 (m, 2H), 1.80-1.53 (m, 2H), 0.99 (t, J=7.4 Hz, 3H); $^{13}$C NMR (126 MHz, CDCl$_3$) δ 162.68, 131.35, 128.26, 128.19, 127.79, 81.84, 73.24, 59.14, 38.40, 28.34, 9.82; HRMS (ESI$^+$) Calcd. for [C$_{13}$H$_{17}$NO$_2$+H]$^+$ 220.1332. Found 220.1325; IR (neat) 3286, 2961, 2933, 1644 cm$^1$.

Structure Confirmed by nOe:

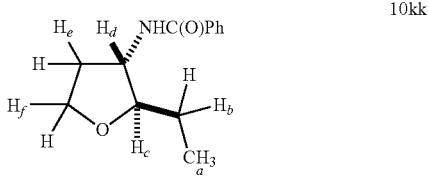

10kk

Irradiation (saturation) of proton d (H$_d$) leads to the enhancement of the proton e (H$_e$) and protons a and b (H$_a$ and H$_b$) of ethyl group.

10l (E)-2-(3-Ethylaziridine-2-yl)ethyl acetate

Following the general aziridination procedure, (E)-hex-3-en-1-yl acetate(48) 91 (0.1 g, 0.7 mmol), aminating agent 1a (0.167 g, 0.84 mmol), and Rh$_2$(esp)$_2$ (5.3 mg, 7 μmol) were stirred in CF$_3$CH$_2$OH (7 mL) at rt for 1.5 h. Chromatographic purification on a CombiFlash system using 70-90% EtOAc/hexanes as eluent afforded the title aziridine as an oil (91 mg, 83%). TLC: R$_f$=0.3 (90% EtOAc/hexanes); $^1$H NMR (500 MHz, CDCl$_3$) δ 4.17-4.13 (m, 2H), 2.02 (s, 3H), 1.76-1.58 (m, 4H), 1.49-1.40 (m, 1H), 1.38-1.30 (m, 1H), 0.96 (t, J=7.4 Hz, 3H), 0.41 (br s, 1H); $^{13}$C NMR (126 MHz, CDCl$_3$) δ 171.06, 62.89, 39.00, 34.33, 33.22, 27.28, 20.96, 11.61; HRMS (ESI$^+$) Calcd. for [C$_8$H$_{15}$NO$_2$+H] 158.1176. Found 158.1170; IR (neat) 3297, 3222, 2964, 1739 cm$^1$.

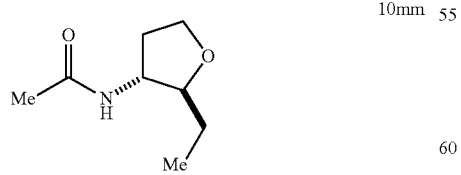

10mm (E)-N-(2-Ethyltetrahydrofuran-3-yl)acetamide

A mixture of (Z)-hex-3-en-1-yl acetate(48) 9m (0.124 g, 0.87 mmol), aminating agent 1a (0.208 g, 1.04 mmol), and Rh$_2$(esp)$_2$ (6.6 mg, 1 mol %) was stirred at rt in CF$_3$CH$_2$OH (8 mL). Three additional portions of catalyst (6.6 mg, 1 mol %) were added every 12 h thereafter for a total of 26.4 mg (35 μmol, 4 mol %). After a total of 51 h, the reaction mixture was quenched and chromatographically purified on a CombiFlash system using 80-100% EtOAc/hexanes as eluent to afford the title tetrahydrofuran as a viscous oil (84 mg, 61%) obtained as a mixture of diastereomers (>95:5). TLC: R$_f$=0.3 (80% EtOAc/hexanes); $^1$H NMR (400 MHz, CDCl$_3$) (major diastereomer) δ 4.23 (ddd, J=8.7, 6.7, 4.3 Hz, 1H), 3.77-3.67 (m, 2H), 3.58-3.50 (m, 1H), 3.19 (br s, 1H), 1.92 (s, 3H), 1.87-1.68 (m, 2H), 1.63-1.37 (m, 2H), 0.90 (t, J=7.5 Hz, 3H); $^{13}$C NMR (101 MHz, CDCl$_3$) δ 163.98, 82.16, 72.85, 58.89, 38.28, 28.28, 14.04, 9.84; HRMS (ESI$^+$) Calcd. for [C$_8$H$_{15}$NO$_2$+H]$^+$ 158.1176. Found 158.1173; IR (neat) 3272, 2963, 2935, 1668 cm$^1$.

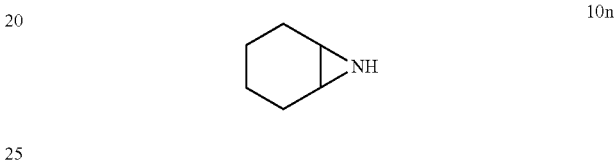

10n

7-Azabicyclo[4.1.0]heptanes

(49) Following the general aziridination procedure, cyclohexene 9n (41 mg, 0.5 mmol), aminating agent 1a (0.119 g, 0.6 mmol), and Rh$_2$(esp)$_2$ (3.8 mg, 5 μmol) were stirred in CF$_3$CH$_2$OH (5 mL) at rt for 3 h. Chromatographic purification on a CombiFlash system using 60-70% EtOAc/hexanes as eluent to give the title aziridine as an oil (34 mg, 71%). TLC: R$_f$=0.3 (80% EtOAc/hexanes); $^1$H NMR (400 MHz, CDCl$_3$) δ 2.15 (br s, 2H), 1.81-1.76 (m, 4H), 1.37-1.30 (m, 2H), 1.28-1.15 (m, 2H); $^{13}$C NMR (101 MHz, CDCl$_3$) 29.35, 24.51, 20.02.

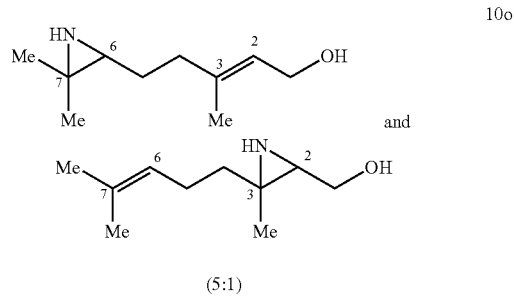

10o (5:1)

5-(3,3-Dimethylaziridin-2-yl)-3-methylpent-2(E)-en-1-ol

(50) Following the general aziridination procedure, geranyl alcohol 9o (46 mg, 0.3 mmol), aminating agent 1a (66 mg, 0.33 mmol, 1.1 equiv), and Rh$_2$(esp)$_2$ (2.3 mg, 3 μmol) were combined at 0° C. in CF$_3$CH$_2$OH (3 mL), then stirred at rt for 5 h. Chromatographic purification of the crude product over Florisil using 5-10% MeOH/CH$_2$Cl$_2$ as eluent afforded the title aziridine (30 mg, 59%) as an oil accompanied by the 2,3-regioisomer (6 mg, 12%). Major regioisomer. TLC R$_f$z 0.3 (20% MeOH/CH$_2$Cl$_2$); $^1$H NMR (500 MHz, CDCl$_3$) δ 5.44-5.42 (m, 1H), 4.15 (d, J=6.8 Hz, 2H), 2.21-2.05 (m, 2H), 1.75 (t, J=6.6 Hz, 1H), 1.69 (s, 3H), 1.62-1.46 (m, 2H), 1.25 (s, 3H), 1.16 (s, 3H); $^{13}$C NMR (126 MHz, CDCl$_3$) δ 138.77, 123.93, 59.12, 43.09, 37.75, 35.65, 28.11, 27.51, 19.69, 16.33. Minor regioisomer. 3-methyl-3-(4-methylpent-3-en-1-yl)aziridin-2(E)-yl)methanol: TLC: R$_f$=0.4 (20% MeOH/CH$_2$Cl$_2$); $^1$H NMR (500 MHz, CDCl$_3$) δ 5.12-5.08 (m, 1H), 3.74 (dd, J=11.5, 5.4 Hz, 1H), 3.55 (dd, J=11.5, 7.0 Hz, 1H), 2.19-2.07 (m, 3H), 1.70 (s, 3H), 1.63 (s, 3H), 1.63-1.57 (m, 1H), 1.35 (dt, J=13.7, 8.1 Hz, 1H), 1.19 (s, 3H); $^{13}$C NMR (101 MHz, CDCl$_3$) δ 132.22, 123.44, 61.48, 42.68, 41.52, 39.27, 25.69, 24.81, 17.67, 17.16.

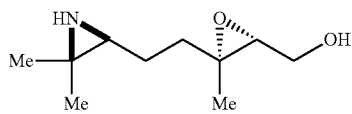

10p

((2R,3R)-3-(2-(3,3-dimethylaziridin-2-yl)ethyl)-3-methyloxiran-2-yl)methanol Following the general aziridination procedure, ((2R,3R)-3-methyl-3-(4-methylpent-3-en-1-yl)oxiran-2-yl)methanol (51) 9p (85 mg, 0.5 mmol), aminating agent 1a (0.119 g, 0.6 mmol), and Rh$_2$(esp)$_2$ (3.8 mg, 5 µmol) were stirred in CF$_3$CH$_2$OH (5 mL) at 0-5° C. for 4 h. Chromatographic purification on a CombiFlash system using 10-20% MeOH/CH$_2$Cl$_2$ as eluent to give the title aziridine (1:1 diastereomers) as an oil (78 mg, 84%). TLC: R$_f$=0.3 (10% MeOH/CH$_2$Cl$_2$); $^1$H NMR (400 MHz, CDCl$_3$) δ 3.74-3.61 (m, 2H), 2.94 (app q, J=5.4 Hz, 1H), 2.25 (br s, 2H), 1.83-1.68 (m, 2H), 1.65-1.35 (m, 3H), 1.28 (s, 1.5H), 1.27 (s, 1.5H), 1.23 (s, 3H), 1.14 (s, 1.5H), 1.13 (s, 1.5H); $^{13}$C NMR (101 MHz, CDCl3) δ 63.06, 62.69, 60.71, 60.67, 60.65, 60.64, 43.20, 42.97, 36.95, 36.53, 36.07, 35.92, 27.34, 27.28, 25.39, 25.30, 19.46, 19.39, 16.95, 16.57; HRMS (ESI$^+$) Calcd. for [C$_{10}$H$_{19}$NO$_2$+H]$^+$ 186.1489. Found 186.1490.

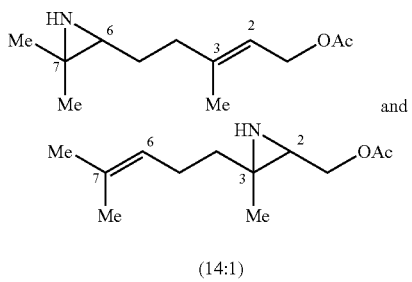

10q (14:1)

5-(3,3-Dimethylaziridin-2-yl)-3-methylpent-2(E)-en-1-yl acetate

Following the general aziridination procedure, geranyl acetate 9q (59 mg, 0.3 mmol), aminating agent 1a (72 mg, 0.36 mmol), and Rh$_2$(esp)$_2$ (2.3 mg, 3 µmol) were stirred in CF$_3$CH$_2$OH (3 mL) at rt for 3 h. Chromatographic purification of the crude product by Et$_3$N basified preparative TLC using 80% EtOAc/hexanes as eluent afforded the title aziridine as an oil (48 mg, 76%) and its 2,3-regioisomer (3.5 mg, 5%). 6,7-Regioisomer. TLC: R$_f$=0.3 (80% EtOAc/hexanes); $^1$H NMR (500 MHz, CDCl$_3$) δ 5.35 (tq, J=7.1, 1.4 Hz, 1H), 4.56 (d, J=7.2 Hz, 2H), 2.24-2.05 (m, 2H), 2.03 (s, 3H), 1.74 (t, J=6.6 Hz, 1H), 1.69 (s, 3H), 1.60-1.51 (m, 2H), 1.24 (s, 3H), 1.14 (s, 3H), 1.01 (br s, 1H); $^{13}$C NMR (126 MHz, CDCl$_3$) δ 171.08, 141.76, 118.58, 61.29, 43.02, 37.68, 35.86, 27.93, 27.40, 21.05, 19.62, 16.46; HRMS (ESI$^+$) Calcd. for [C$_{12}$H$_{21}$NO$_2$+H]$^+$ 212.1645. Found 212.1651. 2,3-Regioisomer. TLC: R$_f$=0.4 (80% EtOAc/hexanes); $^1$H NMR (500 MHz, CDCl$_3$) δ 5.09-5.05 (m, 1H), 4.16-4.00 (m, 2H), 2.16-1.99 (m, 3H), 2.06 (s, 3H), 1.66 (s, 3H), 1.60 (s, 3H), 1.60-1.54 (m, 1H), 1.31 (ddd, J=13.6, 9.2, 6.8 Hz, 1H), 1.17 (s, 3H), 0.46 (br s, 1H); $^{13}$C NMR (101 MHz, CDCl$_3$) δ 171.01, 132.11, 123.33, 64.89, 41.31, 39.28, 38.67, 25.65, 24.72, 20.90, 17.61, 17.41; HRMS (ESI) Calcd. for [C$_{12}$H$_{21}$NO$_2$+Na]$^+$ 234.1465. Found 234.1456.

When the above aziridination was repeated using 1.18 gram (6.0 mmol) of geranyl acetate, the yield of 6,7-regioisomer was 72% and 2,3-regioisomer was 5%.

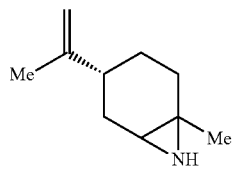

10r

4(R)-1-Methyl-4-(prop-1-en-2-yl)-7-azabicyclo[4.1.0]heptanes

(52) (R)-(+)-Limonene 9r (68 mg, 0.5 mmol), aminating agent 1a (0.119 g, 0.6 mmol), and Rh$_2$(esp)$_2$ (3.8 mg, 5 µmol) were combined at 0° C. in CH$_3$CF$_2$OH (5 mL), then stirred at rt for 12 h. Chromatographic purification on a CombiFlash system using 60-70% EtOAc/hexanes as eluent gave the title aziridine as an oil (54 mg, 72%) obtained as a 1:1 mixture of diastereomers. TLC: R$_f$ 0.3 (80% EtOAc/hexanes); $^1$H NMR (400 MHz, CDCl$_3$) of 1:1 mixture of diastereomers: δ 4.68-4.66 (m, 1H), 4.65-4.63 (m, 1H), 4.62-4.60 (m, 2H), 2.09-2.02 (m, 1H), 2.01-1.96 (m, 5H), 1.93-1.73 (m, 3H), 1.67-1.63 (m, 3H), 1.66 (s, 3H), 1.65 (s, 3H), 1.51-1.37 (m, 3H), 1.26 (s, 3H), 1.24 (s, 3H), 1.20-1.11 (m, 1H); $^{13}$C NMR (101 MHz, CDCl$_3$) δ 149.75, 149.43, 108.81, 108.70, 41.52, 39.25, 37.65, 36.61, 35.22, 34.53, 30.98, 30.55, 30.45, 29.52, 27.47, 26.50, 26.37, 24.86, 21.08, 20.38; HRMS (ESI$^+$) Calcd. for [C$_{10}$H$_{17}$NO+H]$^+$ 152.1434. Found 152.1436.

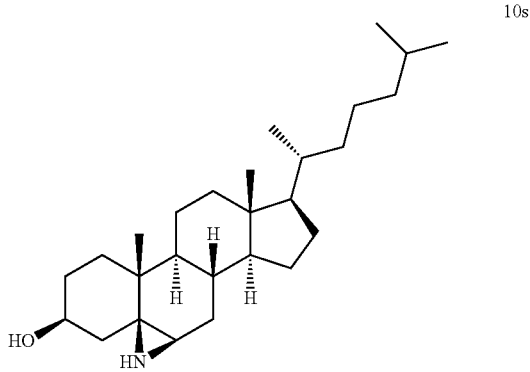

10s

5β,6β-Aziridinylcholestan-3-β-ol

(53) Following the general aziridination procedure, cholesterol 9s (0.193 g, 0.5 mmol), aminating agent 1a (0.119 g, 0.6 mmol), and Rh$_2$(esp)$_2$ (3.8 mg, 5 μmol) were stirred in a mixture of CH$_3$CF$_2$OH (3 mL) and THF (2 mL) at rt. After 24 h, another portion of catalyst (3.8 mg, 5 μmol, 1 mol %) and aminating agent (0.1 g, 0.5 mmol, 1.0 equiv) were added and the stirring was continued for an additional 24 h. Chromatographic purification on a CombiFlash system using 1-2% MeOH/CH$_2$Cl$_2$ as eluent afforded the title aziridine as a solid (0.14 g, 71%), mp 130-132° C. TLC: R$_f$=0.3 (10% MeOH/CH$_2$Cl$_2$); $^1$H NMR (400 MHz, CDCl$_3$, mixture of invertomers) δ 3.79-3.64 (m, 1H), 2.18 (dd, J=12.9, 11.3 Hz, 0.5H), 2.11 (br s, 0.5H), 1.99 (dd, J=12.8, 11.0 Hz, 0.5H), 1.91-1.85 (m, 4H), 1.80-1.70 (m, 2H), 1.62-1.59 (m, 1H), 1.50-1.47 (m, 2H), 1.34-1.26 (m, 9H), 1.09-1.06 (m, 6H), 1.03 (s, 3H), 0.93 (s, 3H), 0.85-0.80 (m, 11H), 0.60 (s, 1.5H), 0.56 (s, 1.5H); $^{13}$C NMR (101 MHz, CDCl$_3$) δ 68.97, 68.64, 57.08, 56.52, 56.21, 55.87, 51.13, 45.92, 45.23, 42.72, 42.65, 42.38, 42.28, 42.26, 42.19, 39.94, 39.44, 37.37, 36.93, 36.10, 36.08, 35.74, 35.68, 34.34, 34.11, 32.48, 32.31, 31.42, 30.96, 30.19, 29.92, 28.69, 28.14, 28.06, 27.95, 27.94, 24.14, 23.97, 23.84, 23.78, 22.78, 22.52, 22.23, 20.87, 18.66, 18.63, 18.60, 16.29, 11.89, 11.87; HRMS (ESI$^+$) Calcd. for [C$_{27}$H$_{47}$NO+H]$^+$ 402.3730. Found 402.3733.

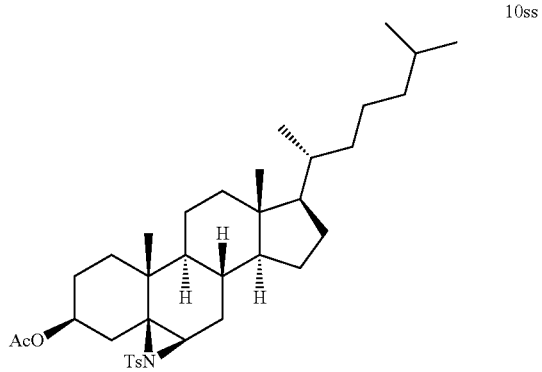

(3S,4aS,5aS,6aS,6bS,9R,9aR,11aS,11bR)-9a,11b-dimethyl-9-((R)-6-methylheptan-2-yl)-5-tosylhexadecahydro-1H-cyclopenta[1,2]phenanthro[8a,9-b]azirin-3-ylacetate

(54) Cholesterol aziridine 10s (80 mg, 0.2 mmol), tosyl chloride (46 mg, 0.24 mmol), acetic anhydride (0.4 mL) and pyridine (1 mL) were reacted following the literature described procedure.(54) Chromatographic separation of the crude product using EtOAc/hexanes (5-10%) as eluent furnished the title compound as a white solid (38 mg, 32%), m.p. 157-158° C., lit. m.p. 148-150° C. TLC: R$_f$=0.7 (30% EtOAc/hexanes); $^1$H NMR (400 MHz, CDCl$_3$) δ 7.78 (d, J=8.3 Hz, 2H), δ 7.28 (d, J=8.1 Hz, 2H), 4.95-4.88 (1H, m), 3.15 (br s, 1H), 2.53 (dd, J=13.3, 11.0 Hz, 1H), 2.43 (s, 3H), 2.29 (dd, J=13.3, 5.9 Hz, 1H), 2.04 (s, 3H), 2.00-1.87 (m, 1H), 1.90-1.67 (m, 4H), 1.60-0.91 (m, 19H), 1.05 (s, 3H), 0.91-0.73 (m, 10H), 0.73-0.62 (m, 1H), 0.57 (s, 3H); $^{13}$C NMR (101 MHz, CDCl$_3$) δ 170.52, 143.39, 139.05, 129.33, 126.83, 70.50, 57.02, 56.03, 55.94, 50.07, 48.30, 42.16, 39.68, 39.45, 36.16, 36.05, 35.68, 34.17, 32.53, 30.46, 29.89, 28.07, 27.98, 26.57, 24.09, 23.75, 22.79, 22.54, 22.03, 21.58, 21.32, 20.63, 18.62, 11.71.

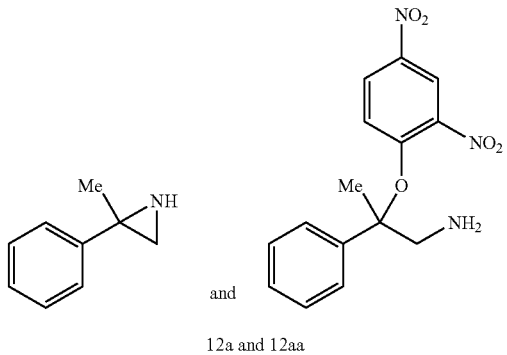 [SMILES: CC1(c2ccccc2)CN1 ; CC(CN)(Oc1ccc([N+](=O)[O-])cc1[N+](=O)[O-])c1ccccc1]

12a and 12aa

2-Methyl-2-phenylaziridine

(55) Following the general aziridination procedure, α-methylstyrene 11a (59 mg, 0.5 mmol), aminating agent 1a (0.119 g, 0.6 mmol), and Rh$_2$(esp)$_2$ (3.8 mg, 5 μmol) were stirred in CF$_3$CH$_2$OH (5 mL) at 0° C. for 2 h. Chromatographic purification by Et$_3$N basified preparative TLC using 60% EtOAc/hexanes as eluent afforded the title aziridine as an oil (42 mg, 64%) accompanied by aminoaryloxylated product 12aa (11 mg, 7%) as a sticky solid. Aziridine: TLC: R$_f$=0.3 (60% EtOAc/hexanes); $^1$H NMR (500 MHz, CDCl$_3$) δ 7.40-7.23 (m, 5H), 1.98 (s, 1H), 1.97 (s, 1H), 1.63 (s, 3H), 1.01 (br s, 1H); $^{13}$C NMR (126 MHz, CDCl$_3$) δ 143.60, 128.39, 126.82, 126.17, 36.97, 35.01, 25.17; HRMS (ESI$^+$) Calcd. for [C$_9$H$_{11}$N+H]$^+$ 134.0964. Found 134.0960.

2-(2,4-Dinitrophenoxy)-2-phenylpropan-1-amine

TLC: R$_f$=0.7 (60% EtOAc/hexanes); $^1$H NMR (400 MHz, CDCl$_3$) δ 9.01 (d, J=2.7 Hz, 1H), 8.79 (t, J=5.3 Hz, 1H), 8.13 (dd, J=9.6, 2.7 Hz, 1H), 7.59-7.45 (m, 2H), 7.44-7.36 (m, 2H), 7.35-7.19 (m, 1H), 6.85 (d, J=9.6 Hz, 1H), 3.70-3.57 (m, 2H), 1.75 (s, 3H); $^{13}$C NMR (101 MHz, CDCl$_3$) δ 148.51, 144.19, 135.83, 130.31, 130.08, 128.79, 127.91, 124.72, 124.18, 114.21, 74.00, 54.68, 27.79; HRMS (ESI$^-$) Calcd. for [C$_{15}$H$_{15}$N$_3$O$_5$—H]$^-$ 316.0939. Found 316.0929.

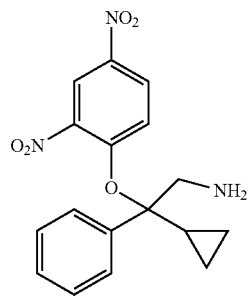

12b

2-Cyclopropyl-2-(2,4-dinitrophenoxy)-2-phenylethanamine

Rh$_2$(esp)$_2$ (3.8 mg, 5 μmol) and aminating agent 1a (0.119 g, 0.6 mmol) were added successively to a stirring solution of (1-cyclopropylvinyl)benzene(56) 11b (72 mg, 0.5 mmol) in CF$_3$CH$_2$OH (5 mL) at 0° C. After 2 h, the reaction mixture was diluted with CH$_2$Cl$_2$ (10 mL) followed by 15% aqueous NaHCO₃ solution (5 mL). The layers were separated and the aqueous layer was extracted with CH₂Cl₂ (10 mL×2). The combined organic layers were washed with brine (5 mL), dried over Na₂SO₄, and concentrated. The residue was purified on a CombiFlash system over SiO₂ using 15-20% EtOAc/hexanes to furnish the title amine as an oil (0.125 g, 73%). TLC: $R_f$≈0.5 (30% EtOAc/hexanes); ¹H NMR (500 MHz, CDCl₃) δ 9.06 (d, J=2.7 Hz, 1H), 8.87 (t, J=4.5 Hz, 1H), 8.19 (dd, J=9.5, 2.7 Hz, 1H), 7.64-7.50 (m, 2H), 7.44-7.39 (m, 2H), 7.36-7.31 (m, 1H), 6.92 (d, J=9.6 Hz, 1H), 3.88-3.69 (m, 2H), 2.03 (br s, 1H), 1.52-1.46 (m, 1H), 0.76-0.62 (m, 2H), 0.61-0.49 (m, 1H), 0.39-0.33 (m, 1H); ¹³C NMR (126 MHz, CDCl₃) δ 148.52, 143.10, 135.83, 130.34, 130.15, 128.72, 128.10, 125.38, 124.27, 114.18, 74.44, 54.20, 19.24, 1.52, 0.64; HRMS (ESI⁺) Calcd. for [C₁₇H₁₇N₃O₅+Na]⁺ 366.1060. Found 366.1052.

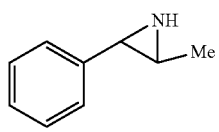

(E)-2-Methyl-3-phenylaziridine

(57) Following the general aziridination procedure, trans-β-methylstyrene 11c (59 mg, 0.5 mmol), aminating agent 1a (0.119 g, 0.6 mmol), and Rh₂(esp)₂ (3.8 mg, 5 μmol) were stirred in CF₃CH₂OH (5 mL) at −10° C. for 14 h. Chromatographic purification by Et₃N basified preparative TLC using 60% EtOAc/hexanes as eluent afforded the title aziridine as an oil (35 mg, 53%). TLC: $R_f$≈0.3 (50% EtOAc/hexanes); ¹H NMR (500 MHz, CDCl₃) δ 7.40-7.13 (m, 5H), 2.68 (d, J=2.9 Hz, 1H), 2.18-2.14 (m, 1H), 1.38 (d, J=5.5 Hz, 3H), 1.28 (br s, 1H); ¹³C NMR (126 MHz, CDCl₃) δ 140.37, 128.48, 126.98, 125.52, 40.46, 37.15, 19.64.

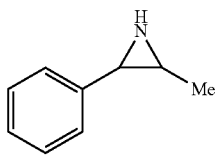

(Z)-2-Methyl-3-phenylaziridine

(57) Following the general aziridination procedure, cis-β-methylstyrene 11d (59 mg, 0.5 mmol), aminating agent 1a (0.119 g, 0.6 mmol), and Rh₂(esp)₂ (3.8 mg, 5 μmol, 1 mol %) were stirred in CF₃CH₂OH (5 mL) at −10° C. Two additional portions of catalysts (3.8 mg) were added at 24 h intervals. After a total of 68 h, the reaction was subjected to extractive isolation and the resultant crude material was chromatographically purified by Et₃N basified preparative TLC using 60% EtOAc/hexanes as eluent to give the title aziridine as an oil (51 mg, 76%). TLC: $R_f$≈0.4 (60% EtOAc/hexanes); ¹H NMR (500 MHz, CDCl₃) δ 7.46-7.19 (m, 5H), 3.26 (d, J=6.6 Hz, 1H), 2.42 (app qn, J=5.8 Hz, 1H), 1.46 (br s, 1H), 0.93 (d, J=5.8 Hz, 3H); ¹³C NMR (126 MHz, CDCl₃) δ 137.53, 127.92, 127.80, 126.65, 37.17, 32.24, 13.62.

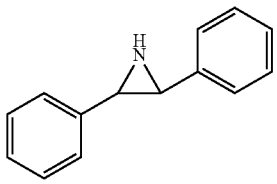

(E)-2,3-Diphenylaziridine

(58) Following the general aziridination procedure, trans-stilbene 11e (90 mg, 0.5 mmol), aminating agent 1a (0.109 g, 0.55 mmol, 1.1 equiv), and Rh₂(esp)₂ (3.8 mg, 5 μmol) were stirred in a mixture of CF₃CH₂OH (3 mL) and THF (2 mL) at rt. After 16 h, another portion of catalyst (5 μmol, 3.8 mg) and aminating agent (0.02 g, 0.1 mmol, 0.2 equiv) was added and the stirring was continued for another an additional 7 h. Chromatographic purification on a CombiFlash system over ᵗBu₃N basified SiO₂ using 10-15% EtOAc/hexanes to afford the title aziridine as an oil (49 mg, 51%). TLC: $R_f$≈0.4 (30% EtOAc/hexanes); ¹H NMR (500 MHz, CDCl₃) δ 7.66-6.82 (m, 10H), 3.12 (br s, 2H), 1.50 (br s, 1H); ¹³C NMR (126 MHz, CDCl₃) δ 139.60, 128.62, 127.32, 125.47, 43.70.

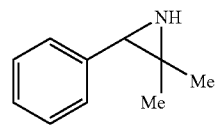

2,2-Dimethyl-3-phenylaziridine

(59) Following the general procedure, (2-methylprop-1-en-1-yl)benzene 11f (0.132 g, 1.0 mmol), aminating agent 1a (0.219 g, 1.1 mmol, 1.1 equiv), and Rh₂(esp)₂ (7.6 mg, 10 μmol) were stirred in CF₃CH₂OH (10 mL) at rt for 3 h. Chromatographic purification by flash column chromatography over Florisil® using 10-25% EtOAc/hexanes as eluent afforded the title aziridine as an oil (0.135 g, 92%). TLC: $R_f$≈0.4 (50% EtOAc/hexanes); ¹H NMR (500 MHz, CDCl₃) δ 7.34-7.30 (m, 4H), 7.28-7.17 (m, 1H), 3.05 (s, 1H), 1.46 (s, 3H), 0.94 (s, 3H), 0.65 (br s, 1H); ¹³C NMR (101 MHz, CDCl₃) 138.43, 127.91, 127.50, 126.51, 45.39, 38.49, 27.51, 19.43; HRMS (ESI⁺) Calcd. for [C₁₀H₁₃N+H]⁺ 148.1121. Found 148.1122.

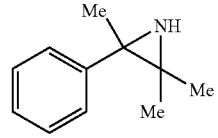

2,2,3-trimethyl-3-phenylaziridine

Following the general procedure, (3-methylbut-2-en-2-yl)benzene* 11g (50 mg, 0.34 mmol), aminating agent 1a (82 mg, 0.41 mmol), and Rh₂(esp)₂ (2.6 mg, 3.4 μmol) were stirred in CF₃CH₂OH (3 mL) at rt for 1 h. Chromatographic purification by prep TLC afforded the title aziridine as an oil (38 mg, 70%) (Both the proton and carbon NMR shows some impurity that is hard to get rid of). TLC: $R_f$≈0.2 (50% EtOAc/hexanes); $^1$H NMR (400 MHz, CDCl$_3$) δ 7.37-7.14 (m, 5H), 1.54 (s, 3H), 1.40 (s, 3H), 1.28 (br s, 1H), 0.88 (s, 3H); $^{13}$C NMR (101 MHz, CDCl$_3$) 144.03, 128.13, 127.17, 126.35, 47.41, 41.02, 23.99, 23.56, 21.89; HRMS (ESI$^+$) Calcd. for $[C_{11}H_{15}N+H]^+$ 162.1277. Found 162.1280.

*The starting olefin bought from Aldrich contains significant amount of impurities which is carried through the aziridination. Repeated column chromatography could not remove the impurities completely. Conversion of the aziridine 12g to acetate 12gg afforded pure N-protected aziridine.

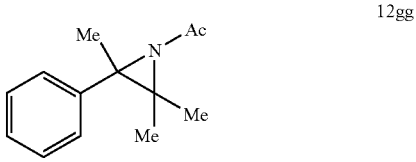 [SMILES: CC(=O)N1C(C)(C)C1(C)c1ccccc1]

12gg 1-(2,2,3-trimethyl-3-phenylaziridine-1-yl)ethanone 2,2,3-trimethyl-3-phenylaziridine 12g (15 mg, 93 μmol), acetic anhydride (17 μL, 0.13 mmol), pyridine (11 μL, 0.13 mmol) were reacted in CH$_2$Cl$_2$ (1 mL) at rt for 3 h. Evaporation of volatiles and chromatographic purification by prep TLC using 40% EtOAc/hexanes as eluent afforded the title N-protected aziridine as a light yellow oil (18 mg, 90%). TLC: $R_f$≈0.4 (40% EtOAc/hexanes); $^1$H NMR (400 MHz, CDCl$_3$) δ 7.36-7.14 (m, 5H), 2.13 (s, 3H), 1.65 (s, 3H), 1.49 (s, 3H), 0.92 (s, 3H); $^{13}$C NMR (101 MHz, CDCl$_3$) δ 177.74, 141.40, 128.24, 126.99, 126.78, 50.91, 46.62, 24.99, 22.43, 19.47, 18.73.

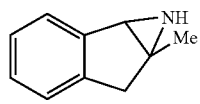

12h

6a-Methyl-1,1a,6,6a-tetrahydroindeno[1,2-b]azirine

2-Methylindene 11h (0.130 g, 1.0 mmol), aminating agent 1a (0.219 g, 1.1 mmol, 1.1 equiv), and Rh$_2$(esp)$_2$ (7.6 mg, 10 μmol) were combined in CF$_3$CH$_2$OH (10 mL) at 0° C. with stirring. The mixture was then warmed to 5° C. and maintained at this temperature for 2.5 h. Chromatographic purification via flash column chromatography over Florisil® using 20-30% EtOAc/hexanes as eluent afforded the title aziridine as a pale yellow oil (20 mg, 14%). TLC: $R_f$≈0.4 (50% EtOAc/hexanes); $^1$H NMR (500 MHz, CDCl$_3$) δ 7.38 (dd, J=6.6, 1.8 Hz, 1H), 7.27-7.07 (m, 3H), 3.24-2.91 (m, 3H), 1.57 (s, 3H); HRMS (ESI$^+$) Calcd. for $[C_{10}H_{11}N+H]^+$ 146.0964. Found 146.0964.

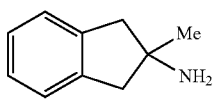

12hh

2-Methyl-2,3-dihydro-1H-inden-2-amine

(60) 2-Methylindene 11h (0.130 g, 1.0 mmol), aminating agent 1a (0.239 g, 1.2 mmol), and Rh$_2$(esp)$_2$ (7.6 mg, 10 μmol) in CF$_3$CH$_2$OH (10 mL) reacted exactly as above. The crude product (0.143 g), without further purification, was subjected to catalytic hydrogenation over 10% Pd/C (10 mg) in dry MeOH (5 mL) at 1 atm hydrogen pressure (balloon). After 15 h, the reaction mixture was passed through a small plug of cotton. The plug was washed with MeOH (3 mL) and the solvent was evaporated. The residue was purified by CombiFlash column chromatography over SiO$_2$ using 10-20% MeOH/CH$_2$Cl$_2$ as eluent to give the title amine as a pale yellow solid (88 mg, 60%), decomposes (or charring) >211° C. TLC: $R_f$≈0.3 (20% MeOH/CH$_2$Cl$_2$); $^1$H NMR (500 MHz, CDCl$_3$) δ 7.27-7.11 (m, 4H), 3.40 (d, J=15.9 Hz, 2H), 3.07 (d, J=15.8 Hz, 2H), 1.62 (s, 3H); $^{13}$C NMR (126 MHz, CDCl$_3$) δ 139.24, 127.29, 124.97, 61.49, 44.66, 24.93; HRMS (ESI$^+$) Calcd. for $[C_{10}H_{13}N+H]^+$ 148.1121. Found 148.1116.

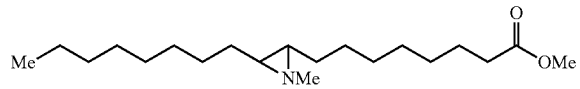

13a

Methyl (E)-8-(1-methyl-3-octylaziridine-2-yl)octanoate

Following the general aziridination procedure, methyl elaidate 9h (59 mg, 0.2 mmol), N-methylaminating agent (61) 1b (51 mg, 0.24 mmol), and Rh$_2$(esp)$_2$ (1.5 mg, 2 μmol) were stirred in CF$_3$CH$_2$OH (2 mL) at rt. After 2 h, another portion of catalyst (0.8 mg, 0.5 mol %) and aminating agent (9 mg, 0.04 mmol, 0.2 equiv) were added and the stirring was continued for an additional 2 h. Chromatographic purification on a CombiFlash system over SiO$_2$ gave the title aziridine as an oil (51 mg, 78%). TLC: $R_f$≈0.3 (50% EtOAc/hexanes); $^1$H NMR (400 MHz, CDCl$_3$; 1:1 mixture of invertomers) δ 3.62 (s, 3H), 2.33 (s, 3H), 2.27 (t, J=7.5 Hz, 1H), 2.26 (t, J=7.5 Hz, 1H), 1.65-1.50 (m, 4H), 1.45-1.11 (m, 23H), 1.04-0.91 (m, 1H), 0.84 (t, J=6.8 Hz, 1.5H), 0.83 (t, J=6.8 Hz, 1.5H); $^{13}$C NMR (101 MHz, CDCl$_3$) δ 174.20, 174.17, 51.38, 51.36, 51.34, 47.08, 47.03, 42.90, 42.85, 38.78, 34.03, 34.01, 33.22, 33.18, 31.83, 29.57, 29.52, 29.49, 29.46, 29.30, 29.24, 29.20, 29.14, 29.04, 28.47, 28.40, 27.48, 27.39, 25.60, 25.58, 24.88, 24.87, 22.62, 14.05; HRMS (ESI$^+$) Calcd. for $[C_{20}H_{39}NO_2+H]$ 326.3054. Found 326.3049.

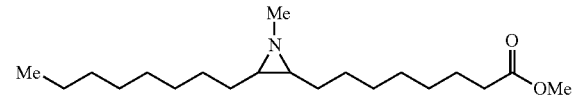

13b

Methyl (Z)-8-(1-methyl-3-octylaziridine-2-yl)octanoate

Following the general aziridination procedure, methyl oleate 7 (89 mg, 0.3 mmol), N-methylaminating agent 1b (77 mg, 0.36 mmol), and Rh$_2$(esp)$_2$ (2.3 mg, 3 μmol) were stirred in CF$_3$CH$_2$OH (3 mL) at rt for 2 h. Thereafter, two more portions of catalyst (1.1 mg, 0.5 mol %) and aminating agent (13 mg, 0.06 mmol, 0.2 equiv) were added after every 2 h and stirred for a total of 6 h. Chromatographic purification on a CombiFlash system over SiO₂ to give the title aziridine as an oil (78 mg, 80%). TLC: R$_f$≈0.5 (50% EtOAc/hexanes); ¹H NMR (500 MHz, CDCl₃) δ 3.64 (s, 3H), 2.31 (s, 3H), 2.27 (t, J=7.6 Hz, 2H), 1.64-1.54 (m, 2H), 1.46-1.19 (m, 24H), 1.19-1.14 (m, 2H), 0.85 (t, J=6.9 Hz, 3H); ¹³C NMR (126 MHz, CDCl₃) δ 174.28, 51.42, 48.12, 45.46, 45.41, 34.05, 31.86, 29.62, 29.61, 29.39, 29.27, 29.26, 29.07, 28.22, 28.18, 28.12, 28.05, 24.90, 22.67, 14.11; HRMS (ESI⁺) Calcd. for [C₂₀H₃₉NO₂+Na]348.2873. Found 348.2863.

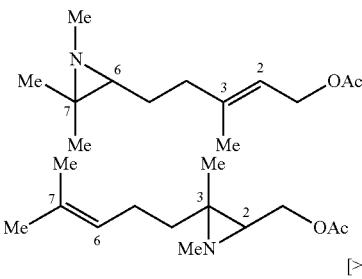

(E)-3-Methyl-5-(1,3,3-trimethylaziridine-2-yl)pent-2-en-1-yl acetate

Following the general azirdination procedure, geranyl acetate 9q (98 mg, 0.5 mmol), N-methylaminating agent 1b (0.128 g, 0.6 mmol), and Rh₂(esp)₂ (3.8 mg, 5 μmol) were stirred in CF₃CH₂OH (5 mL) at rt. After 2 h, another portion of catalyst (1 mg, 0.25 mol %) and aminating agent (21 mg, 0.1 mmol, 0.2 equiv) were added and the stirring was continued for another 2 h. Chromatographic purification on a CombiFlash system over SiO₂ gave the title aziridine as an oil (91 mg, 81%) accompanied by the 2,3-regioisomer (3 mg, 3%). Major regioisomer. TLC: R$_f$≈0.2 (10% MeOH/CH₂Cl₂); ¹H NMR (500 MHz, CDCl₃) δ 5.37-5.27 (m, 1H), 4.53 (d, J=7.1 Hz, 2H), 2.30 (s, 3H), 2.15-2.05 (m, 2H), 1.98 (s, 3H), 1.65 (s, 3H), 1.56-1.35 (m, 2H), 1.11 (s, 3H), 1.01 (s, 3H), 0.99 (t, J=6.5 Hz, 1H); ¹³C NMR (126 MHz, CDCl₃) δ 171.01, 141.93, 118.50, 61.26, 51.77, 39.60, 39.13, 37.70, 27.44, 21.75, 20.98, 17.87, 16.30; HRMS (ESI⁺) Calcd. for [C₁₃H₂₃NO₂+H]⁺ 226.1802. Found 226.1801. Minor regioisomer. ¹H NMR (400 MHz, CDCl₃) δ 5.16-5.01 (m, 1H), 4.04 (d, J=6.4 Hz, 2H), 2.43 (s, 3H), 2.20-2.01 (m, 2H), 2.06 (s, 3H), 1.68 (s, 3H), 1.60 (s, 3H), 1.55-1.39 (m, 3H), 1.12 (s, 3H); 13C NMR (126 MHz, CDCl₃) δ 171.07, 131.98, 123.59, 64.74, 48.41, 39.09, 32.03, 29.68, 25.67, 25.10, 20.95, 19.19, 17.64; HRMS (ESI) Calcd. for [C₁₃H₂₃NO₂+H]⁺ 226.1802. Found 226.1797.

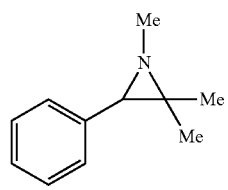

1,2,2-Trimethyl-3-phenylaziridine

Following the general aziridine procedure, 2-methyl-1-phenyl-2-propene 11 if (66 mg, 0.5 mmol), N-methylaminating agent 1b (0.128 g, 0.6 mmol), and Rh₂(esp)₂ (3.8 mg, 5 μmol) were stirred in CF₃CH₂OH (5 mL) at rt. After 2 h, another portion of catalyst (1 mg, 0.25 mol %) and aminating agent (21 mg, 0.1 mmol, 0.2 equiv) were added to the reaction mixture. Following 2 h more, the crude reaction mixture was purified on a CombiFlash system over SiO₂ to give the title aziridine as an oil (65 mg, 81%). TLC: R$_f$≈0.4 (20% EtOAc/hexanes); ¹H NMR (500 MHz, CDCl₃) δ 7.35-7.28 (m, 4H), 7.27-7.17 (m, 1H), 2.58 (s, 3H), 2.36 (s, 1H), 1.37 (s, 3H), 0.91 (s, 3H); ¹³C NMR (126 MHz, CDCl₃) δ 138.81, 127.89, 127.43, 126.38, 54.39, 42.70, 39.59, 21.47, 17.68; HRMS (ESI⁺) Calcd. for [C₁₁H₁₅N+H]⁺ 162.1277. Found 162.1271.

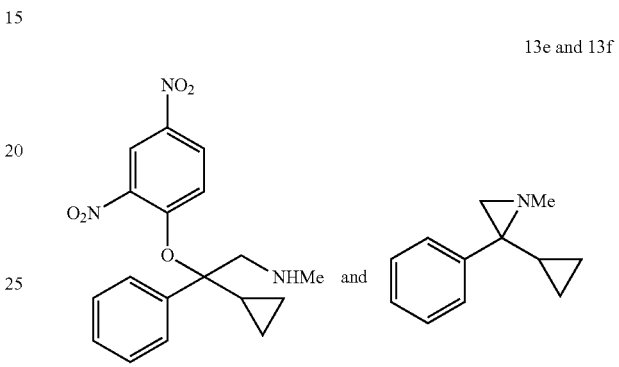

2-Cyclopropyl-2-(2,4-dinitrophenoxy)-N-methyl-2-phenylethanamine (1-Cyclopropylvinyl)-benzene 11b (72 mg, 0.5 mmol), Rh₂(esp)₂ (3.8 mg, 5 μmol), and N-Methyl aminating agent 1b (0.128 g, 0.6 mmol) were reacted in CF₃CH₂OH (5 mL) following the procedure described above for 2-cyclopropyl-2-(2,4-dinitrophenoxy)-2-phenylethanamine 13e. Chromatographic purification on a CombiFlash system over SiO₂ furnished the title N-methylamine SI-11e as a viscous oil (42 mg, 24%) accompanied by the precursor N-methylaziridine SI-11f (13 mg, 15%).

2-Cyclopropyl-2-(2,4-dinitrophenoxy)-N-methyl-2-phenylethanamine

TLC: R$_f$≈0.7 (50% EtOAc/hexanes); ¹H NMR (500 MHz, CDCl₃) δ 8.61 (d, J=2.7 Hz, 1H), 8.06 (dd, J=9.5, 2.7 Hz, 1H), 7.54-7.45 (m, 2H), 7.39-7.30 (m, 2H), 7.32-7.24 (m, 1H), 7.13 (d, J=9.6 Hz, 1H), 3.98 (d, J=14.7 Hz, 1H), 3.90 (d, J=14.8 Hz, 1H), 2.82 (s, 3H), 2.13 (s, 1H), 1.43-1.37 (m, 1H), 0.65-0.54 (m, 1H), 0.53-0.40 (m, 2H), 0.33-0.29 (m, 1H); ¹³C NMR (126 MHz, CDCl₃) δ 149.97, 144.07, 136.97, 136.92, 128.46, 127.68, 126.95, 125.37, 123.75, 119.08, 75.86, 64.34, 44.87, 19.38, 1.55, 1.15; HRMS (ESI⁺) Calcd. for [C₁₈H₁₉N₃O₅+Na]⁺ 380.1217. Found 380.1211. 2-Cyclopropyl-1-methyl-2-phenylaziridine: TLC: R$_f$≈0.5 (50% EtOAc/hexanes); ¹H NMR (500 MHz, CDCl₃, 1:4 mixture of invertomers) Major invertomer: δ 7.45-7.25 (m, 5H), 2.01 (s, 3H), 1.94 (s, 1H), 1.60 (s, 1H), 1.31-1.20 (m, 1H), 0.56-0.50 (m, 1H), 0.46-0.41 (m, 1H), 0.33-0.25 (m, 2H); ¹³C NMR (101 MHz, CDCl₃) δ 138.86, 130.15, 128.02, 127.37, 47.36, 42.37, 38.10, 18.22, 3.45, 1.17. Minor invertomer: δ 7.45-7.25 (m, 1.0H, overlapped with major invertomer), 2.72 (s, 0.74H), 1.86 (br s, 0.30H), 1.55 (s, 0.24H), 1.20-1.15 (m, 0.22H), 0.72-0.66 (m, 0.21H), 0.65-0.60 (m, 0.21H), 0.39-0.35 (m, 0.45H); ¹³C NMR (101

MHz, CDCl$_3$): δ 143.49, 127.85, 127.71, 126.42, 46.42, 40.59, 39.73, 10.98, 5.23, 2.92; HRMS (ESI$^+$): Calcd. for [C$_{12}$H$_{15}$N+H]$^+$ 174.1277. Found 174.1281.

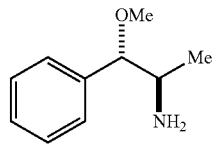

14 erythro-1-Methoxy-1-phenylpropan-2-amine

(62) CSA (46 mg, 0.2 mmol) was added to a stirring 0° C. solution of (E)-2-methyl-3-phenylaziridine 12c (27 mg, 0.2 mmol) in dry MeOH (2 mL). After 1 h, the reaction mixture was warmed to rt. After 16 h, the reaction mixture was warmed to 40° C. and held at this temperature for an additional 1 h. The reaction mixture was then cooled to rt, diluted with CHCl$_3$ (5 mL), and the pH was adjusted to 8.5 using aqueous 1.0 M NaOH. The layers were separated, and the aqueous layer was extracted with CHCl$_3$ (5 m×3). The combined organic layers were washed with brine (5 mL), dried over Na$_2$SO$_4$, and concentrated to obtain the title amino-alcohol as a light yellow oil in quantitative yield (33 mg). TLC: R$_f$=0.2 (10% MeOH/DCM); $^1$H NMR (400 MHz, CDCl$_3$): δ 7.45-7.08 (m, 5H), 3.93 (d, J=5.5 Hz, 1H), 3.24 (s, 3H), 3.14 (app qn, J=6.0 Hz, 1H), 1.32 (br s, 2H), 1.05 (d, J=6.5 Hz, 3H); $^{13}$C NMR (101 MHz, CDCl$_3$): δ 138.89, 128.22, 127.73, 127.60, 88.92, 57.01, 51.67, 19.19; HRMS (ESI$^+$): Calcd. for [C$_{10}$H$_{15}$NO+H]$^+$ 166.1226. Found 166.1220.

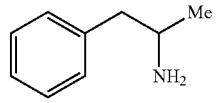

15

1-Phenylpropan-2-amine

(63) A suspension of (E)-2-methyl-3-phenylaziridine 12c (20 mg, 0.15 mmol) and 10% Pd/C (10 mg) in MeOH (1 mL) was stirred under a hydrogen atmosphere (1 atm) at rt for 16 h. The reaction mixture was filtered by passage through a small pad of Celite™. The pad was washed with methanol and the combined filtrates were evaporated to furnish the title amine as an oil (19 mg, 96%). $^1$H NMR (500 MHz, CDCl$_3$) δ 8.46 (br s, 2H), 7.34-7.20 (m, 5H), 3.65-3.53 (m, 1H), 3.27 (dd, J=13.4, 5.1 Hz, 1H), 2.87 (dd, J=13.3, 9.1 Hz, 1H), 1.39 (d, J=6.4 Hz, 3H); $^{13}$C NMR (126 MHz, CDCl$_3$) δ 135.83, 129.35, 128.87, 127.26, 49.80, 41.07, 18.13.

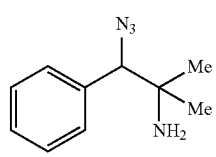

16

1-Azido-2-methyl-1-phenylpropan-2-amine

CSA (77 mg, 0.33 mmol, 1.1 equiv) was added to a stirring 0° C. solution of 2,2-dimethyl-3-phenylaziridine 12f (44 mg, 0.3 mmol) in dry CH$_3$CN (3 mL). After 10 min, NaN$_3$ (59 mg, 0.9 mmol, 3.0 equiv) was added and the temperature was then raised to 50° C. After 46 h, the reaction mixture was cooled to rt, diluted with CHCl$_3$ (5 mL), and the pH was adjusted to 8.5 using aqueous 1.0 M NaOH. The layers were separated and the aqueous layer was extracted with CHCl$_3$ (5 mL×3). The combined organic layers were washed with brine (5 mL), dried over Na$_2$SO$_4$, and concentrated. The residue was purified on a CombiFlash system over SiO$_2$ using 70-80% EtOAc/hexanes as eluent to give the title azido-amine as an oil (45 mg, 79%). TLC: R$_f$=0.3 (80% EtOAc/hexanes); $^1$H NMR (500 MHz, CDCl$_3$) δ 7.40-7.27 (m, 5H), 4.41 (s, 1H), 1.33 (br s, 2H), 1.13 (s, 3H), 1.01 (s, 3H); $^{13}$C NMR (126 MHz, CDCl$_3$) δ 136.76, 128.40, 128.26, 128.25, 76.60, 53.01, 27.67, 26.71; HRMS (ESI$^+$) Calcd. for [C$_{10}$H$_{14}$N$_4$+H]$^+$ 191.1291. Found 191.1287; IR (neat) 3366, 3320, 2971, 2102 cm$^{-1}$.

Starting Alkenes Synthesis:

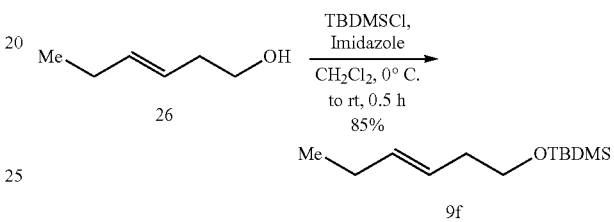

(E)-tert-butyl(hex-3-en-1-yloxy)dimethylsilane

To a stirred solution of (E)-hex-3-en-1-ol 26 (0.3 g, 3.0 mmol) in dry CH$_2$Cl$_2$ (6 mL) at rt was added imidazole (0.245 g, 3.6 mmol) in one portion, and the reaction mixture was cooled to 0° C. Then tert-butyldimethylchlorosilane (TBDMSCl) (0.542 g, 3.6 mmol) was added in one portion; stirring was continued at that temperature for 10 minutes before warming up to rt. TLC analysis after a total of 30 min indicated the reaction was complete. The reaction mixture was then diluted with CH$_2$Cl$_2$ (10 mL) and washed once with water (10 mL). The aqueous layer was extracted once with CH$_2$Cl$_2$ (10 mL) and the combined organic extracts were washed with brine (5 mL), dried over Na$_2$SO$_4$, and concentrated in vacuo to obtain the crude product which was purified by Combiflash column chromatography using a gradient EtOAc/hexanes (2-3%) as eluent to furnish title protected alcohol as a colorless oil (0.55 g, 85%). TLC: R$_f$=0.8 (5% EtOAc/hexanes); $^1$H NMR (400 MHz, CDCl$_3$) δ 5.58-5.45 (m, 1H), 5.45-5.32 (m, 1H), 3.61 (t, J=7.0 Hz, 2H), 2.26-2.15 (m, 2H), 2.06-1.94 (m, 2H), 0.96 (t, J=7.4 Hz, 3H), 0.89 (s, 9H), 0.05 (s, 6H); $^{13}$C NMR (101 MHz, CDCl$_3$) δ 134.14, 125.32, 63.38, 36.26, 25.95, 25.66, 18.38, 13.78, −5.24.

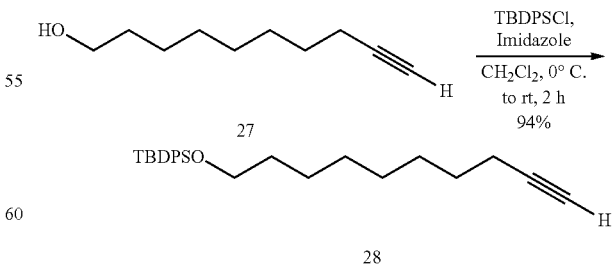

tert-butyl(dec-9-yn-1-yloxy)diphenylsilane

To a stirring solution of dec-9-yn-1-ol(64) 27 (1.5 g, 9.7 mmol) in dry CH$_2$Cl$_2$ (20 mL) at rt was added imidazole (0.794 g, 11.6 mmol) in one portion. The reaction mixture was cooled to 0° C. Then tert-butyldiphenylchlorosilane (TBDPSCl) (2.91 g, 10.6 mmol) was added dropwise and the reaction mixture was stirred for 10 minutes before warming up to rt. After stirring for a total of 2 h (TLC analysis), the reaction mixture was diluted with $CH_2Cl_2$ (10 mL), water (10 mL) was added, and the layers were separated. The aqueous layer was extracted with $CH_2Cl_2$ (2×20 mL) and the combined organic extracts were washed with brine (20 mL), dried over $Na_2SO_4$, and concentrated in vacuo. The crude product was purified by Combiflash column chromatography using a gradient EtOAc/hexanes (1-3%) as eluent to furnish the title alkyne as a colorless viscous oil (3.60 g, 94%). TLC: $R_f$=0.8 (5% EtOAc/hexanes); $^1$H NMR (400 MHz, $CDCl_3$) δ 7.70-7.65 (m, 4H), 7.50-7.31 (m, 6H), 3.66 (t, J=6.5 Hz, 2H), 2.18 (td, J=7.1, 2.7 Hz, 2H), 1.94 (t, J=2.6 Hz, 1H), 1.64-1.46 (m, 4H), 1.46-1.22 (m, 8H), 1.06 (s, 9H); $^{13}$C NMR (101 MHz, $CDCl_3$) δ 135.57, 134.15, 129.47, 127.55, 84.78, 68.06, 63.96, 32.54, 29.21, 29.06, 28.69, 28.47, 26.87, 25.71, 19.22, 18.40; HRMS (ESI$^+$) Calcd. for $[C_{26}H_{36}OSi+H]^+$ 393.2608. Found 393.2609.

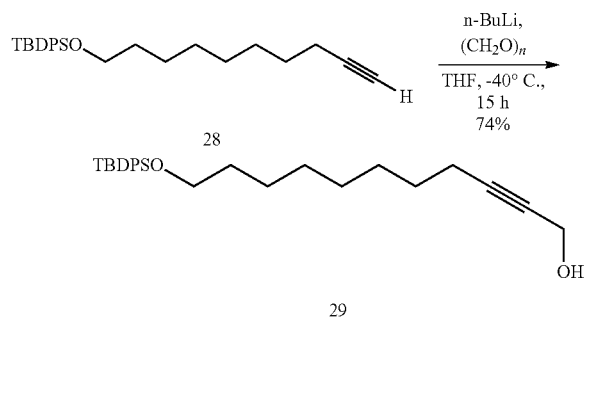

11-((tert-butyldiphenylsilyl)oxy)undec-2-yn-1-ol

To a stirring solution of tert-butyl(dec-9-yn-1-yloxy)diphenylsilane 28 (0.325 g, 0.83 mmol) in dry THF (3 mL) at −40° C. was added n-BuLi (2.5 M in hexanes, 0.4 mL, 0.996 mmol), and the resulting light yellow solution was stirred at that temperature for 10 min. A suspension of paraformaldehyde (0.075 g, 2.49 mmol) in dry THF (1 mL) at −40° C. was then added via cannula, and the stirring was continued at that temperature for 15 minutes before warming up to rt. After a total of 15 h (TLC analysis), saturated aqueous $NH_4Cl$ solution (2 mL) and EtOAc (10 mL) were added to the reaction mixture. The layers were separated and the aqueous layer was extracted with EtOAc (2×10 mL). The combined organic extracts were washed with brine (10 mL), dried over $Na_2SO_4$, and concentrated in vacuo. The crude product was purified by Combiflash column chromatography using a gradient of EtOAc/hexanes (10-15%) as eluent to furnish the title alcohol as a thick, colorless oil (0.26 g, 74%). TLC: $R_f$=0.3 (20% EtOAc/hexanes); $^1$H NMR (400 MHz, $CDCl_3$) δ 7.70-7.64 (m, 4H), 7.46-7.34 (m, 6H), 4.25 (dt, J=6.0, 2.2 Hz, 2H), 3.65 (t, J=6.5 Hz, 2H), 2.21 (tt, J=7.1, 2.2 Hz, 2H), 1.64-1.43 (m, 4H), 1.42-1.21 (m, 8H), 1.05 (s, 9H); $^{13}$C NMR (101 MHz, $CDCl_3$) δ 135.56, 134.14, 129.47, 127.55, 86.65, 78.26, 63.97, 51.44, 32.53, 29.21, 29.07, 28.79, 28.57, 26.87, 25.71, 19.22, 18.73; HRMS (ESI$^+$) Calcd. for $[C_{27}H_{38}O_2Si+Na]^+$ 445.2533. Found 445.2524.

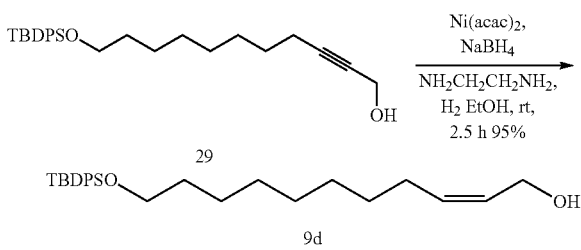

(Z)-11-((tert-Butyldiphenylsilyl)oxy)undec-2-en-1-ol

To a stirring solution of Ni(acac)$_2$.4H$_2$O (0.348 g, 1.4 mmol) in absolute ethanol (12 mL) at rt was added NaBH$_4$ (53 mg, 1.4 mmol). The resulting black reaction mixture was stirred under H$_2$ (1 atm) for 20 minutes before adding ethylenediamine (0.19 mL, 2.9 mmol). After 15 min, a solution of 11-((tert-butyldiphenylsilyl)oxy)undec-2-yn-1-ol 29 (2.49 g, 5.9 mmol) in absolute ethanol (10 mL) was added and the stirring was continued for a total of 2.5 h (TLC analysis). The reaction mixture was then passed through a small pad of silica to remove the solids. The filtrate was concentrated and the crude product was purified by Combi-flash column chromatography using a gradient of EtOAc/hexanes (20-25%) as eluent to furnish the title alcohol as a viscous, colorless oil (2.38 g, 95%). TLC: $R_f$=0.6 (40% EtOAc/hexanes); $^1$H NMR (400 MHz, $CDCl_3$) δ 7.70-7.64 (m, 4H), 7.48-7.29 (m, 6H), 5.67-5.45 (m, 2H), 4.20 (d, J=6.2 Hz, 2H), 3.66 (t, J=6.5 Hz, 2H), 2.07 (app q, J=7.1 Hz, 2H), 1.68-1.45 (m, 3H), 1.46-1.16 (m, 10H), 1.05 (s, 9H); $^{13}$C NMR (101 MHz, $CDCl_3$) δ 135.56, 134.15, 133.27, 129.47, 128.27, 127.55, 63.97, 58.62, 32.55, 29.59, 29.42, 29.30, 29.14, 27.43, 26.87, 25.74, 19.22; HRMS (ESI$^+$) Calcd. for $[C_{27}H_{40}O_2Si+H]^+$ 425.2876. Found 425.2881.

Copper Catalyst

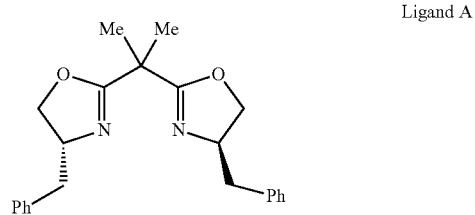 [SMILES: CC(C)(C1=N[C@H](Cc2ccccc2)CO1)C1=N[C@H](Cc2ccccc2)CO1]

Ligand A

To a stirred rt solution of ligand A (6.7 mg, 0.02 mmol, 10 mol %) in trifluoroethanol (2 mL) was added CuCl$_2$ (2.7 mg, 0.02 mmol, 10 mol %) and stirred for about 1 h. The greenish solution was then cooled down to 0° C., and trans-β-methyl styrene (24 mg, 0.2 mmol) and aminating agent, TsONHMe (60.0 mg, 0.3 mmol) were added. The TLC analysis showed the reaction was complete after a total of 3 h (disappearance of starting material). The reaction mixture was then diluted with EtOAc (5 mL) and washed with saturated NaHCO$_3$ solution (2 mL). The organic layer was washed with brine (2 mL) and dried (anhydrous Na$_2$SO$_4$). The crude residue was then purified by preparative thin layer chromatography using 8% MeOH:CH$_2$Cl$_2$ as an eluent containing about 1% $^t$BuNH$_2$ to get the titled N-methyl aziridine as light yellow oil (7 mg, 24%). TLC: $R_f$=0.5 (8% MeOH/CH$_2$Cl$_2$); $^1$H NMR (400 MHz, $CDCl_3$)

δ 7.33-7.25 (m, 2H), 7.22-7.15 (m, 2H), 2.53 (s, 3H), 2.13-2.09 (m, 1H), 2.08-2.03 (m, 1H), 1.35 (d, J=5.9 Hz, 3H).

[Reaction scheme: olefin with R1, R2, R3, R4 substituents (1.0 equiv) + p-tolyl-SO2ONHMe (1.5 equiv), 20 mol% CuCl2, TFE, rt, 3 h → N,N-dimethyl phenyl aziridine]

Having thus described exemplary embodiments of the present invention, it should be noted by those of ordinary skill in the art that the within disclosures are exemplary only and that various other alternatives, adaptations, and modifications may be made within the scope of the present invention. Accordingly, the present invention is not limited to the specific embodiments described herein.

The invention claimed is:

1. A process for making an aziridine of the formula AP-1

[Structure AP-1: aziridine with $R^{14}$ on N, and $R^a$, $R^b$, $R^c$, $R^d$ substituents]

where $R^{14}$ is selected from H, unsubstituted $C_1$-$C_{18}$ alkyl or $C_1$-$C_{18}$ alkyl substituted with fluoro, $C_3$-$C_8$ cycloalkyl, and aralkyl;

each of $R_a$, $R_b$, $R_c$, and $R_d$ is independently selected from: H, substituted and unsubstituted aryl, unsubstituted $C_1$-$C_{18}$ alkyl or $C_1$-$C_{18}$ alkyl substituted with fluoro, $C_3$-$C_8$ cycloalkyl, $C_2$-$C_{18}$ alkenyl, $C_3$-$C_8$ cycloalkenyl, and $C_2$-$C_{18}$ alkenyl, or wherein $R^c$ and $R^d$ form a ring;

the method comprising:

reacting an olefin of formula O-1

[Structure O-1: olefin with $R^a$, $R^b$, $R^c$, $R^d$ substituents]

with a hydroxylamine amination agent in the presence of a transition metal catalyst selected from copper and rhodium catalysts in a polar, hydroxylic and non-nucleophilic solvent, a carboxylic solvent or mixtures of the same at a temperature less than 30° C.;

wherein the hydroxylamine amination agent is selected from compounds of formulas AA-1, AA-2, AA-5, AA-6, AA-7, AA-8:

[Structure AA-1: aryl ring with $R^4$, $R^5$, $R^6$, $R^7$, $R^8$ substituents, with O—NR$^1$R$^2$]

[Structure AA-2: aryl ring with $R^4$, $R^5$, $R^6$, $R^7$, $R^8$ substituents, with C(O)—O—NR$^1$R$^2$]

[Structure AA-5: $R^9$—S(O)$_2$—O—NR$^1$R$^2$]

[Structure AA-6: $R^{10}$, $R^{11}$—P(O)—O—NR$^1$R$^2$]

[Structure AA-7: $R^{12}$O—C(O)—O—NR$^1$R$^2$]

[Structure AA-8: cyclic structure with $R^{13}$, $R^{14}$, $R^{15}$ and O—NR$^1$R$^2$]

wherein each $R^1$ and $R^2$ are independently selected from hydrogen, unsubstituted $C_1$-$C_{18}$ alkyl or $C_1$-$C_{18}$ alkyl substituted with fluoro, $C_3$-$C_8$ cycloalkyl, —Si(R$^3$)$_3$, allyl, aralkyl, substituted and unsubstituted aryl, and substituted and unsubstituted heteroaryl;

wherein $R^1$ and $R^2$ can be connected to form a cyclic amine having from 4 to 7 carbocyclic ring members;

each $R^3$ is independently selected from unsubstituted $C_1$-$C_{18}$ alkyl or $C_1$-$C_{18}$ alkyl substituted with fluoro and substituted or unsubstituted aryl;

each $R^4$, $R^5$, $R^6$, $R^7$, and $R^8$ are independently selected from hydrogen, nitro, fluoro, chloro, bromo, unsubstituted $C_1$-$C_{18}$ alkyl or $C_1$-$C_{18}$ alkyl substituted with fluoro, $C_3$-$C_8$ cycloalkyl, arylsulfonyl, alkylsulfonyl, mono-/di-/tri-fluoroalkylsulfonyl, trifluoromethyl, $R^{16}R^{17}NC(O)$—, $R^{18}O_2C$—, $(R^{19})_4N^+$—, and $(R^{20})_2P(O)$—;

$R^9$ is selected from unsubstituted $C_1$-$C_{18}$ alkyl or $C_1$-$C_{18}$ alkyl substituted with fluoro, and $C_3$-$C_8$ cycloalkyl;

$R^{10}$ and $R^{11}$ are independently selected from substituted and unsubstituted aryl;

wherein the number of substituents for substituted aryl may be from 1 to 5 and independently selected from nitro, fluoro, chloro, methyl, ethyl, isopropyl, tert-butyl, arylsulfonyl, alkylsulfonyl, mono-/di-/tri-fluoroalkylsulfonyl, trifluoromethyl, $R^{16}R^{17}NC(O)$—, $R^{18}O_2C$—, $(R^{19})_4N^+$, $(R^{20})_2P(O)$—, PEG$_m$-, and o-furanyl;

$R^{12}$ is selected from unsubstituted $C_1$-$C_{18}$ alkyl or $C_1$-$C_{18}$ alkyl substituted with fluoro, $C_3$-$C_8$ cycloalkyl, $C_1$-$C_{18}$ alkenyl, $C_3$-$C_8$ cycloalkenyl, substituted and unsubstituted aryl;

wherein the number of substituents for substituted aryl may be from 1 to 5 and independently selected from nitro, fluoro, chloro, methyl, ethyl, isopropyl, tert-butyl, arylsulfonyl, alkylsulfonyl, mono-/di-/tri-fluoroalkylsulfonyl, trifluoromethyl, $R^{16}R^{17}NC(O)$—, $R^{18}O_2C$—, $(R^{19})_4N^+$—, $(R^{20})_2P(O)$—, $PEG_m$-, and o-furanyl;

$R^{13}$ is selected from substituted and unsubstituted aryl, substituted and unsubstituted heteroaryl, unsubstituted $C_1$-$C_{18}$ alkyl or $C_1$-$C_{18}$ alkyl substituted with fluoro, $C_3$-$C_8$ cycloalkyl, and $CCl_3$, or when $R^{13}$ forms an aromatic or other ring system with $R^{15}$, then $R^{13}$ is selected from O, N, and C—$R^{20}$;

wherein the number of substituents for substituted aryl may be from 1 to 5 and wherein the number of substituents for substituted heteroaryl may be from 1 to 4 and each substituent is independently selected from nitro, fluoro, chloro, methyl, ethyl, isopropyl, tert-butyl, arylsulfonyl, alkylsulfonyl, mono-/di-/tri-fluoroalkylsulfonyl, trifluoromethyl, $R^{16}R^{17}NC(O)$—, $R^{18}O_2C$—, $(R^{19})_4N+$—, and $(R^{20})_2P(O)$—, $PEG_m$-, and o-furanyl;

$R^{14}$ is absent or selected from H, substituted and unsubstituted aryl, $C_3$-$C_8$ cycloalkyl, and unsubstituted $C_1$-$C_{18}$ alkyl or $C_1$-$C_{18}$ alkyl substituted with fluoro, wherein the number of substituents for substituted aryl may be from 1 to 5 and wherein the number of substituents for substituted heteroaryl may be from 1 to 4 and each substituent is independently selected from nitro, fluoro, chloro, methyl, ethyl, isopropyl, tert-butyl, arylsulfonyl, alkylsulfonyl, mono-/di-/tri-fluoroalkylsulfonyl, trifluoromethyl, $R^{16}R^{17}NC(O)$—, $R^{18}O_2C$—, $(R^{19})_4N^+$—, and $(R^{20})_2P(O)$—, $PEG_m$-, $R^{15}$ is selected from selected from substituted and unsubstituted aryl, unsubstituted $C_1$-$C_8$ alkyl or $C_1$-$C_{18}$ alkyl substituted with fluoro, and $C_3$-$C_8$ cycloalkyl, or when $R^{15}$ forms an aromatic or other ring system with $R^{13}$, then $R^{15}$ is CH or $CH_2$;

wherein the number of substituents for substituted aryl may be from 1 to 5 and each substituent is independently selected from nitro, fluoro, chloro, methyl, ethyl, isopropyl, tert-butyl, arylsulfonyl, alkylsulfonyl, mono-/di-/tri-fluoroalkylsulfonyl, trifluoromethyl, $R^{16}R^{17}NC(O)$—, $R^{18}O_2C$—, $(R^{19})_4N^+$—, and $(R^{20})_2P(O)$—, $PEG_m$-, where each m is independently from 1 to 6;

each $R^{16}$, $R^{17}$, $R^{18}$, $R^{19}$, $R^{20}$ is independently selected from H, $C_3$-$C_8$ cycloalkyl, substituted and unsubstituted aryl, substituted and unsubstituted heteroaryl, and unsubstituted $C_1$-$C_{18}$ alkyl and $C_1$-$C_{18}$ alkyl substituted with fluoro;

wherein the number of substituents for each substituted aryl may be from 1 to 5 and the number of substituents for each substituted heteroaryl may be from 1 to 4 and each substituent is independently selected from nitro, fluoro, chloro, methyl, ethyl, isopropyl, tert-butyl, arylsulfonyl, alkylsulfonyl, mono-/di-/tri-fluoroalkylsulfonyl, trifluoromethyl, $PEG_m$.

2. The process of claim 1, wherein the hydroxylamine amination agent is of formula AA-1.

3. The process of claim 1, wherein the hydroxylamine amination agent is of formula AA-2.

4. The process of claim 1, wherein the hydroxylamine amination agent is of formula AA-5.

5. The process of claim 1, wherein the hydroxylamine amination agent is of formula AA-6.

6. The process of claim 1, wherein the hydroxylamine amination agent is of formula AA-7.

7. The process of claim 1, wherein the hydroxylamine amination agent is of formula AA-8.

8. The process of claim 1, wherein the transition metal catalyst is a copper catalyst.

9. The process of claim 1, wherein the transition metal catalyst is a rhodium catalyst.

10. The process of claim 1, wherein the catalyst is selected from: $Rh_2(OAc)_4$, $Rh_2(octanoate)_4$, and $Rh_2(esp)_2$.

11. The process of claim 1, wherein the polar, hydroxylic and nonnucleophilic solvent comprises trifluoroethanol.

12. The process of claim 1, wherein the transition metal catalyst is incrementally introduced in batches of about 1 mol %.

13. The process of claim 1, wherein $R^c$ and $R^d$ form a ring.

14. The process of claim 10, wherein $R^c$ and $R^d$ form a ring.

* * * * *

UNITED STATES PATENT AND TRADEMARK OFFICE
CERTIFICATE OF CORRECTION

| | | |
|---|---|---|
| PATENT NO. | : 9,988,349 B2 | Page 1 of 1 |
| APPLICATION NO. | : 15/109396 | |
| DATED | : June 5, 2018 | |
| INVENTOR(S) | : Daniel Ess et al. | |

It is certified that error appears in the above-identified patent and that said Letters Patent is hereby corrected as shown below:

In the Specification

Column 1, Line 5, before "RELATED APPLICATION" insert:
--FEDERALLY SPONSORED RESEARCH STATEMENT
This invention was made with government support under grant number(s) GM031278 awarded by the National Institutes of Health (NIH). The government has certain rights in the invention.--

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*